United States Patent
Azuma et al.

(10) Patent No.: US 11,067,909 B2
(45) Date of Patent: Jul. 20, 2021

(54) TERPHENYL COMPOUND, ELECTROPHOTOGRAPHIC PHOTOSENSITIVE MEMBER, AND METHOD FOR PRODUCING TERPHENYL COMPOUND

(71) Applicant: KYOCERA Document Solutions Inc., Osaka (JP)

(72) Inventors: Jun Azuma, Osaka (JP); Kensuke Kojima, Osaka (JP); Tomofumi Shimizu, Osaka (JP); Hideki Okada, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 0 days.

(21) Appl. No.: 16/632,197

(22) PCT Filed: Jul. 17, 2018

(86) PCT No.: PCT/JP2018/026722
§ 371 (c)(1),
(2) Date: Jan. 17, 2020

(87) PCT Pub. No.: WO2019/017336
PCT Pub. Date: Jan. 24, 2019

(65) Prior Publication Data
US 2020/0231535 A1    Jul. 23, 2020

(30) Foreign Application Priority Data
Jul. 21, 2017  (JP) .............................. JP2017-141457

(51) Int. Cl.
*G03G 5/06* (2006.01)
*G03G 5/05* (2006.01)
*C07C 209/06* (2006.01)
*C07C 211/54* (2006.01)
*G03G 5/047* (2006.01)

(52) U.S. Cl.
CPC ..... *G03G 5/061446* (2020.05); *C07C 209/06* (2013.01); *C07C 211/54* (2013.01); *G03G 5/047* (2013.01); *G03G 5/056* (2013.01); *G03G 5/0546* (2013.01); *G03G 5/0564* (2013.01); *G03G 5/06142* (2020.05)

(58) Field of Classification Search
CPC ............. G03G 5/061446; G03G 5/056; G03G 5/06142
See application file for complete search history.

(56) References Cited

U.S. PATENT DOCUMENTS

| 4,273,846 | A | * | 6/1981 | Pai | ........................ | C09B 57/008 |
| | | | | | | 430/58.75 |
| 7,514,191 | B2 | | 4/2009 | Yanus et al. | | |
| 8,486,594 | B2 | | 7/2013 | Nagai et al. | | |
| 8,673,792 | B2 | | 3/2014 | Nagai et al. | | |
| 8,993,203 | B2 | * | 3/2015 | Fujii | ...................... | G03G 21/18 |
| | | | | | | 430/58.65 |
| 2007/0254223 | A1 | | 11/2007 | Yanus et al. | | |

(Continued)

FOREIGN PATENT DOCUMENTS

JP    2007-293342 A    11/2007
JP    2008166538 A  *  7/2008
(Continued)

OTHER PUBLICATIONS

English language machine translation of JP 2008-166538 (Year: 2008).*
English language machine translation of JP 6350316. (Year: 2018).*
Anthony Chartoire et al.; "Highly Active Well-Defined Palladium Precatalysts for the Efficient Amination of Aryl Chlorides"; Organometallics; 2011; pp. 4432-4436; vol. 30.

* cited by examiner (Continued)

*Primary Examiner* — Christopher D Rodee
(74) *Attorney, Agent, or Firm* — Studebaker & Brackett PC

(57) ABSTRACT

A compound is represented by general formula (1). In general formula (1), $R^1$ and $R^2$ each represent, independently of one another, a hydrogen atom, a methyl group, or an ethyl group, and a sum of the number of carbon atoms of the chemical group represented by $R^1$ and the number of carbon atoms of the chemical group represented by $R^2$ is 2. $R^3$ and $R^4$ each represent, independently of one another, a hydrogen atom, a methyl group, or an ethyl group, and a sum of the number of carbon atoms of the chemical group represented by $R^3$ and the number of carbon atoms of the chemical group represented by $R^1$ is 2. A photosensitive layer of an electrophotographic photosensitive member contains at least a charge generating material, a hole transport material, and a binder resin. The hole transport material includes a compound represented by general formula (1)

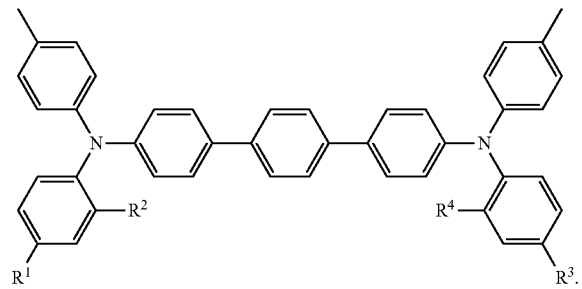

(1)

9 Claims, 2 Drawing Sheets

(56) References Cited

U.S. PATENT DOCUMENTS

| | | |
|---|---|---|
| 2007/0254226 A1 | 11/2007 | Yanus et al. |
| 2009/0053633 A1 | 2/2009 | Nagai et al. |
| 2013/0280652 A1 | 10/2013 | Nagai et al. |
| 2015/0118608 A1* | 4/2015 | Azuma ................ G03G 5/0618 430/58.25 |
| 2015/0378269 A1* | 12/2015 | Okada .................. C07C 251/80 430/58.45 |
| 2017/0242352 A1* | 8/2017 | Ogaki .................... G03G 5/043 |

FOREIGN PATENT DOCUMENTS

| | | | |
|---|---|---|---|
| JP | 2009-169023 A | | 7/2009 |
| JP | 2014-146001 A | | 8/2014 |
| JP | 2014-149363 A | | 8/2014 |
| JP | 2016142929 A | * | 8/2016 |
| JP | 2019077844 A | * | 5/2019 |
| WO | 2007/086439 A1 | | 8/2007 |
| WO | 2017/073176 A1 | | 5/2017 |

TERPHENYL COMPOUND, ELECTROPHOTOGRAPHIC PHOTOSENSITIVE MEMBER, AND METHOD FOR PRODUCING TERPHENYL COMPOUND

TECHNICAL FIELD

The present invention relates to a compound (particularly, a terphenyl compound), an electrophotographic photosensitive member, and a method for producing a compound (particularly, a terphenyl compound).

BACKGROUND ART

Electrophotographic photosensitive members are used as image bearing members of electrophotographic image forming apparatuses (for example, printers or multifunction peripherals). Electrophotographic photosensitive members each include a photosensitive layer. Examples of electrophotographic photosensitive members include single-layer electrophotographic photosensitive members and multi-layer electrophotographic photosensitive members. The single-layer electrophotographic photosensitive members each include a single-layer photosensitive layer having a charge generation function and a charge transport function. The multi-layer electrophotographic photosensitive members each include a photosensitive layer including a charge generating layer having a charge generation function and a charge transport layer having a charge transport function.

Patent Literature 1 discloses an imaging member including at least one charge transport layer containing a terphenyl diamine having a specific structure as a charge transport material. The terphenyl diamine being a charge transport material is for example represented by chemical formula (II).

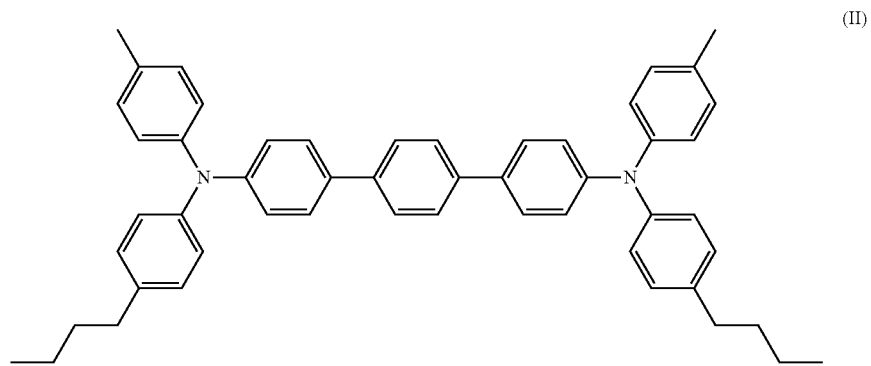 [SMILES: CCCCc1ccc(N(c2ccc(C)cc2)c2ccc(-c3ccc(-c4ccc(N(c5ccc(C)cc5)c5ccc(CCCC)cc5)cc4)cc3)cc2)cc1]

(II)

CITATION LIST

Patent Literature

[Patent Literature 1]
Japanese Patent Application Laid-Open Publication No. 2007-293342

SUMMARY OF INVENTION

Technical Problem

However, studies by the inventors of the present invention revealed that the imaging member disclosed in Patent Literature 1 is not sufficient in terms of electrical characteristics.

The present invention was achieved in consideration of the above-described problem and an object thereof is to provide a compound capable of improving, when contained in a photosensitive layer of an electrophotographic photosensitive member, electrical characteristics of the electrophotographic photosensitive member and inhibiting crystallization in the photosensitive layer. Another object of the present invention is to provide an electrophotographic photosensitive member improved in electrical characteristics and enabled to inhibit crystallization in a photosensitive layer thereof. Still another object of the present invention is to provide a method for producing the above-described compound, which offers an improved yield of the compound and allows the compound to particularly improve sensitivity of an electrophotographic photosensitive member when the compound is contained in a photosensitive layer of the electrophotographic photosensitive member.

Solution to Problem

A compound according to the present invention is represented by general formula (1).

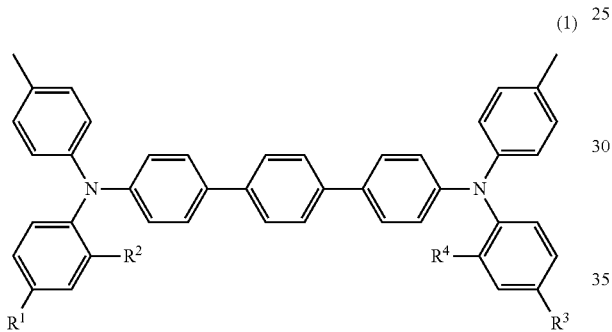

In the general formula (1), $R^1$ and $R^2$ each represent, independently of one another, a hydrogen atom, a methyl group, or an ethyl group, and a sum of the number of carbon atoms of the chemical group represented by $R^1$ and the number of carbon atoms of the chemical group represented by $R^2$ is 2, $R^3$ and $R^4$ each represent, independently of one another, a hydrogen atom, a methyl group, or an ethyl group, and a sum of the number of carbon atoms of the chemical group represented by $R^3$ and the number of carbon atoms of the chemical group represented by $R^4$ is 2.

An electrophotographic photosensitive member according to the present invention includes a conductive substrate and a photosensitive layer. The photosensitive layer contains at least a charge generating material, a hole transport material, and a binder resin. The photosensitive layer includes a charge generating layer containing the charge generating material and a charge transport layer containing the hole transport material and the binder resin. Alternatively, the photosensitive layer is a single-layer photosensitive layer containing the charge generating material, the hole transport material, and the binder resin. The hole transport material includes the above-described compound.

A method for producing a compound according to the present invention produces the above-described compound. The method for producing the compound according to the present invention includes causing a reaction between a compound represented by general formula (a), a compound represented by general formula (b), and a compound represented by general formula (c) using a ligand represented by general formula (30) and a transition metal-containing catalyst or using the transition metal-containing catalyst coordinated with the ligand.

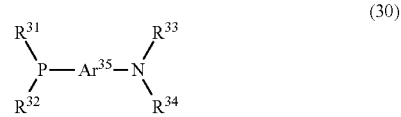

In the general formula (30), $R^{31}$, $R^{32}$, $R^{33}$, and $R^{34}$ each represent, independently of one another, an alkyl group having a carbon number of at least 1 and no greater than 6. $Ar^{35}$ represents an arylene group having a carbon number of at least 6 and no greater than 14.

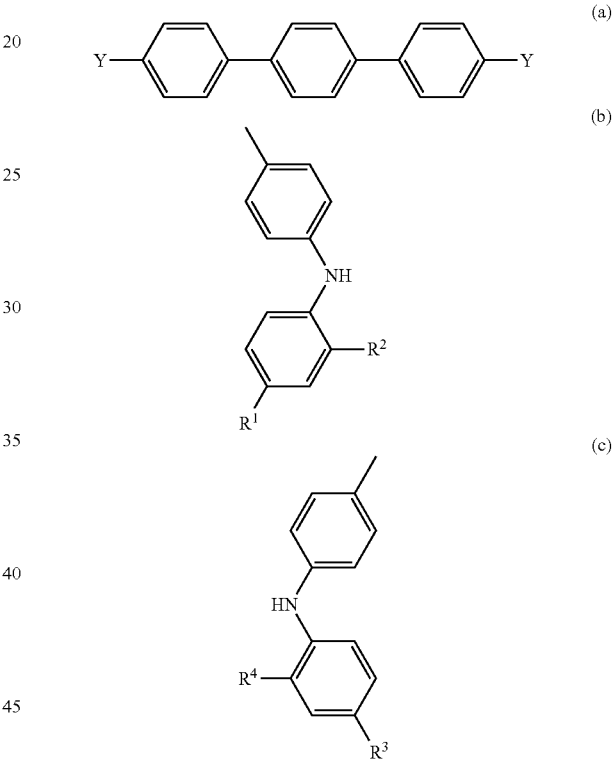

In the general formula (a), Y represents a halogen atom. In the general formula (b), $R^1$ and $R^2$ each represent, independently of one another, a hydrogen atom, a methyl group, or an ethyl group, and a sum of the number of carbon atoms of the chemical group represented by $R^1$ and the number of carbon atoms of the chemical group represented by $R^2$ is 2. In the general formula (c), $R^3$ and $R^4$ each represent, independently of one another, a hydrogen atom, a methyl group, or an ethyl group, and a sum of the number of carbon atoms of the chemical group represented by $R^3$ and the number of carbon atoms of the chemical group represented by $R^4$ is 2.

Advantageous Effects of Invention

The compound according to the present invention is capable of improving, when contained in a photosensitive layer of an electrophotographic photosensitive member, electrical characteristics of the electrophotographic photosensitive member and inhibiting crystallization in the photosensitive layer. The electrophotographic photosensitive member according to the present invention has improved electrical characteristics and is able to inhibit crystallization in the photosensitive layer thereof. The method for producing a compound according to the present invention offers an improved yield of the compound and allows the compound to particularly improve sensitivity of an electrophotographic photosensitive member when the compound is contained in a photosensitive layer of the electrophotographic photosensitive member.

DESCRIPTION OF EMBODIMENTS

Figure 1A:
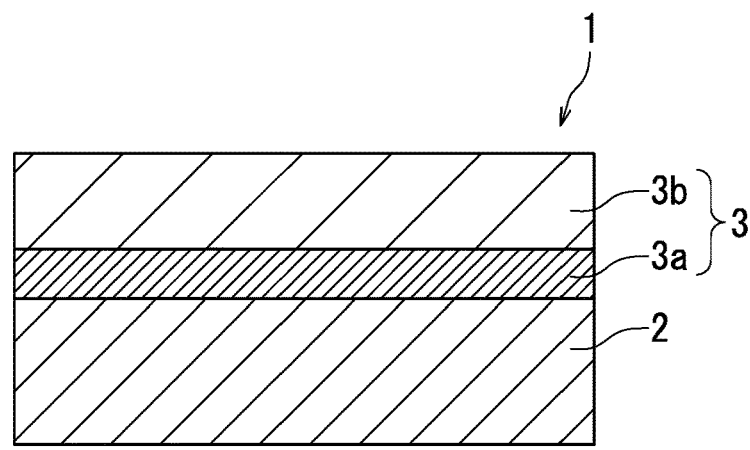
FIG. 1A is a partial cross-sectional view illustrating an example of an electrophotographic photosensitive member containing a compound according to an embodiment of the present invention.

The following describes an embodiment of the present invention in detail. However, the present invention is not in any way limited by the following embodiment. Appropriate changes may be made when practicing the present invention within the intended scope of the present invention. Although description is omitted as appropriate in some instances in order to avoid repetition of description, such omission does not limit the essence of the present invention. The term "-based" may be appended to the name of a chemical compound in order to form a generic name encompassing both the chemical compound itself and derivatives thereof. Also, when the term "-based" is appended to the name of a chemical compound used in the name of a polymer, the term indicates that a repeating unit of the polymer originates from the chemical compound or a derivative thereof. A chemical group "optionally having a chemical group" means a chemical group "optionally substituted with a chemical group". A chemical group "having a chemical group" means a chemical group "substituted with a chemical group". A chemical group "optionally having a halogen atom" means a chemical group "optionally substituted with a halogen atom". A chemical group "having a halogen atom" means a chemical group "substituted with a halogen atom".

Hereinafter, a halogen atom, an alkyl group having a carbon number of at least 1 and no greater than 6, an alkyl group having a carbon number of at least 1 and no greater than 5, an alkyl group having a carbon number of at least 1 and no greater than 4, an alkyl group having a carbon number of at least 1 and no greater than 3, an alkoxy group having a carbon number of at least 1 and no greater than 6, an alkoxy group having a carbon number of at least 1 and no greater than 3, an aryl group having a carbon number of at least 6 and no greater than 14, an aryl group having a carbon number of at least 6 and no greater than 10, an arylene group having a carbon number of at least 6 and no greater than 14, a cycloalkyl group having a carbon number of at least 5 and no greater than 7, a cycloalkylidene group having a carbon number of at least 5 and no greater than 14, a cycloalkylidene group having a carbon number of at least 5 and no greater than 12, an alkoxycarbonyl group having a carbon number of at least 2 and no greater than 7, and an alkoxycarbonyl group having a carbon number of at least 2 and no greater than 6 each refer to the following, unless otherwise stated.

Examples of halogen atoms (halogen groups) include a fluorine atom (a fluoro group), a chlorine atom (a chloro group), a bromine atom (a bromo group), and an iodine atom (an iodine group).

An alkyl group having a carbon number of at least 1 and no greater than 6, an alkyl group having a carbon number of at least 1 and no greater than 5, an alkyl group having a carbon number of at least 1 and no greater than 4, and an alkyl group having a carbon number of at least 1 and no greater than 3 as used herein each refer to an unsubstituted straight chain or branched chain alkyl group. Examples of the alkyl group having a carbon number of at least 1 and no greater than 6 include a methyl group, an ethyl group, an n-propyl group, an isopropyl group, an n-butyl group, a sec-butyl group, a tert-butyl group, an n-pentyl group, an isopentyl group, a neopentyl group, a 1,2-dimethylpropyl group, a 1-ethyl-1-methylpropyl group, and a hexyl group. Out of the chemical groups listed as examples of the alkyl group having a carbon number of at least 1 and no greater than 6, the chemical groups having a carbon number of at least 1 and no greater than 5 are examples of the alkyl group having a carbon number of at least 1 and no greater than 5. Out of the chemical groups listed as examples of the alkyl group having a carbon number of at least 1 and no greater than 6, the chemical groups having a carbon number of at least 1 and no greater than 4 are examples of the alkyl group having a carbon number of at least 1 and no greater than 4. Out of the chemical groups listed as examples of the alkyl group having a carbon number of at least 1 and no greater than 6, the chemical groups having a carbon number of at least 1 and no greater than 3 are examples of the alkyl group having a carbon number of at least 1 and no greater than 3.

An alkoxy group having a carbon number of at least 1 and no greater than 6 and an alkoxy group having a carbon number of at least 1 and no greater than 3 as used herein each refer to an unsubstituted straight chain or branched chain alkoxy group. Examples of the alkoxy group having a carbon number of at least 1 and no greater than 6 include a methoxy group, an ethoxy group, an n-propoxy group, an isopropoxy group, an n-butoxy group, a sec-butoxy group, a tert-butoxy group, an n-pentoxy group, an isopentoxy group, a neopentoxy group, a hexyloxy group, and a 1-ethyl-1-methylpropoxy group. Out of the chemical groups listed as examples of the alkoxy group having a carbon number of at least 1 and no greater than 6, the chemical groups having a carbon number of at least 1 and no greater than 3 are examples of the alkoxy group having a carbon number of at least 1 and no greater than 3.

An aryl group having a carbon number of at least 6 and no greater than 14 and an aryl group having a carbon number of at least 6 and no greater than 10 as used herein each refer to an unsubstituted aryl group. Examples of the aryl group having a carbon number of at least 6 and no greater than 14 include a phenyl group, a naphthyl group, an indacenyl group, a biphenylenyl group, an acenaphthylenyl group, an anthryl group, and a phenanthryl group. Examples of the aryl group having a carbon number of at least 6 and no greater than 10 include a phenyl group and a naphthyl group.

An arylene group having a carbon number of at least 6 and no greater than 14 as used herein refers to an unsubstituted arylene group. Examples of the arylene group having a carbon number of at least 6 and no greater than 14 include a phenylene group, a naphthalenediyl group, an indacenediyl group, a biphenylenediyl group, an acenaphthylenediyl group, an anthrylenediyl group, and a phenanthrenediyl group.

A cycloalkyl group having a carbon number of at least 5 and no greater than 7 as used herein refers to an unsubstituted cycloalkyl group. Examples of the cycloalkyl group having a carbon number of at least 5 and no greater than 7 include a cyclopentyl group, a cyclohexyl group, and a cycloheptyl group.

A cycloalkylidene group having a carbon number of at least 5 and no greater than 14 and a cycloalkylidene group having a carbon number of at least 5 and no greater than 12 as used herein each refer to an unsubstituted cycloalkylidene group. Examples of the cycloalkylidene group having a carbon number of at least 5 and no greater than 14 include a cyclopentylidene group, a cyclohexylidene group, a cycloheptylidene group, a cyclooctylidene group, a cyclononylidene group, a cyclodecylidene group, a cycloundecylidene group, a cyclododecylidene group, a cyclotridecylidene group, and a cyclotetradecylidene group. The cycloalkylidene group having a carbon number of at least 5 and no greater than 14 is represented by general formula shown below. In the general formula, t represents an integer of at least 1 and no greater than 10, and asterisks each represent a bond. Preferably, t represents an integer of at least 1 and no greater than 8, more preferably an integer of 1, 2, or 8, and further preferably an integer of 2 or 8.

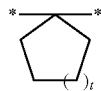

An alkoxycarbonyl group having a carbon number of at least 2 and no greater than 7 and an alkoxycarbonyl group having a carbon number of at least 2 and no greater than 6 as used herein each refer to an unsubstituted straight chain or branched chain alkoxycarbonyl group. The alkoxycarbonyl group having a carbon number of at least 2 and no greater than 7 is a carbonyl group having an alkyl group having a carbon number of at least 1 and no greater than 6. The alkoxycarbonyl group having a carbon number of at least 2 and no greater than 6 is a carbonyl group having an alkyl group having a carbon number of at least 1 and no greater than 5.

<Compound Represented by General Formula (1)>

The present embodiment relates to a compound (particularly, a terphenyl compound). The compound according the present embodiment is a compound represented by general formula (1) shown below (also referred to below as a compound (1)).

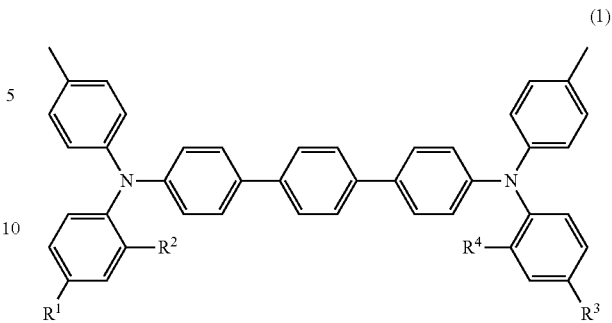

In general formula (1), $R^1$ and $R^2$ each represent, independently of one another, a hydrogen atom, a methyl group, or an ethyl group, and a sum of the number of carbon atoms of the chemical group represented by $R^1$ and the number of carbon atoms of the chemical group represented by $R^2$ is 2. $R^3$ and $R^4$ each represent, independently of one another, a hydrogen atom, a methyl group, or an ethyl group, and a sum of the number of carbon atoms of the chemical group represented by $R^3$ and the number of carbon atoms of the chemical group represented by $R^4$ is 2.

When contained in a photosensitive layer of an electrophotographic photosensitive member (also referred to below as a photosensitive member), the compound (1) can improve electrical characteristics of the photosensitive member and inhibit crystallization in the photosensitive layer. The following describes reasons therefor. Note that electrical characteristics of the photosensitive member are for example chargeability, sensitivity, and exposure memory-inhibiting performance of the photosensitive member. Exposure memory-inhibiting performance refers to an ability to inhibit occurrence of exposure memory in the photosensitive member. Exposure memory is a phenomenon that occurs on a surface of the photosensitive member due to influence of light exposure. Specifically, the phenomenon is that a region corresponding to a region exposed to light during a previous rotation of the photosensitive member is charged to a lower potential than a region corresponding to a region not exposed to light during the previous rotation. Occurrence of exposure memory in the photosensitive member results in occurrence of a ghost image in an output image. The ghost image due to exposure memory is an image defect described as a darken region in the output image resulting from a corresponding region exposed to light during the previous rotation of the photosensitive member.

Firstly, in general formula (1), $R^1$ and $R^2$ each represent, independently of one another, a hydrogen atom, a methyl group, or an ethyl group. Furthermore, $R^3$ and $R^4$ each represent, independently of one another, a hydrogen atom, a methyl group, or an ethyl group. Such chemical groups enable improvement of sensitivity and exposure memory-inhibiting performance of the photosensitive member.

Secondly, in general formula (1), the sum of the number of carbon atoms of the chemical group represented by $R^1$ and the number of carbon atoms of the chemical group represented by $R^2$ is 2. Furthermore, the sum of the number of carbon atoms of the chemical group represented by $R^3$ and the number of carbon atoms of the chemical group represented by $R^4$ is 2. Such chemical groups enable improvement of sensitivity of the photosensitive member, improvement of exposure memory-inhibiting performance of the photosensitive member, and inhibition of crystallization in the photosensitive layer. In a situation in which the sum is less than 2, sensitivity of the photosensitive member decreases. Furthermore, in a situation in which the sum is less than 2, it is impossible to inhibit crystallization in the photosensitive layer. This is thought to be because the above-described compound has low solubility in a solvent for formation of the photosensitive layer and low compatibility with a binder resin for formation of the photosensitive layer. On the other hand, in a situation in which the sum is greater than 2, sensitivity and exposure memory-inhibiting performance of the photosensitive member decrease.

Thirdly, in general formula (1), $R^1$ is attached in the para position of a phenyl group, and $R^2$ is attached in the ortho position of the phenyl group. $R^3$ is attached in the para position of a phenyl group, and $R^4$ is attached in the ortho position of the phenyl group. Such chemical groups enable improvement of sensitivity of the photosensitive member, improvement of exposure memory-inhibiting performance of the photosensitive member, and inhibition of crystallization in the photosensitive layer. In a situation in which the chemical groups are attached in the meta position and the para position of each phenyl group, sensitivity of the photosensitive member decreases. In a situation in which the chemical groups are attached in the meta position and the para position of each phenyl group, it is impossible to inhibit crystallization in the photosensitive layer. Furthermore, in a situation in which the chemical groups are attached in the meta position of each phenyl group, one or both of sensitivity and exposure memory-inhibiting performance of the photosensitive member decrease.

Fourthly, the compound (1) has two methylphenyl groups. This enables improvement of sensitivity of the photosensitive member. This also enables inhibition of crystallization in the photosensitive layer. Crystallization in the photosensitive layer is inhibited presumably because the compound (1) has two methylphenyl groups, and thus the compound (1) has improved solubility in the solvent for formation of the photosensitive layer and improved compatibility with the binder resin for formation of the photosensitive layer.

Examples of preferable compounds (1) include compounds represented by chemical formulae (1-1), (1-2), and (1-3) (also referred to below as compounds (1-1), (1-2), and (1-3), respectively).

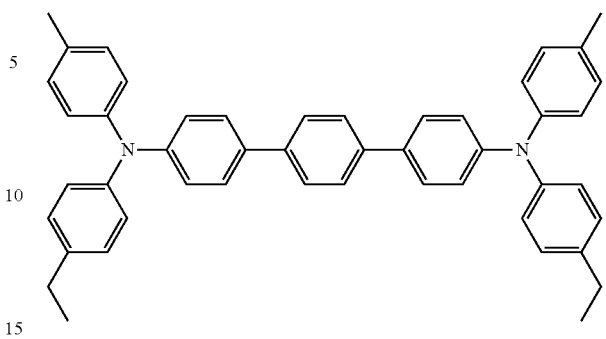

<Production Method of Compound (1)>
(Reaction (r1))

The compound (1) is for example synthesized according to a reaction represented by reaction formula (r1) (also referred to below as a reaction (r1)) or according to a method conforming therewith. Y in general formula (a) shown in reaction formula (r1) represents a halogen atom. $R^1$, $R^2$, $R^3$, and $R^4$ in general formulae (b) and (c) are respectively the same as defined for $R^1$, $R^2$, $R^3$, and $R^4$ in general formula (1). Compounds represented by general formulae (a), (b), and (c) are also referred to below as compounds (a), (b), and (c), respectively.

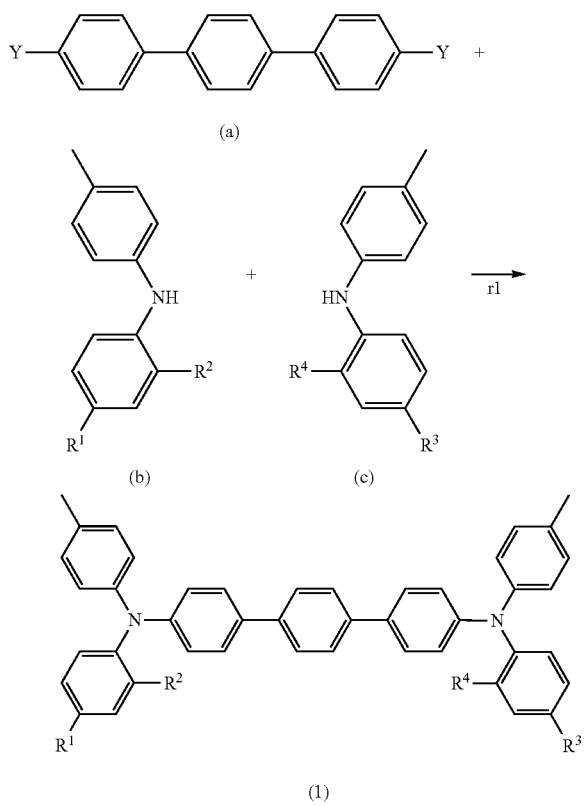

The production method of the compound (1) includes causing a reaction between the compound (a), the compound (b), and the compound (c) (i.e., reaction (r1)). Specifically, in the reaction (r1), 1 mole equivalent of the compound (a), 1 mole equivalent of the compound (b), and 1 mole equivalent of the compound (c) are caused to react to give 1 mole equivalent of the compound (1). In the reaction (r1), a difference between a polarity of the compound (a) being a raw material and a polarity of the compound (1) being a reaction product is relatively large. Furthermore, a difference between a polarity of the compounds (b) and (c) being raw materials and the polarity of the compound (1) being a reaction product is relatively large. Because of the differences in polarities, the reaction (r1) allows the compound (1) to be easily purified. In a situation in which $R^1$ and $R^3$ are the same as each other and $R^2$ and $R^4$ are the same as each other in general formula (1), 2 mole equivalents of the compound (b) is used instead of 1 mole equivalent of the compound (b) and 1 mole equivalent of the compound (c).

Preferably, the reaction (r1) is carried out using a ligand represented by general formula (30) (also referred to below as a ligand (30)) and a transition metal-containing catalyst. Alternatively, the reaction (r1) is preferably carried out using a transition metal-containing catalyst coordinated with the ligand (30).

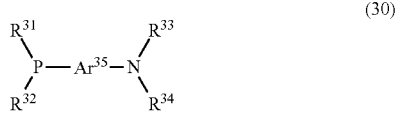

(30)

In general formula (30), $R^{31}$, $R^{32}$, $R^{33}$, and $R^{34}$ each represent, independently of one another, an alkyl group having a carbon number of at least 1 and no greater than 6. $Ar^{35}$ represents an arylene group having a carbon number of at least 6 and no greater than 14.

It is possible to improve the yield of the compound (1) by carrying out the reaction (r1) using the transition metal-containing catalyst and the ligand (30). It is also possible to particularly improve sensitivity of the photosensitive member through the photosensitive layer thereof containing the compound (1) obtained by carrying out the reaction (r1) as described above. The reason for the above is thought to be as follows. The ligand (30) has a specific structure and includes an electron-donating nitrogen atom. The ligand (30) therefore has an improved ability to donate electrons to the transition metal-containing catalyst. Because of the improved electron-donating ability, the transition metal-containing catalyst becomes highly active to promote the reaction (r1), improving the yield of the compound (1). As a result of the yield of the compound (1) being improved, the degree of purity of the compound (1) increases, and sensitivity of the photosensitive member is particularly improved.

In general formula (30), the alkyl group having a carbon number of at least 1 and no greater than 6 that may be represented by $R^{31}$, $R^{32}$, $R^{33}$, and $R^{34}$ is preferably an alkyl group having a carbon number of at least 1 and no greater than 4, and more preferably a methyl group or a tert-butyl group. The arylene group having a carbon number of at least 6 and no greater than 14 that may be represented by $Ar^{35}$ is preferably a naphthalenediyl group or a phenylene group, and more preferably a phenylene group.

Preferably, the ligand (30) is a ligand represented by chemical formula (L-1) (also referred to below as a ligand (L-1)). Note that the ligand (L-1) is (4-dimethyl aminophenyl)di-tert-butylphosphine.

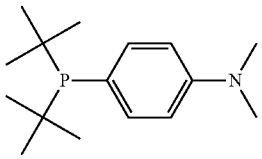

(L-1)

The coordination number for the ligand (30) is not particularly limited but is for example 1 or 2.

Examples of transition metals that can be contained in the catalyst include nickel, palladium, platinum, rhodium, ruthenium, iridium, and cobalt. The catalyst preferably contains, as a transition metal, palladium or nickel, and more preferably contains palladium. Examples of palladium-containing catalysts include palladium(II) acetate, palladium(II) chloride, hexachloro palladium(IV) sodium tetrahydrate, and tris(dibenylideneacetone)dipalladium(O). Examples of preferable palladium-containing catalysts include palladium(II) acetate and palladium(II) chloride.

In order to improve the yield of the compound (1) and particularly improve sensitivity of the photosensitive member through the photosensitive layer thereof containing the compound (1), preferably, the reaction (r1) is carried out using the ligand (L-1) and palladium(II) acetate. Alternatively, the reaction (r1) is preferably carried out using palladium(II) acetate coordinated with the ligand (L-1).

In order to improve the yield of the compound (1) and particularly improve sensitivity of the photosensitive member through the photosensitive layer thereof containing the compound (1), preferably, the reaction (r1) is carried out using the ligand (L-1) and palladium(II) chloride. Alternatively, the reaction (r1) is preferably carried out using palladium(II) chloride coordinated with the ligand (L-1). Examples of preferable palladium(II) chloride coordinated with the ligand (L-1) include a coordination catalyst represented by chemical formula (L-2) (also referred to below as a coordination catalyst (L-2)). A bond between P and Pd in chemical formula (L-2) is a coordinate bond.

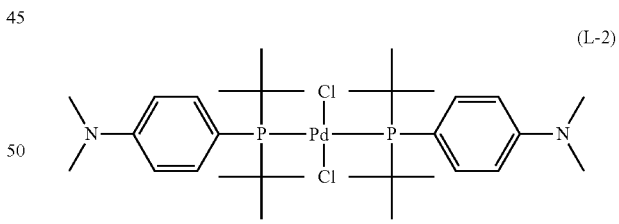

(L-2)

Note that the reaction (r1) may be carried out using a ligand other than the ligand (30) (also referred to below as an alternative ligand) and a transition metal-containing catalyst. Furthermore, the reaction (r1) may be carried out using a transition metal-containing catalyst coordinated with an alternative ligand. Examples of alternative ligands include ligands represented by chemical formulae (L-3), (L-4), and (L-5) (also referred to below as ligands (L-3), (L-4), and (L-5), respectively), tricyclohexylphosphine (also referred to below as a ligand (L-6)), triphenylphosphine, and methyldiphenylphosphine. Note that the ligand (L-4) is 1,1'-bis(diphenylphosphino)ferrocene. "Ph" in chemical formula (L-4) represents a phenyl group.

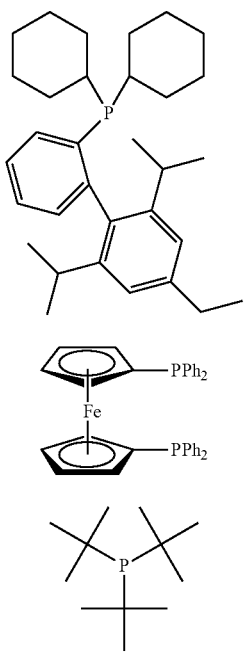

(L-3)

(L-4)

(L-5)

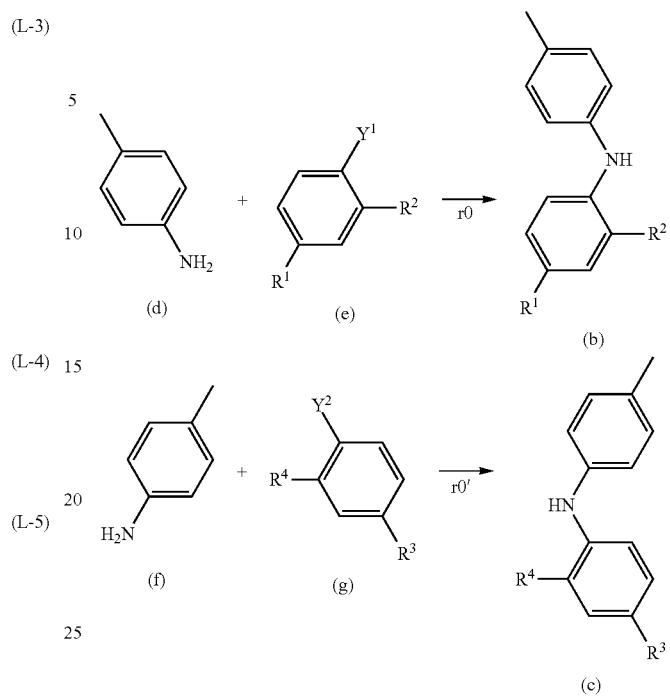

The reaction (r1) may be carried out in the presence of a base. Examples of bases include sodium tert-butoxide, tripotassium phosphate, and caesium fluoride. More preferably, at least 1 mole equivalent and no greater than 10 mole equivalents of a base is added relative to 1 mole equivalent of the compound (b).

The reaction (r1) may be carried out in a solvent. Examples of solvents include xylene, toluene, tetrahydrofuran, and dimethyl formamide.

Preferably, a reaction temperature of the reaction (r1) is at least 80° C., and no greater than 140° C. Preferably, a reaction time of the reaction (r1) is at least 1 hour and no greater than 10 hours. The reaction (r1) may be carried out under an inert gas (for example, nitrogen gas or argon gas) atmosphere.

(Reaction (r0) and Reaction (r0'))

The compound (b) may for example be synthesized according to a reaction represented by reaction formula (r0) (also referred to below as a reaction (r0)) or according to a method conforming therewith. The production method of the compound (1) may further include causing a reaction between a compound represented by chemical formula (d) and a compound represented by general formula (e) to give the compound (b). The compound (c) may for example be synthesized according to a reaction represented by reaction formula (r0') (also referred to below as a reaction (r0')) or according to a method conforming therewith. The production method of the compound (1) may further include causing a reaction between a compound represented by chemical formula (f) and a compound represented by general formula (g) to give the compound (c). The compounds represented by chemical formula (d), general formula (e), chemical formula (f), and general formula (g) are also referred to below as compounds (d), (e), (f), and (g), respectively.

$R^1$ and $R^2$ in general formula (e) and $R^3$ and $R^4$ in general formula (g) are the same as defined for $R^1$, $R^2$, $R^3$, and $R^4$ in general formula (1). $Y^1$ in general formula (e) represents a halogen atom. $Y^2$ in general formula (g) represents a halogen atom. In order to improve the yield of the compound (1), $Y^1$ in general formula (e) and $Y^2$ in general formula (g) are each preferably a chlorine atom or a bromine atom, and more preferably a bromine atom.

The reaction (r1) is carried out using the compound (b) obtained through the reaction (r0) and the compound (c) obtained through the reaction (r0'). Note that in a situation in which $R^1$ and $R^3$ are the same as each other and $R^2$ and $R^4$ are the same as each other in general formula (1), the reaction (r0') can be omitted and the compound (b) obtained through the reaction (r0) can be used in the reaction (r1). Furthermore, in a situation in which compounds (b) and (c) produced through reactions different from the reactions (r0) and (r0') are used, or in a situation in which commercially available compounds (b) and (c) are used, the reactions (r0) and (r0') can be omitted.

In the reaction (r0), 1 mole equivalent of the compound (d) and 1 mole equivalent of the compound (e) are caused to react to give 1 mole equivalent of the compound (b). In the reaction (r0'), 1 mole equivalent of the compound (f) and 1 mole equivalent of the compound (g) are caused to react to give 1 mole equivalent of the compound (c).

In order to improve the yield of the compound (1) and particularly improve sensitivity of the photosensitive member through the photosensitive layer thereof containing the compound (1), preferably, the reaction (r0) and the reaction (r0') are carried out using a transition metal-containing catalyst and the ligand (30). In the reaction (r0) and the reaction (r0'), the ligand (30) may be coordinated to the transition metal-containing catalyst. Note that the reaction (r0) and the reaction (r0') may be carried out using a transition metal-containing catalyst and an alternative ligand.

The reaction (r0) and the reaction (r0') may be carried out in the presence of a base. Examples of bases include sodium tert-butoxide, tripotassium phosphate, and caesium fluoride. More preferably, at least 1 mole equivalent and no greater than 10 mole equivalents of a base is added relative to 1 mole equivalent of the compound (b) or (f).

The reaction (r0) and the reaction (r0') may be carried out in a solvent Examples of solvents include xylene, toluene, tetrahydrofuran, and dimethyl formamide.

Preferably, a reaction temperature of the reaction (r0) and the reaction (r0') is at least 80° C., and no greater than 140° C. Preferably, a reaction time of the reaction (r0) and the reaction (r0') is at least 1 hour and no greater than 10 hours. The reaction (r0) and the reaction (r0') may be carried out under an inert gas (for example, nitrogen gas or argon gas) atmosphere.

After the reaction (r0) and the reaction (r0'), the resultant compounds (b) and (c) may be used unpurified in the reaction (r1). Omitting purification simplifies the production method and reduces production costs.

<Photosensitive Member>

The following describes a photosensitive member including a photosensitive layer containing the compound (1) according to the present embodiment. The photosensitive member includes a conductive substrate and a photosensitive layer. The photosensitive layer contains at least a charge generating material, a hole transport material, and a binder resin. The photosensitive member may be a multi-layer electrophotographic photosensitive member (also referred to below as a multi-layer photosensitive member) or a single-layer electrophotographic photosensitive member (also referred to below as a single-layer photosensitive member).

(Multi-Layer Photosensitive Member)

Figure 1B:
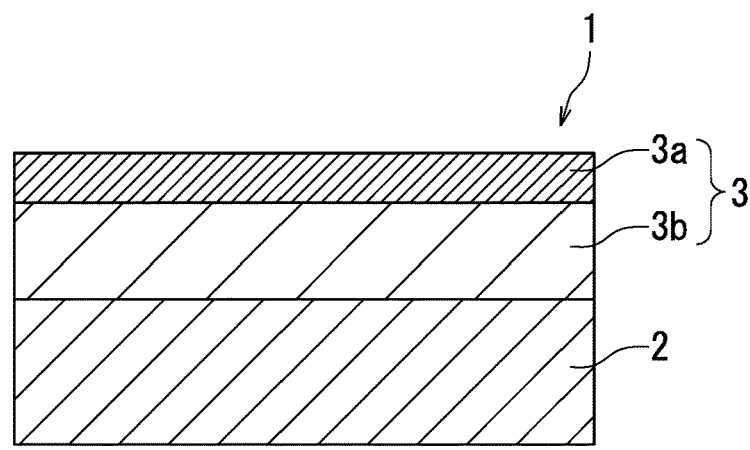
FIG. 1B is a partial cross-sectional view illustrating an example of the electrophotographic photosensitive member containing the compound according to the embodiment of the present invention.
Figure 1C:
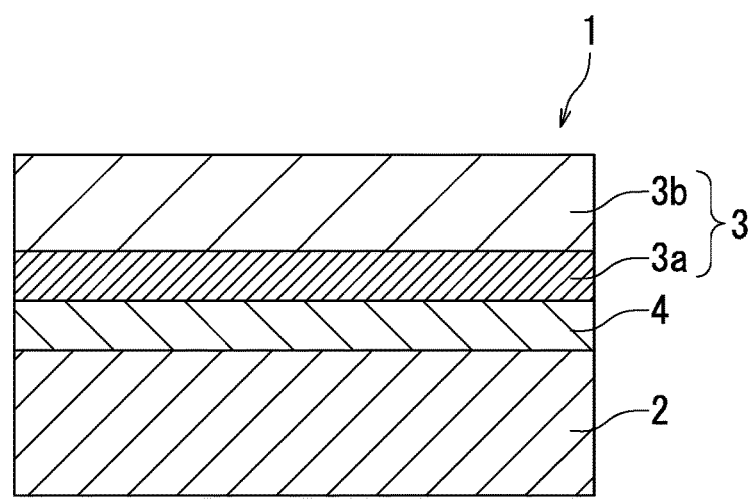
FIG. 1C is a partial cross-sectional view illustrating an example of the electrophotographic photosensitive member containing the compound according to the embodiment of the present invention.

The following describes a photosensitive member 1 being a multi-layer photosensitive member with reference to FIGS. 1A to 1C. FIGS. 1A to 1C are each a partial cross-sectional view illustrating an example of the photosensitive member 1 (multi-layer photosensitive member).

As illustrated in FIG. 1A, the multi-layer photosensitive member serving as the photosensitive member 1 for example includes a conductive substrate 2 and a photosensitive layer 3. The photosensitive layer 3 includes a charge generating layer 3a and a charge transport layer 3b. That is, the multi-layer photosensitive member includes the charge generating layer 3a and the charge transport layer 3b as the photosensitive layer 3.

In order to improve abrasion resistance of the multi-layer photosensitive member, preferably, the charge generating layer 3a is provided on the conductive substrate 2 and the charge transport layer 3b is provided on the charge generating layer 3a as illustrated in FIG. 1A. However, in the multi-layer photosensitive member serving as the photosensitive member 1, the charge transport layer 3b may be provided on the conductive substrate 2 and the charge generating layer 3a may be protruded on the charge transport layer 3b as illustrated in FIG. 1B.

The multi-layer photosensitive member serving as the photosensitive member 1 may include the conductive substrate 2, the photosensitive layer 3, and an intermediate layer 4 (an undercoat layer) as illustrated in FIG. 1C. The intermediate layer 4 is disposed between the conductive substrate 2 and the photosensitive layer 3. The photosensitive layer 3 may be disposed directly on the conductive substrate 2 as illustrated in FIGS. 1A and 1B. Alternatively, the photosensitive layer 3 may be disposed on the conductive substrate 2 with the intermediate layer 4 therebetween as illustrated in FIG. 1C. Note that a protective layer 5 (see FIG. 2C) may be provided on the photosensitive layer 3.

No particular limitations are placed on the thickness of the charge generating layer 3a. Preferably, the charge generating layer 3a has a thickness of at least 0.01 μm and no greater than 5 μm, and more preferably at least 0.1 μm and no greater than 3 μm. No particular limitations are placed on the thickness of the charge transport layer 3b. Preferably, the charge transport layer 3b has a thickness of at least 2 μm and no greater than 100 μm, and more preferably at least 5 μm and no greater than 50 μm. Through the above, the photosensitive member 1 being a multi-layer photosensitive member has been described with reference to FIGS. 1A to 1C.

(Single-Layer Photosensitive Member)

Figure 2A:
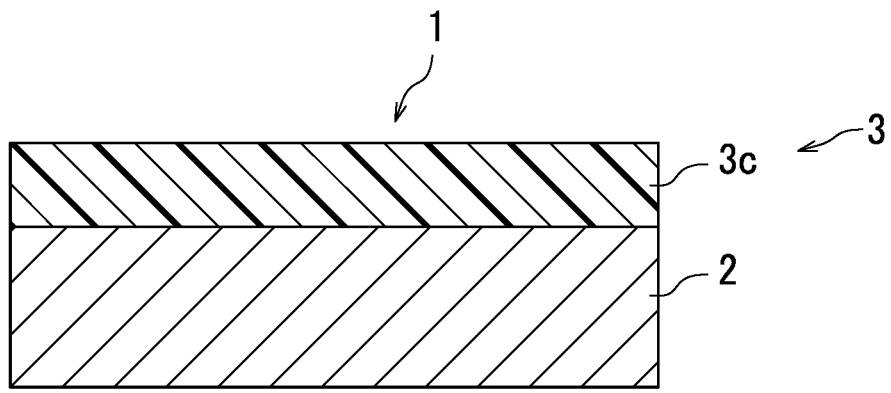
FIG. 2A is a partial cross-sectional view illustrating another example of the electrophotographic photosensitive member containing the compound according to the embodiment of the present invention.
Figure 2B:
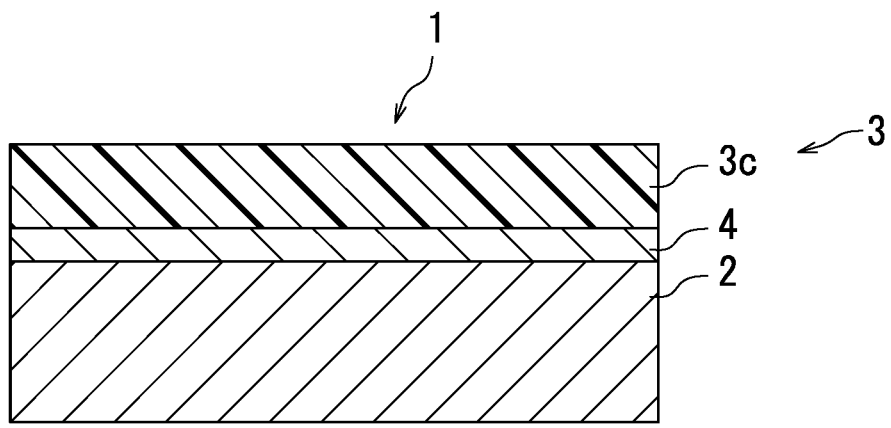
FIG. 2B is a partial cross-sectional view illustrating another example of the electrophotographic photosensitive member containing the compound according to the embodiment of the present invention.
Figure 2C:
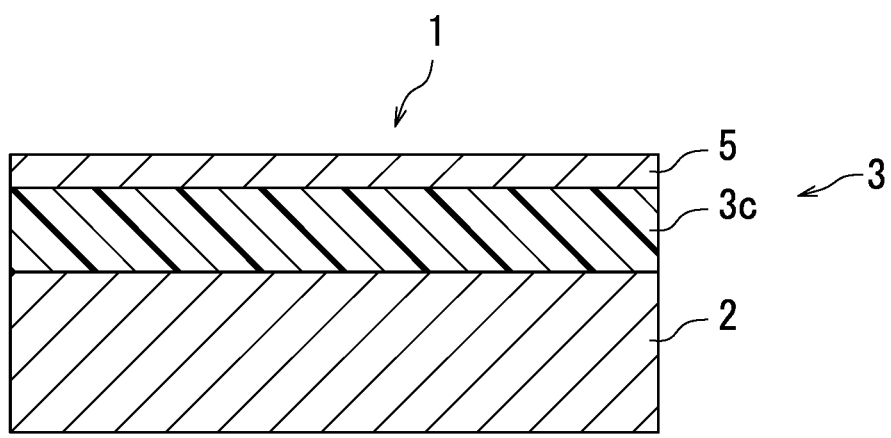
FIG. 2C is a partial cross-sectional view illustrating another example of the electrophotographic photosensitive member containing the compound according to the embodiment of the present invention.

The following describes another photosensitive member 1 being a single-layer photosensitive member with reference to FIGS. 2A to 2C. FIGS. 2A to 2C are each a partial cross-sectional view illustrating an example of the other photosensitive member 1 (single-layer photosensitive member).

As illustrated in FIG. 2A, the single-layer photosensitive member serving as the photosensitive member 1 for example includes a conductive substrate 2 and a photosensitive layer 3. The single-layer photosensitive member serving as the photosensitive member 1 includes a photosensitive layer 3 having a single layer (also referred to below as a single-layer photosensitive layer 3c).

The single-layer photosensitive member serving as the photosensitive member 1 may include the conductive substrate 2, the photosensitive layer 3c, and an intermediate layer 4 (an undercoat layer) as illustrated in FIG. 2B. The intermediate layer 4 is provided between the conductive substrate 2 and the single-layer photosensitive layer 3c. The photosensitive layer 3 may be disposed directly on the conductive substrate 2 as illustrated in FIG. 2A. Alternatively, the photosensitive layer 3 may be disposed on the conductive substrate 2 with the intermediate layer 4 therebetween as illustrated in FIG. 2B.

The single-layer photosensitive member serving as the photosensitive member 1 may include the conductive substrate 2, the single-layer photosensitive layer 3c, and a protective layer 5 as illustrated in FIG. 2C. The protective layer 5 is provided on the single-layer photosensitive layer 3c.

No particular limitations are placed on the thickness of the single-layer photosensitive layer 3c. Preferably, the single-layer photosensitive layer 3c has a thickness of at least 5 μm and no greater than 100 μm, and more preferably at least 10 μm and no greater than 50 μm. Through the above, the photosensitive member 1 being a single-layer photosensitive member has been described with reference to FIGS. 2A to 2C. The following describes the photosensitive member in further detail.

<Photosensitive Layer>

In the case of the photosensitive member being a multi-layer photosensitive member, the charge generating layer in the photosensitive layer contains a charge generating material. The charge generating layer may contain a charge generating layer binder resin (also referred to below as a base resin). The charge generating layer may contain an additive as necessary. The charge transport layer in the photosensitive layer contains a hole transport material and a binder resin. The charge transport layer may further contain an electron acceptor compound. The charge transport layer may contain an additive as necessary.

In the case of the photosensitive member being a single-layer photosensitive member, the single-layer photosensitive layer serving as the photosensitive layer contains a charge generating material, a hole transport material, and a binder resin. The single-layer photosensitive layer may further contain an electron transport material. The single-layer photosensitive layer may contain an additive as necessary.
(Hole Transport Material)

The hole transport material includes the compound (1). The photosensitive layer contains the compound (1) as the hole transport material. The compound (1) contained in the photosensitive layer can improve electrical characteristics of the photosensitive member and inhibit crystallization in the photosensitive layer. The photosensitive layer may contain one compound (1) or a plurality of different compounds (1).

Preferably, a ratio $m_{HTM}/m_{Resin}$ of mass $m_{HTM}$ of the hole transport material to mass $m_{Resin}$ of the binder resin is at least 0.50. As a result of the ratio $m_{HTM}/m_{Resin}$ being at least 0.50, one or both of sensitivity and exposure memory-inhibiting performance of the photosensitive member can be improved.

In the case of the multi-layer photosensitive member, the ratio $m_{HTM}/m_{Resin}$ is a ratio of the mass $m_{HTM}$ of the hole transport material contained in the charge transport layer to the mass man of the binder resin contained in the charge transport layer. In the case of the multi-layer photosensitive member, the ratio $m_{HTM}/m_{Resin}$ is more preferably at least 0.60, further preferably at least 0.70, and particularly preferably at least 0.80. In the case of the multi-layer photosensitive member, an upper limit of the ratio $m_{HTM}/m_{Resin}$ is for example 1.00.

In the case of the single-layer photosensitive member, the ratio $m_{HTM}/m_{Resin}$ is a ratio of the mass $m_{HTM}$ of the hole transport material contained in the single-layer photosensitive layer to the mass $m_{Resin}$ of the binder resin contained in the single-layer photosensitive layer. In the case of the single-layer photosensitive member, more preferably, the ratio $m_{HTM}m_{Resin}$ is at least 0.55. In the case of the single-layer photosensitive member, an upper limit of the ratio $m_{HTM}/m_{Resin}$ is for example 0.70.

In the case of the photosensitive layer containing only the compound (1) as the hole transport material, the mass $m_{HTM}$ of the hole transport material is the mass of the compound (1). In the case of the photosensitive layer containing a plurality of hole transport materials, the mass $m_{HTM}$ of the hole transport material is a total mass of the plurality of hole transport materials.

In the case of the photosensitive layer containing one binder resin, the mass $m_{Resin}$ of the binder resin is the mass of the one binder resin. In the case of the photosensitive layer containing a plurality of binder resins, the mass $m_{Resin}$ of the binder resin is a total mass of the plurality of binder resins.

The charge transport layer may contain only the compound (1) as the hole transport material. Alternatively, the charge transport layer may further contain, in addition to the compound (1), a hole transport material other than the compound (1) (also referred to below as an additional hole transport material).

The single-layer photosensitive layer may contain only the compound (1) as the hole transport material. Alternatively, the single-layer photosensitive layer may further contain, in addition to the compound (1), an additional hole transport material other than the compound (1).

Examples of additional hole transport materials that can be used include nitrogen-containing cyclic compounds and condensed polycyclic compounds other than the compound (1). Examples of nitrogen-containing cyclic compounds and condensed polycyclic compounds other than the compound (1) include diamine compounds (specific examples include N,N,N',N'-tetraphenylphenylenediamine derivatives, N,N,N',N'-tetraphenylnaphtylenediamine derivatives, and N,N,N',N'-tetraphenylphenanthrylenediamine derivatives), oxadiazole-based compounds (specific examples include 2,5-di(4-methylaminophenyl)-1,3,4-oxadiazole), styryl-based compounds (specific examples include 9-(4-diethylaminostyryl)anthracene), carbazole compounds (specific examples include polyvinyl carbazole), organic polysilane compounds, pyrazoline-based compounds (specific examples include 1-phenyl-3-(p-dimethylaminophenyl)pyrazoline), hydrazone compounds, indole-based compounds, oxazole-based compounds, isoxazole-based compounds, thiazole-based compounds, thiadiazole-based compounds, imidazole-based compounds, pyrazole-based compounds, and triazole-based compounds.

(Binder Resin)

Examples of binder resins that can be contained in the single-layer photosensitive layer or the charge transport layer include thermoplastic resins, thermosetting resins, and photocurable resins. Examples of thermoplastic resins include polyarylate resins, polycarbonate resins, styrene-butadiene copolymers, styrene-acrylonitrile copolymers, styrene-maleate copolymers, acrylic acid polymers, styrene-acrylate copolymers, polyethylene resins, ethylene-vinyl acetate copolymers, chlorinated polyethylene resins, polyvinyl chloride resins, polypropylene resins, ionomer resins, vinyl chloride-vinyl acetate copolymers, alkyd resins, polyamide resins, urethane resins, polysulfone resins, diallyl phthalate resins, ketone resins, polyvinyl butyral resins, polyester resins, and polyether resins. Examples of thermosetting resins include silicone resins, epoxy resins, phenolic resins, urea resins, and melamine resins. Examples of photocurable resins include acrylic acid adducts of epoxy compounds and acrylic acid adducts of urethane compounds. The single-layer photosensitive layer or the charge transport layer may contain only one of the binder resins listed above or may contain two or more of the binder resins listed above.

The binder resin preferably has a viscosity average molecular weight of at least 10,000, more preferably at least 20,000, further preferably at least 30,000, and particularly preferably at least 40,000. As a result of the viscosity average molecular weight of the binder resin being at least 10,000, the binder resin has improved abrasion resistance and the charge transport layer or the single-layer photosensitive layer is resistant to abrasion. On the other hand, the binder resin preferably has a viscosity average molecular weight of no greater than 80,000, and more preferably no greater than 70,000. As a result of the viscosity average molecular weight of the binder resin being no greater than 80,000, the binder resin is easily dissolved in a solvent for formation of the charge transport layer or in a solvent for formation of the single-layer photosensitive layer, facilitating formation of the charge transport layer and formation of the single-layer photosensitive layer.

In order to further improve electrical characteristics of the photosensitive member and further inhibit crystallization in the photosensitive layer, the binder resin is preferably a polyarylate resin or a polycarbonate resin.

(Example of Preferable Polyarylate Resin)

In order to further improve electrical characteristics of the photosensitive member and further inhibit crystallization in the photosensitive layer, the polyarylate resin is preferably a polyarylate resin including at least one repeating unit represented by general formula (10) and at least one repeating unit represented by general formula (11). The repeating units represented by general formulae (10) and (11) are also referred to below as repeating units (10) and (11), respectively.

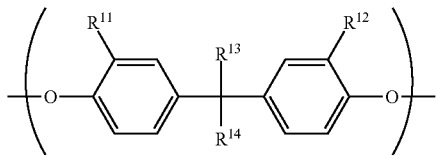
(10)

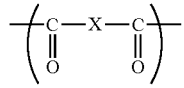
(11)

In general formula (10), $R^{11}$ and $R^{12}$ each represent, independently of one another, a hydrogen atom or a methyl group. $R^{13}$ represents a hydrogen atom or an alkyl group having a carbon number of at least 1 and no greater than 4, and $R^{14}$ represents an alkyl group having a carbon number of at least 1 and no greater than 4. Alternatively, $R^{11}$ and $R^{14}$ are bonded to one another to form a cycloalkylidene group having a carbon number of at least 5 and no greater than 14.

In the case of the polyarylate resin including one repeating unit (11), X in general formula (11) represents a divalent group represented by chemical formula (X1).

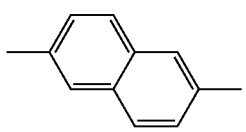
(X1)

In the case of the polyarylate resin including a plurality of different repeating units (11). X in general formula (11) represents a divalent group represented by chemical formula (X1), (X2), (X3), (X4), (X5), or (X6). X in general formula (11) representing one of the plurality of different repeating units (11) represents a divalent group represented by chemical formula (X1). X in general formula (11) representing another one of the plurality of different repeating units (11) represents a divalent group represented by chemical formula (X2), (X3), (X4), (X5), or (X6).

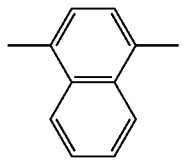
(X2)

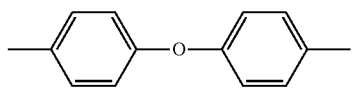
(X3)

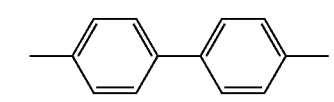
(X4)

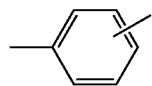
(X5)

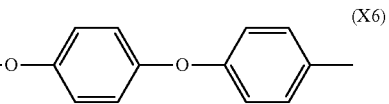
(X6)

(Repeating Unit (10))

The following describes the repeating unit (10). In general formula (10), the alkyl group having a carbon number of at least 1 and no greater than 4 that may be represented by $R^{13}$ and $R^{11}$ is preferably a methyl group or an ethyl group.

In general formula (10), the cycloalkylidene group having a carbon number of at least 5 and no greater than 14 that may be represented by $R^{11}$ and $R^{14}$ bonded to one another is preferably a cycloalkylidene group having a carbon number of at least 5 and no greater than 12, more preferably a cyclopentylidene group, a cyclohexylidene group, or a cyclododecylidene group, and further preferably a cyclohexylidene group or a cyclododecylidene group.

Examples of preferable repeating units (10) include repeating units represented by chemical formulae (10-1), (10-2), and (10-3). The repeating units represented by chemical formulae (10-1), (10-2), and (10-3) are also referred to below as repeating units (10-1), (10-2), and (10-3), respectively.

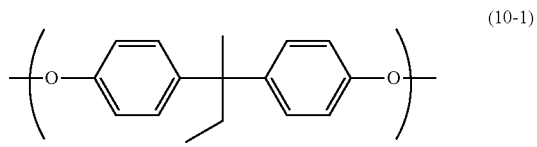
(10-1)

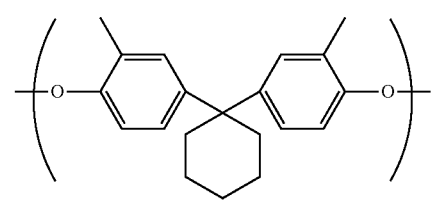
(10-2)

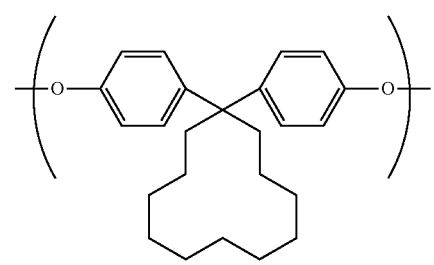
(10-3)

The polyarylate resin may include, as the repeating unit (10), one repeating unit (10) or a plurality of (for example, two or three) different repeating units (10).

The following describes the repeating unit (11) with respect to a case where one repeating unit (11) is included in the polyarylate resin and with respect to a case where a plurality of different repeating units (11) are included in the polyarylate resin.

(Case where One Repeating Unit (11) is Included)

In the case where one repeating unit (11) is included in the polyarylate resin, X in general formula (11) represents a divalent group represented by chemical formula (X1). In this case, the polyarylate resin includes at least one repeating unit (10) and one repeating unit represented by chemical formula (11-X1) (also referred to below as a repeating unit (11-X1)). In this case, the polyarylate resin preferably includes one repeating unit (10) and one repeating unit (11-X1).

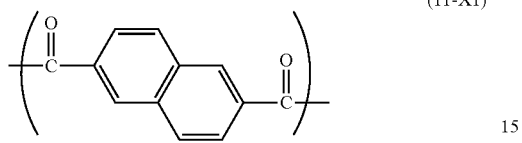
(11-X1)

(Case where Plurality of Different Repeating Units (11) are Included)

In the case where a plurality of different repeating units (11) are included in the polyarylate resin, X in general formula (11) represents a divalent group represented by chemical formula (X1), (X2), (X3), (X4), (X5), or (X6). X in general formula (11) representing one of the plurality of different repeating units (11) represents a divalent group represented by chemical formula (X1). In this case, the polyarylate resin includes at least one repeating unit (10), one repeating unit (11-X1), and at least one repeating unit represented by general formula (11') (also referred to below as a repeating unit (11')). In this case, the polyarylate resin preferably includes one repeating unit (10), one repeating unit (11-X1), and one repeating unit (11').

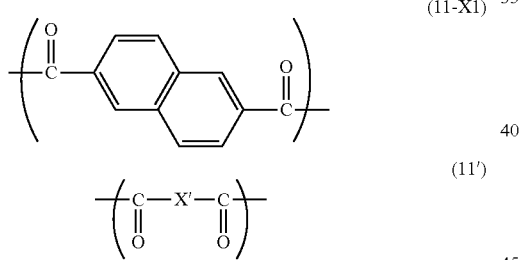
(11-X1)

(11')

X' in general formula (11') represents a divalent group represented by chemical formula (X2), (X3), (X4), (X5), or (X6). Preferably, X' represents a divalent group represented by chemical formula (X2) or (X3).

Examples of repeating units (11') include repeating units represented by chemical formulae (11-X2), (11-X3), (11-X4), (11-X5), and (11-X6) (also referred to below as repeating units (11-X2), (11-X3), (11-X4), (11-X5), and (11-X6), respectively). Preferably, the repeating unit (11') is the repeating unit (11-X2) or (11-X3).

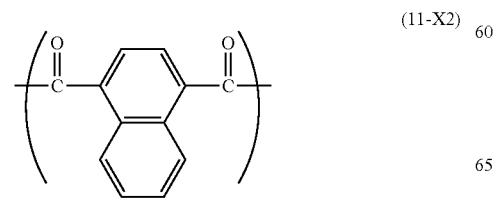
(11-X2)

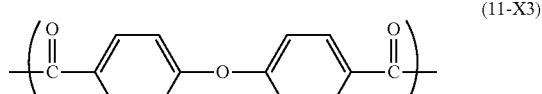
(11-X3)

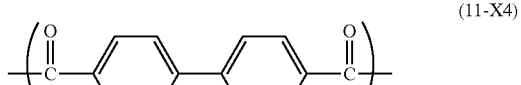
(11-X4)

(11-X5)

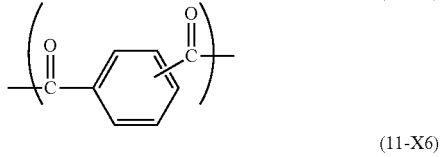
(11-X6)

In order to improve electrical characteristics of the photosensitive member and inhibit crystallization in the photosensitive layer, the polyarylate resin preferably includes a plurality of different repeating units (11), more preferably includes at least two and no greater than eight different repeating units (11), further preferably includes two or three different repeating units (11), and particularly preferably includes two different repeating units (11).

In order to improve electrical characteristics of the photosensitive member and inhibit crystallization in the photosensitive layer, a ratio (also referred to below as a ratio p) of the repeating number of the repeating unit (11-X1) to a sum of the repeating number of the repeating unit (11-X1) and the repeating number of the repeating unit (11') is preferably at least 0.10 and no greater than 0.90, more preferably at least 0.20 and no greater than 0.80, further preferably at least 0.30 and no greater than 0.70, still further preferably at least 0.40 and no greater than 0.60, and particularly preferably 0.50. The ratio p is not a value obtained from one molecular chain but an average of values obtained from all molecular chains (a plurality of molecular chains) of the polyarylate resin contained in the photosensitive layer. The ratio p can be calculated from a $^1$H-NMR spectrum of the polyarylate resin measured using a proton nuclear magnetic resonance spectrometer.

Examples of preferable polyarylate resins including at least one repeating unit (10) and at least one repeating unit (11) include a polyarylate resin including the repeating unit (10-1), the repeating unit (11-X1), and the repeating unit (11-X3); a polyarylate resin including the repeating unit (10-2), the repeating unit (11-X1), and the repeating unit (11-X3); a polyarylate resin including the repeating unit (10-2), the repeating unit (11-X1), and the repeating unit (11-X2); and a polyarylate resin including the repeating unit (10-3), the repeating unit (11-X1), and the repeating unit (11-X3).

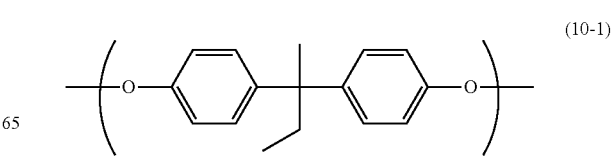
(10-1)

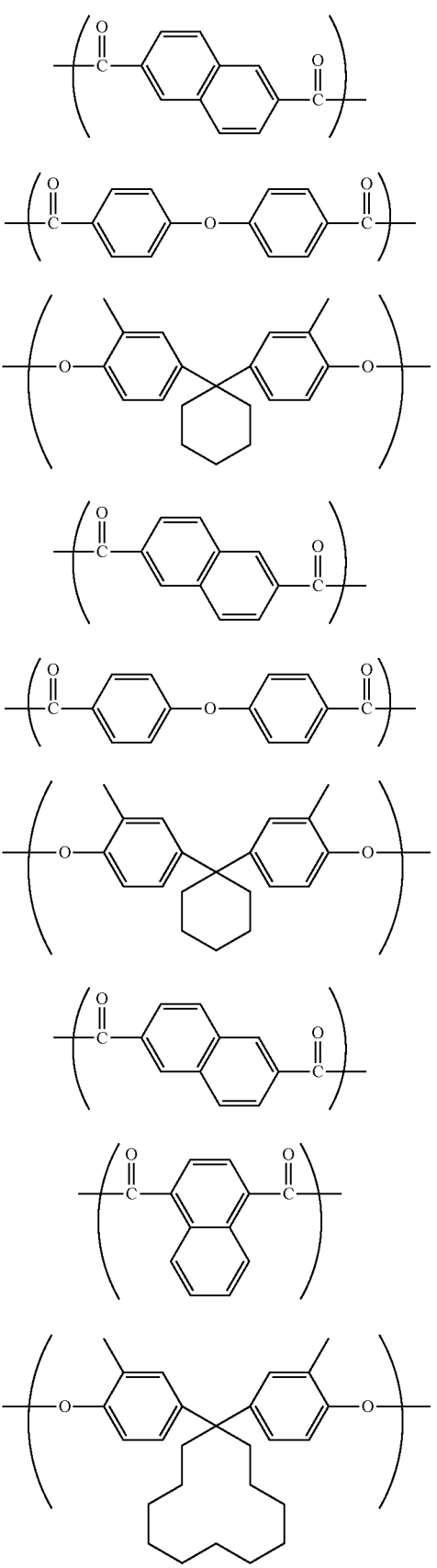

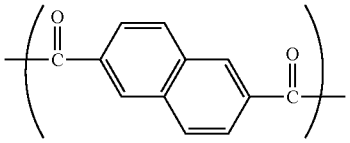

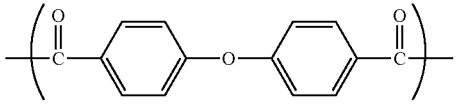

In the polyarylate resin, a repeating unit derived from an aromatic diol and a repeating unit derived from an aromatic dicarboxylic acid are adjacent to and bonded to one another. In the case of the polyarylate resin being a copolymer, the polyarylate resin may for example be a random copolymer, an alternating copolymer, a periodic copolymer, or a block copolymer.

The repeating unit derived from an aromatic diol is for example the repeating unit (10). In the case of the polyarylate resin including a plurality of different repeating units (10), no particular limitations are placed on the sequence of the different repeating units (10). One repeating unit (10) and another repeating unit (10) may be in a random sequence, in an alternating sequence, in a periodic sequence, or in a block sequence with the repeating unit (11) therebetween. The repeating unit derived from an aromatic dicarboxylic acid is for example the repeating unit (11). In the case of the polyarylate resin including a plurality of different repeating units (11), no particular limitations are placed on the sequence of the different repeating units (11). One repeating unit (11) and another repeating unit (11) may be in a random sequence, in an alternating sequence, in a periodic sequence, or in a block sequence with the repeating unit (10) therebetween.

The polyarylate resin may include only the repeating units (10) and (11) as repeating units thereof. The polyarylate resin may further include, in addition to the repeating units (10) and (11), a repeating unit other than the repeating units (10) and (11).

The photosensitive layer may contain, as the binder resin, only one polyarylate resin including at least one repeating unit (10) and at least one repeating unit (11). Alternatively, the photosensitive layer may contain, as the binder resin, a plurality of such polyarylate resins. The photosensitive layer may further contain, as the binder resin, another binder resin in addition to the polyarylate resin including at least one repeating unit (10) and at least one repeating unit (11).

No particular limitations are placed on the production method of the polyarylate resin. Examples of production methods of the polyarylate resin include a method involving polycondensation of an aromatic diol for forming a repeating unit and an aromatic dicarboxylic acid for forming a repeating unit. Any known synthesis method (specific examples include solution polymerization, melt polymerization, and interfacial polymerization) can be employed as a polycondensation method.

The aromatic diol for forming a repeating unit is for example at least one compound represented by general formula (BP-10). The aromatic dicarboxylic acid for forming a repeating unit is for example at least one compound represented by general formula (DC-11), $R^{11}$, $R^{12}$, $R^{13}$, $R^{14}$, and X in general formulae (BP-10) and (DC-11) are respectively the same as defined for $R^{11}$, $R^{12}$, $R^{13}$, $R^{14}$, and X in general formulae (10) and (11). The compounds represented by general formulae (BP-10) and (DC-11) are also referred to below as compounds (BP-10) and (DC-11), respectively.

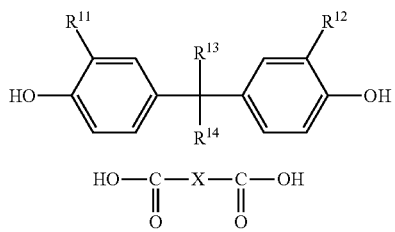

(BP-10)

(DC-11)

Examples of preferable compounds (BP-10) include compounds represented by chemical formulae (BP-10-1) to (BP-10-3) (also referred to below as compounds (BP-10-1) to (BP-10-3), respectively).

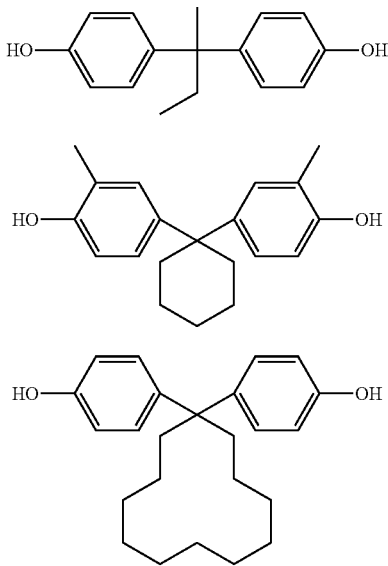

(BP-10-1)

(BP-10-2)

(BP-10-3)

Examples of preferable compounds (DC-11) include compounds represented by chemical formulae (DC-11-X1) to (DC-11-X6) (also referred to below as compounds (DC-11-X1) to (DC-11-X6), respectively).

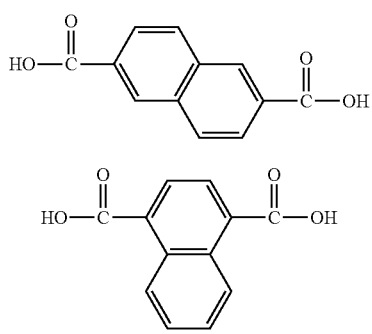

(DC-11-X1)

(DC-11-X2)

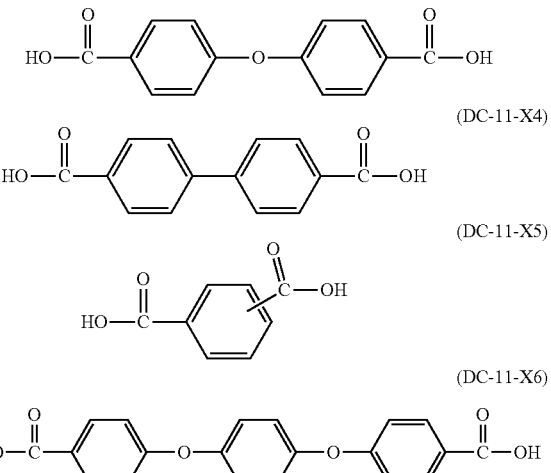

(DC-11-X3)

(DC-11-X4)

(DC-11-X5)

(DC-11-X6)

The aromatic diol (for example, the compound (BP-10)) for forming a repeating unit may be used in the form of an aromatic diacetate. The aromatic dicarboxylic acid (for example, the compound (DC-11)) for forming a repeating unit may be used in the form of a derivative thereof. Examples of derivatives of the aromatic dicarboxylic acid include an aromatic dicarboxylic acid dichloride, an aromatic dicarboxylic acid dimethyl ester, an aromatic dicarboxylic acid diethyl ester, and an aromatic dicarboxylic acid anhydride. The aromatic dicarboxylic acid dichloride is a compound obtained through substitution of two chemical groups "—C(=O)—OH" of the aromatic dicarboxylic acid each with a chemical group "—C(=O)—Cl".

Either or both of a base and a catalyst may be added in polycondensation of the aromatic diol and the aromatic dicarboxylic acid. The base and the catalyst may be selected as appropriate from among known bases and known catalysts. Examples of bases include sodium hydroxide. Examples of catalysts include benzyltributylammonium chloride, ammonium chloride, ammonium bromide, quaternary ammonium salt, triethylamine, and trimethylamine. Through the above, the polyarylate resin has been described.

(Another Example of Preferable Polyarylate Resin)

In order to further improve electrical characteristics of the photosensitive member and further inhibit crystallization in the photosensitive layer, the polyarylate resin is preferably a polyarylate resin including the repeating unit (10-1), a repeating unit represented by chemical formula (12-1) shown below, and the repeating unit (11-X3). The repeating unit represented by chemical formula (12-1) is also referred to below as a repeating unit (12-1).

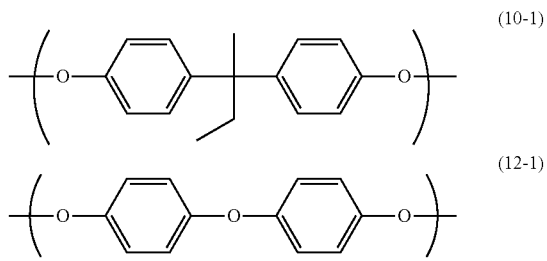

(10-1)

(12-1)

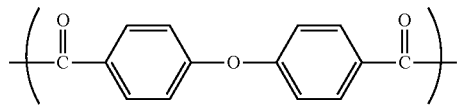

In order to improve electrical characteristics of the photosensitive member and inhibit crystallization in the photosensitive layer, a ratio (also referred to below as a ratio q) of the repeating number of the repeating unit (10-1) to a sum of the repeating number of the repeating unit (10-1) and the repeating number of the repeating unit (12-1) is preferably at least 0.10 and less than 1.00, more preferably at least 0.30 and no greater than 0.95, further preferably at least 0.50 and no greater than 0.95, still further preferably at least 0.70 and no greater than 0.95, and particularly preferably 0.80. The ratio q is not a value obtained from one molecular chain but an average of values obtained from all molecular chains (a plurality of molecular chains) of the polyarylate resin contained in the photosensitive layer. The ratio q can be calculated according to the same method as for the ratio p.

The polyarylate resin including the repeating units (10-1), (12-1), and (11-X3) may for example be a random copolymer, an alternating copolymer, a periodic copolymer, or a block copolymer. The polyarylate resin may include only the repeating units (10-1), (12-1), and (11-X3) or may further include a repeating unit other than these repeating units. The photosensitive layer may contain, as the binder resin, only the polyarylate resin including the repeating units (10-1), (12-1), and (11-X3) or may further contain a binder resin other than such a polyarylate resin.

No particular limitations are placed on the production method of the polyarylate resin. Examples of production methods of the polyarylate resin include a method involving polycondensation of the compound (BP-10-1), a compound represented by chemical formula (BP-12-1) shown below, and the compound (DC-11-X3). The compound represented by chemical formula (BP-12-1) is also referred to below as a compound (BP-12-1).

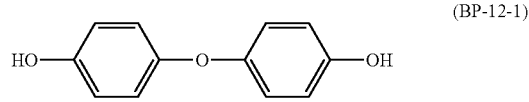 [SMILES: Oc1ccc(Oc2ccc(O)cc2)cc1]

(Example of Preferable Polycarbonate Resin)

In order to further improve electrical characteristics of the photosensitive member and further inhibit crystallization in the photosensitive layer, the polycarbonate resin is preferably a polycarbonate resin including a repeating unit represented by chemical formula (R-5), (R-6), or (R-7). The repeating units represented by chemical formulae (R-5), (R-6), and (R-7) are also referred to below as repeating units (R-5), (R-6), and (R-7), respectively.

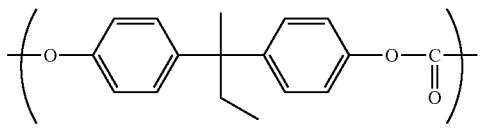

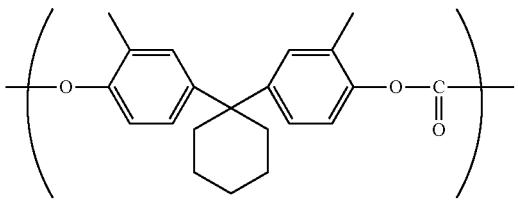

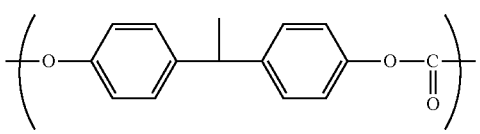

In order to improve electrical characteristics of the photosensitive member and inhibit crystallization in the photosensitive layer, preferably, the polycarbonate resin is for example a polycarbonate resin including the repeating unit (R-5) or a polycarbonate resin including the repeating unit (R-6).

The photosensitive layer may contain, as the binder resin, only one polycarbonate resin including the repeating unit (R-5), (R-6), or (R-7). Alternatively, the photosensitive layer may contain, as the binder resin, a plurality of such polycarbonate resins. Moreover, the photosensitive layer may further contain, as the binder resin, another binder resin in addition to the polycarbonate resin including the repeating unit (R-5), (R-6), or (R-7). Through the above, the polycarbonate resin has been described.

(Base Resin)

In the case of the photosensitive member being a multilayer photosensitive member, the charge generating layer contains a base resin. Examples of base resins include thermoplastic resins, thermosetting resins, and photocurable resins. Examples of thermoplastic resins include polyarylate resins, polycarbonate resins, styrene-butadiene copolymers, styrene-acrylonitrile copolymers, styrene-maleate copolymers, acrylic acid polymers, styrene-acrylate copolymers, polyethylene resins, ethylene-vinyl acetate copolymers, chlorinated polyethylene resins, polyvinyl chloride resins, polypropylene resins, ionomer resins, vinyl chloride-vinyl acetate copolymers, alkyd resins, polyamide resins, urethane resins, polysulfone resins, diallyl phthalate resins, ketone resins, polyvinyl butyral resins, polyester resins, and polyether resins. Examples of thermosetting resins include silicone resins, epoxy resins, phenolic resins, urea resins, and melamine resins. Examples of photocurable resins include acrylic acid adducts of epoxy compounds and acrylic acid adducts of urethane compounds. The charge generating layer may contain only one of the base resins listed above or may contain two or more of the base resins listed above. In order to favorably form the charge generating layer and the charge transport layer, preferably, the base resin contained in the charge generating layer is different from the binder resin contained in the charge transport layer.

(Electron Acceptor Compound)

In the case of the photosensitive member being a multilayer photosensitive member, the charge transport layer preferably contains an electron acceptor compound. The electron acceptor compound is expected to form a complex with the compound (1), and the resultant complex is expected to be favorably dissolved in the solvent for formation of the charge transport layer. This facilitates formation of a uniform charge transport layer, further improving electrical characteristics of the multi-layer photosensitive member and further inhibiting crystallization in the charge transport layer.

Preferably, a ratio $m_{EA}/m_{HTM}$ of mass $m_{EA}$ of the electron acceptor compound to the mass $m_{HTM}$ of the hole transport material is at least 0.01 and no greater than 0.50. As a result of the ratio $m_{EA}/m_{HTM}$ being at least 0.01 and no greater than 0.50, it is possible to further improve sensitivity of the photosensitive member while inhibiting crystallization in the photosensitive layer. In order to further improve sensitivity of the photosensitive member while inhibiting crystallization in the photosensitive layer, the ratio $m_{EA}/m_{HTM}$ is more preferably at least 0.05, and further preferably at least 0.08. In order to further improve sensitivity of the photosensitive member while inhibiting crystallization in the photosensitive layer, the ratio $m_{EA}/m_{HTM}$ is more preferably no greater than 0.20, and further preferably no greater than 0.10. Note that in the case of the charge transport layer containing a plurality of electron acceptor compounds, the mass m of the electron acceptor compound is a total mass of the plurality of electron acceptor compounds. In the case of the charge transport layer containing a plurality of hole transport materials, the mass $m_{HTM}$ of the hole transport material is a total mass of the plurality of hole transport materials.

Examples of electron acceptor compounds include quinone-based compounds, diimide-based compounds, hydrazone-based compounds, malononitrile-based compounds, thiopyran-based compounds, trinitrothioxanthone-based compounds, 3,4,5,7-tetranitro-9-fluorenone-based compounds, dinitroanthracene-based compounds, dinitroacridine-based compounds, tetracyanoethylene, 2,4,8-trinitrothioxanthone, dinitrobenzene, dinitroacridine, succinic anhydride, maleic anhydride, and dibromomaleic anhydride. Examples of quinone-based compounds include diphenoquinone-based compounds, azoquinone-based compounds, anthraquinone-based compounds, naphthoquinone-based compounds, nitroanthraquinone-based compounds, and dinitroanthraquinone-based compounds. The charge transport layer may contain one electron acceptor compound or may contain a plurality of electron acceptor compounds.

Examples of preferable electron acceptor compounds include compounds represented by general formulae (20), (21), (22), (23), and (24) (also referred to below as compounds (20), (21), (22), (23), and (24), respectively). The electron acceptor being the compound (20), (21), (22), (23), or (24) tends to favorably form a complex with the compound (1). The resultant complex is therefore expected to be favorably dissolved in the solvent for formation of the charge transport layer. This facilitates formation of a uniform charge transport layer, further improving electrical characteristics of the multi-layer photosensitive member and further inhibiting crystallization in the charge transport layer.

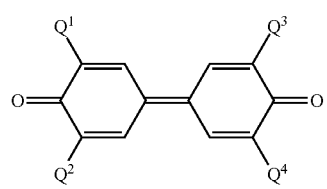

(20)

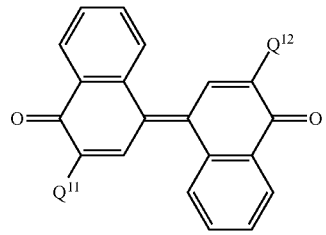

(21)

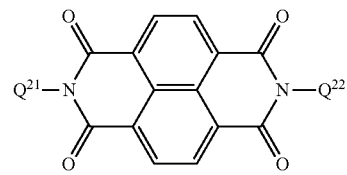

(22)

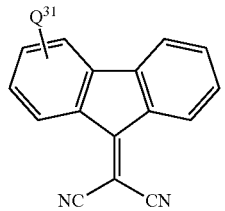

(23)

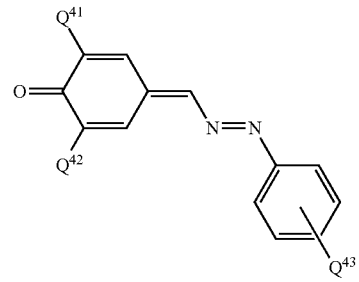

(24)

In general formula (20), $Q^1$, $Q^2$, $Q^3$, and $Q^4$ each represent, independently of one another, an alkyl group having a carbon number of at least 1 and no greater than 6, an alkoxy group having a carbon number of at least 1 and no greater than 6, a cycloalkyl group having a carbon number of at least 5 and no greater than 7, or an aryl group having a carbon number of at least 6 and no greater than 14. In general formula (21). $Q^{11}$ and $Q^{12}$ each represent, independently of one another, an alkyl group having a carbon number of at least 1 and no greater than 6, an alkoxy group having a carbon number of at least 1 and no greater than 6, a cycloalkyl group having a carbon number of at least 5 and no greater than 7, or an aryl group having a carbon number of at least 6 and no greater than 14. In general formula (22). $Q^{21}$ and $Q^{22}$ each represent, independently of one another, an aryl group having a carbon number of at least 6 and no greater than 14 and optionally having an alkyl group having a carbon number of at least 1 and no greater than 6 or an alkoxy group having a carbon number of at least 1 and no greater than 6. In general formula (23). $Q^{31}$ represents an alkoxycarbonyl group having a carbon number of at least 2 and no greater than 7. In general formula (24), $Q^{41}$ and $Q^{42}$ each represent, independently of one another, an alkyl group having a carbon number of at least 1 and no greater than 6, and $Q^{43}$ represents a halogen atom.

The alkyl group having a carbon number of at least 1 and no greater than 6 that may be represented by $Q^1$, $Q^2$, $Q^3$, and $Q^4$ in general formula (20), $Q^{11}$ and $Q^{12}$ in general formula (21), and $Q^{41}$ and $Q^{42}$ in general formula (24) is preferably a methyl group, an ethyl group, a butyl, or a hexyl group, and more preferably a methyl group, a tert-butyl group or a 1-ethyl-1-methylpropyl group.

The alkoxy group having a carbon number of at least 1 and no greater than 6 that may be represented by $Q^1$, $Q^2$, $Q^3$, and $Q^4$ in general formula (20), and $Q^{11}$ and $Q^{12}$ in general formula (21) is preferably an alkoxy group having a carbon number of at least 1 and no greater than 3.

The cycloalkyl group having a carbon number of at least 5 and no greater than 7 that may be represented by $Q^1$, $Q^2$, $Q^3$, and $Q^4$ in general formula (20), and $Q^{11}$ and $Q^{12}$ in general formula (21) is preferably a cyclohexyl group.

The aryl group having a carbon number of at least 6 and no greater than 14 that may be represented by $Q^1$, $Q^2$, $Q^3$, and $Q^4$ in general formula (20), $Q^{11}$ and $Q^{12}$ in general formula (21), and $Q^{21}$ and $Q^{22}$ in general formula (22) is preferably an aryl group having a carbon number of at least 6 and no greater than 10, and more preferably a phenyl group.

The aryl group having a carbon number of at least 6 and no greater than 14 that may be represented by $Q^{21}$ and $Q^{22}$ in general formula (22) may optionally have, as a substituent, an alkyl group having a carbon number of at least 1 and no greater than 6 or an alkoxy group having a carbon number of at least 1 and no greater than 6. Such a substituent is preferably an alkyl group having a carbon number of at least 1 and no greater than 6, more preferably an alkyl group having a carbon number of at least 1 and no greater than 3, and further preferably a methyl group or an ethyl group. The number of substituents (specifically, the alkyl group having a carbon number of at least 1 and no greater than 6 or the alkoxy group having a carbon number of at least 1 and no greater than 6) of the aryl group having a carbon number of at least 6 and no greater than 14 that may be represented by $Q^{21}$ and $Q^{22}$ is preferably at least 1 and no greater than 3, and more preferably 2.

The alkoxycarbonyl group having a carbon number of at least 2 and no greater than 7 that may be represented by $Q^{31}$ in general formula (23) is preferably a butoxycarbonyl group, and more preferably an n-butoxycarbonyl group.

The halogen atom that may be represented by $Q^{41}$ in general formula (24) is preferably a chlorine atom or a fluorine atom, and more preferably a chlorine atom.

Preferably, $Q^1$, $Q^2$, $Q^3$, and $Q^4$ in general formula (20) each represent, independently of one another, an alkyl group having a carbon number of at least 1 and no greater than 6. Preferably, $Q^{11}$ and $Q^{12}$ in general formula (21) each represent, independently of one another, an alkyl group having a carbon number of at least 1 and no greater than 6. Preferably, $Q^{21}$ and $Q^{22}$ in general formula general (22) each represent, independently of one another, an aryl group having a carbon number of at least 6 and no greater than 14 and having an alkyl group having a carbon number of at least 1 and no greater than 6. Preferably, $Q^{31}$ in general formula (23) represents an alkoxycarbonyl group having a carbon number of at least 2 and no greater than 6. Preferably, in general formula (24), $Q^{41}$ and $Q^{42}$ each represent, independently of one another, an alkyl group having a carbon number of at least 1 and no greater than 4, and $Q^{41}$ represents a chlorine atom.

Examples of preferable electron acceptor compounds include compounds represented by chemical formulae (20-E1), (20-E2), (21-E3), (22-E4), (23-E5), and (24-E6) (also referred to below as compounds (20-E1), (20-E2), (21-E3), (22-E4), (23-E5), and (24-E6), respectively). Examples of preferable compounds (20) include the compounds (20-E1) and (20-E2). Examples of preferable compounds (21) include the compound (21-E3). Examples of preferable compounds (22) include the compound (22-E4). Examples of preferable compounds (23) include the compound (23-E5). Examples of preferable compounds (24) include the compound (24-E6).

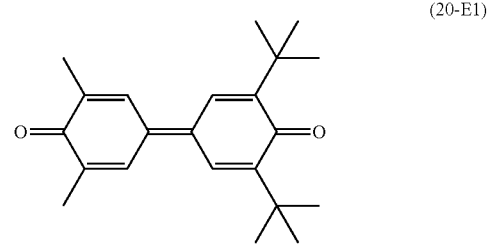

(20-E1)

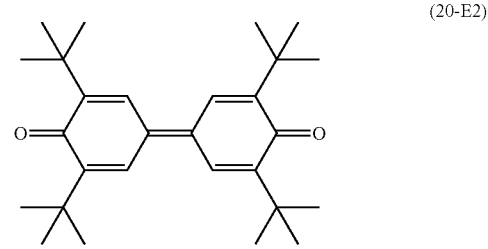

(20-E2)

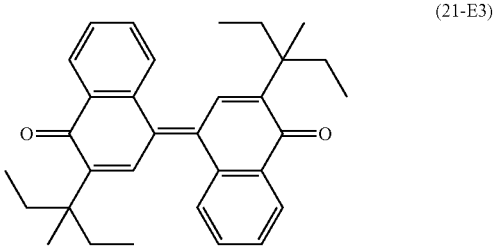

(21-E3)

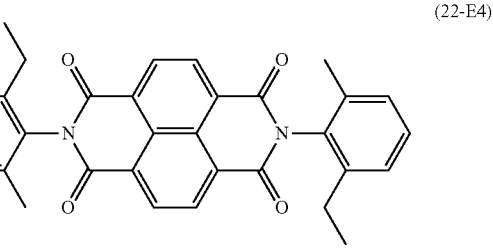

(22-E4)

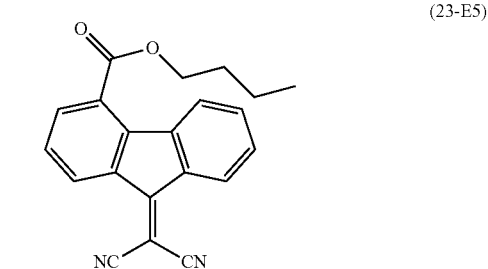

(23-E5)

-continued

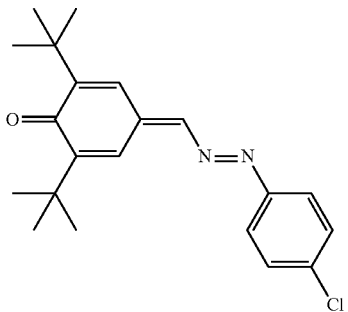

(24-E6)

The photosensitive layer may contain, as the electron acceptor compound, only one of the compounds (20), (21), (22), (23), and (24) or may contain two or more of these compounds. The photosensitive layer may contain, in addition to any of the compounds (20) to (24), an electron acceptor compound other than the compounds (20) to (24).

The photosensitive layer may contain, as the electron acceptor compound, only one of the compounds (20-E1), (20-E2), (21-E3), (22-E4), (23-E5), and (24-E6) or may contain two or more of these compounds. The photosensitive layer may further contain another electron acceptor compound in addition to any of the compounds (20-E1), (20-E2), (21-E3), (22-E4), (23-E5), and (24-E6).

(Electron Transport Material)

In the case of the photosensitive member being a single-layer photosensitive member, the single-layer photosensitive layer preferably contains an electron transport material. As a result of the single-layer photosensitive layer containing an electron transport material, it is possible to improve sensitivity and exposure memory-inhibiting performance of the photosensitive member while inhibiting crystallization in the photosensitive layer. The electron transport material is expected to form a complex with the compound (1), and the resultant complex is expected to be favorably dissolved in the solvent for formation of the single-layer photosensitive layer. This facilitates formation of a uniform single-layer photosensitive layer, further improving electrical characteristics of the single-layer photosensitive member and further inhibiting crystallization in the single-layer photosensitive layer.

Preferably, a ratio $m_{ETM}/m_{HTM}$ of mass $m_{ETM}$ of the electron transport material to the mass $m_{HTM}$ of the hole transport material is at least 0.01 and no greater than 1.50. As a result of the ratio $m_{ETM}/m_{HTM}$ HTM being at least 0.01, it is possible to further improve sensitivity and exposure memory-inhibiting performance of the photosensitive member. As a result of the ratio $m_{ETM}/m_{HTM}$ being no greater than 1.50, it is possible to further improve sensitivity and exposure memory-inhibiting performance of the photosensitive member, and further inhibit crystallization in the photosensitive layer. In order to further improve sensitivity of the photosensitive member while inhibiting crystallization in the photosensitive layer, the ratio $m_{ETM}/m_{HTM}$ is more preferably at least 0.40, further preferably at least 0.50, and still further preferably at least 0.60. In order to further improve sensitivity and exposure memory-inhibiting performance of the photosensitive member while inhibiting crystallization in the photosensitive layer, the ratio $m_{ETM}/m_{HTM}$ is more preferably no greater than 1.00, and further preferably no greater than 0.70. Note that in the case of the single-layer photosensitive layer containing a plurality of electron transport materials, the mass $m_{ETM}$ of the electron transport material is a total mass of the plurality of electron transport materials. In the case of the single-layer photosensitive layer containing a plurality of hole transport materials, the mass $m_{HTM}$ of the hole transport material is a total mass of the plurality of hole transport materials.

Examples of preferable electron transport materials are the same as the examples of preferable electron acceptor compounds. The electron transport material being the compound (20), (21), (22), (23), or (24) tends to favorably form a complex with the compound (1). The resultant complex is therefore expected to be favorably dissolved in the solvent for formation of the single-layer photosensitive layer. This facilitates formation of a uniform single-layer photosensitive layer, further improving electrical characteristics of the single-layer photosensitive member and further inhibiting crystallization in the single-layer photosensitive layer.

The photosensitive layer may contain one electron transport material or may contain a plurality of electron transport materials. The photosensitive layer may contain, as the electron transport material, only one of the compounds (20), (21), (22), (23), and (24) or may contain two or more of these compounds. The photosensitive layer may contain, in addition to any of the compounds (20) to (24), an electron transport material other than the compounds (20) to (24). The photosensitive layer may contain, as the electron transport material, only one of the compounds (20-E1), (20-E2), (21-E3), (22-E4), (23-E5), and (24-E6) or may contain two or more of these compounds. The photosensitive layer may contain another electron transport material in addition to any of the compounds (20-E1), (20-E2), (21-E3), (22-E4), (23-E5), and (24-E6).

(Charge Generating Material)

Examples of charge generating materials include phthalocyanine-based pigments, perylene-based pigments, bisazo pigments, tris-azo pigments, dithioketopyrrolopyrrole pigments, metal-free naphthalocyanine pigments, metal naphthalocyanine pigments, squaraine pigments, indigo pigments, azulenium pigments, cyanine pigments, powders of inorganic photoconductive materials (examples include selenium, selenium-tellurium, selenium-arsenic, cadmium sulfide, and amorphous silicon), pyrylium pigments, anthanthrone-based pigments, triphenylmethane-based pigments, threne-based pigments, toluidine-based pigments, pyrazoline-based pigments, and quinacridone-based pigments. The photosensitive layer may contain only one of the charge generating materials listed above or may contain two or more of the charge generating materials listed above.

Examples of phthalocyanine-based pigments include metal-free phthalocyanine and metal phthalocyanine. Examples of metal phthalocyanine include titanyl phthalocyanine, hydroxygallium phthaloyvanine, and chlorogallium phthalocyanine. Metal-free phthalocyanine is represented by chemical formula (CGM-1). Titanyl phthalocyanine is represented by chemical formula (CGM-2).

(CGM-1)
(CGM-2)

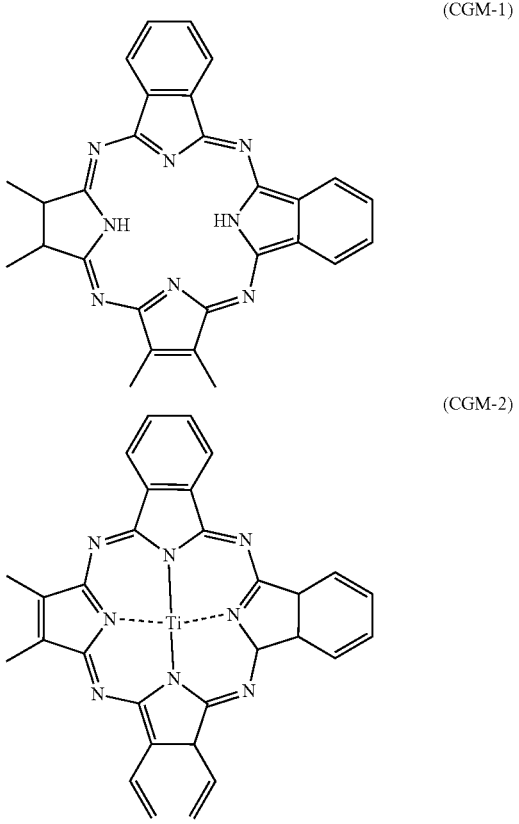

The phthalocyanine-based pigments may be crystalline or non-crystalline. An example of crystalline metal-free phthalocyanine is metal-free phthalocyanine having an X-form crystal structure (also referred to below as X-form metal-free phthalocyanine). Examples of crystalline titanyl phtha-loyvanine include titanyl phthalocyanine having an α-form crystal structure, titanyl phthalocyanine having a β-form crystal structure, and titanyl phthalocyanine having a Y-form crystal structure (also referred to below as α-form titanyl phthalocyanine, β-form titanyl phthalocyanine, and Y-form titanyl phthalocyanine, respectively).

In a digital optical image forming apparatus (for example, a laser beam printer or facsimile machine that uses a light source such as a semiconductor laser), for example, a photosensitive member that is sensitive to a region of wavelengths of at least 700 nm is preferably used. Preferably, the charge generating material is a phthalocyanine-based pigment as offering high quantum yield in the region of wavelengths of at least 700 nm, more preferably metal-free phthalocyanine or titanyl phthalocyanine, further preferably X-form metal-free phthalocyanine or Y-form titanyl phthalocyanine, and particularly preferably Y-form titanyl phthalocyanine.

A photosensitive member included in an image forming apparatus that uses a short-wavelength laser light source (for example, a laser light source having a wavelength of at least 350 nm and no greater than 550 nm) preferably contains an anthanthrone-based pigment as a charge generating material.

The charge generating material is preferably contained in an amount of at least 0.1 parts by mass and no greater than 50 parts by mass relative to 100 parts by mass of the binder resin in the photosensitive layer, more preferably in an amount of at least 0.5 parts by mass and no greater than 30 parts by mass, and particularly preferably in an amount of at least 0.5 parts by mass and no greater than 4.5 parts by mass.

(Additive)

Examples of additives include antidegradants (specific examples include antioxidants, radical scavengers, singlet quenchers, and ultraviolet absorbing agents), softeners, surface modifiers, extenders, thickeners, dispersion stabilizers, waxes, donors, surfactants, plasticizers, sensitizers, and leveling agents. Examples of antioxidants include hindered phenols (specific examples include di(tert-butyl)p-cresol), hindered amines, paraphenylenediamines, arylalkanes, hydroquinones, spirochromanes, spiroindanones, and derivatives of the aforementioned materials. Other examples of antioxidants include organosulfur compounds and organophosphorus compounds. Examples of leveling agents include dimethyl silicone oil. Examples of sensitizers include meta-terphenyl.

(Combinations of Materials)

In order to further improve electrical characteristics of the photosensitive member being a multi-layer photosensitive member and further inhibit crystallization in the photosensitive layer, preferably, the hole transport material, the binder resin, and the electron acceptor compound are in any of the following combinations. More preferably, the hole transport material, the binder resin, and the electron acceptor compound are in any of the following combinations and the charge generating material is Y-form titanyl phthalocyanine.

The hole transport material is the compound (1-1), the binder resin is the polyarylate resin including the repeating units (10-1), (11-X1), and (11-X3), and the electron acceptor compound is the compound (20-E1), (20-E2), (21-E3), (22-E4), (23-E5), or (24-E6).

Alternatively, the hole transport material is the compound (1-2), the binder resin is the polyarylate resin including the repeating units (10-1), (11-X1), and (11-X3), and the electron acceptor compound is the compound (20-E1), (20-E2), (21-E3), (22-E4), (23-E5), or (24-E6).

Alternatively, the hole transport material is the compound (1-3), the binder resin is the polyarylate resin including the repeating units (10-1), (11-X1), and (11-X3), and the electron acceptor compound is the compound (20-E1), (20-E2), (21-E3), (22-E4), (23-E5), or (24-E6).

Alternatively, the hole transport material is the compound (1-1), the binder resin is the polyarylate resin including the repeating units (10-2), (11-X1), and (11-X3), and the electron acceptor compound is the compound (20-E1), (20-E2), (21-E3), (22-E4), (23-E5), or (24-E6).

Alternatively, the hole transport material is the compound (1-2), the binder resin is the polyarylate resin including the repeating units (10-2), (11-X1), and (11-X3), and the electron acceptor compound is the compound (20-E1), (20-E2), (21-E3), (22-E4), (23-E5), or (24-E6).

Alternatively, the hole transport material is the compound (1-3), the binder resin is the polyarylate resin including the repeating units (10-2), (11-X1), and (11-X3), and the electron acceptor compound is the compound (20-E1), (20-E2), (21-E3), (22-E4), (23-E5), or (24-E6).

Alternatively, the hole transport material is the compound (1-1), the binder resin is the polyarylate resin including the repeating units (10-2), (11-X1), and (11-X2), and the electron acceptor compound is the compound (20-E1), (20-E2), (21-E3), (22-E4), (23-E5), or (24-E6).

Alternatively, the hole transport material is the compound (1-2), the binder resin is the polyarylate resin including the repeating units (10-2), (11-X1), and (11-X2), and the electron acceptor compound is the compound (20-E1), (20-E2), (21-E3), (22-E4), (23-E5), or (24-E6).

Alternatively, the hole transport material is the compound (1-3), the binder resin is the polyarylate resin including the repeating units (10-2), (11-X1), and (11-X2), and the electron acceptor compound is the compound (20-E1), (20-E2), (21-E3), (22-E4), (23-E5), or (24-E6).

Alternatively, the hole transport material is the compound (1-1), the binder resin is the polyarylate resin including the repeating units (10-3), (11-X1), and (11-X3), and the electron acceptor compound is the compound (20-E1), (20-E2), (21-E3), (22-E4), (23-E5), or (24-E6).

Alternatively, the hole transport material is the compound (1-2), the binder resin is the polyarylate resin including the repeating units (10-3), (11-X1), and (11-X3), and the electron acceptor compound is the compound (20-E1), (20-E2), (21-E3), (22-E4), (23-E5), or (24-E6).

Alternatively, the hole transport material is the compound (1-3), the binder resin is the polyarylate resin including the repeating units (10-3), (11-X1), and (11-X3), and the electron acceptor compound is the compound (20-E1), (20-E2), (21-E3), (22-E4), (23-E5), or (24-E6).

Alternatively, the hole transport material is the compound (1-1), the binder resin is the polycarbonate resin including the repeating unit (R-5), and the electron acceptor compound is the compound (20-E1), (20-E2), (21-E3), (22-E4), (23-E5), or (24-E6).

Alternatively, the hole transport material is the compound (1-2), the binder resin is the polycarbonate resin including the repeating unit (R-5), and the electron acceptor compound is the compound (20-E1), (20-E2), (21-E3), (22-E4), (23-E5), or (24-E6).

Alternatively, the hole transport material is the compound (1-3), the binder resin is the polycarbonate resin including the repeating unit (R-5), and the electron acceptor compound is the compound (20-E1), (20-E2), (21-E3), (22-E4), (23-E5), or (24-E6).

Alternatively, the hole transport material is the compound (1-1), the binder resin is the polycarbonate resin including the repeating unit (R-6), and the electron acceptor compound is the compound (20-E1), (20-E2), (21-E3), (22-E4), (23-E5), or (24-E6).

Alternatively, the hole transport material is the compound (1-2), the binder resin is the polycarbonate resin including the repeating unit (R-6), and the electron acceptor compound is the compound (20-E1), (20-E2), (21-E3), (22-E4), (23-E5), or (24-E6).

Alternatively, the hole transport material is the compound (1-3), the binder resin is the polycarbonate resin including the repeating unit (R-6), and the electron acceptor compound is the compound (20-E1), (20-E2), (21-E3), (22-E4), (23-E5), or (24-E6).

Alternatively, the hole transport material is the compound (1-1), the binder resin is the polycarbonate resin including the repeating unit (R-7), and the electron acceptor compound is the compound (20-E1), (20-E2), (21-E3), (22-E4), (23-E5), or (24-E6).

Alternatively, the hole transport material is the compound (1-2), the binder resin is the polycarbonate resin including the repeating unit (R-7), and the electron acceptor compound is the compound (20-E1), (20-E2), (21-E3), (22-E4), (23-E5), or (24-E6).

Alternatively, the hole transport material is the compound (1-3), the binder resin is the polycarbonate resin including the repeating unit (R-7), and the electron acceptor compound is the compound (20-E1), (20-E2), (21-E3), (22-E4), (23-E5), or (24-E6).

Alternatively, the hole transport material is the compound (1-1), (1-2) or (1-3), the binder resin is the polyarylate resin including the repeating units (10-1), (12-1), and (11-X3), and the electron acceptor compound is the compound (20-E2).

In order to further improve electrical characteristics of the photosensitive member being a single-layer photosensitive member and further inhibit crystallization in the photosensitive layer, preferably, the hole transport material, the binder resin, and the electron transport material are in any of the following combinations. More preferably, the hole transport material, the binder resin, and the electron transport material are in any of the following combinations, and the charge generating material is Y-form titanyl phthalocyanine.

The hole transport material is the compound (1-1), the binder resin is the polyarylate resin including the repeating units (10-1), (11-X1), and (11-X3), and the electron transport material is the compound (20-E1), (20-E2), (21-E3), (22-E4), (23-E5), or (24-E6).

Alternatively, the hole transport material is the compound (1-2), the binder resin is the polyarylate resin including the repeating units (10-1), (11-X1), and (11-X3), and the electron transport material is the compound (20-E1), (20-E2), (21-E3), (22-E4), (23-E5), or (24-E6).

Alternatively, the hole transport material is the compound (1-3), the binder resin is the polyarylate resin including the repeating units (10-1), (11-X1), and (11-X3), and the electron transport material is the compound (20-E1), (20-E2), (21-E3), (22-E4), (23-E5), or (24-E6).

Alternatively, the hole transport material is the compound (1-1), the binder resin is the polyarylate resin including the repeating units (10-2), (11-X1), and (11-X3), and the electron transport material is the compound (20-E1), (20-E2), (21-E3), (22-E4), (23-E5), or (24-E6).

Alternatively, the hole transport material is the compound (1-2), the binder resin is the polyarylate resin including the repeating units (10-2), (11-X1), and (11-X3), and the electron transport material is the compound (20-E1), (20-E2), (21-E3), (22-E4), (23-E5), or (24-E6).

Alternatively, the hole transport material is the compound (1-3), the binder resin is the polyarylate resin including the repeating units (10-2), (11-X1), and (11-X3), and the electron transport material is the compound (20-E1), (20-E2), (21-E3), (22-E4), (23-E5), or (24-E6).

Alternatively, the hole transport material is the compound (1-1), the binder resin is the polyarylate resin including the repeating units (10-2), (11-X1), and (11-X2), and the electron transport material is the compound (20-E1), (20-E2), (21-E3), (22-E4), (23-E5), or (24-E6).

Alternatively, the hole transport material is the compound (1-2), the binder resin is the polyarylate resin including the repeating units (10-2), (11-X1), and (11-X2), and the electron transport material is the compound (20-E1), (20-E2), (21-E3), (22-E4), (23-E5), or (24-E6).

Alternatively, the hole transport material is the compound (1-3), the binder resin is the polyarylate resin including the repeating units (10-2), (11-X1), and (11-X2), and the electron transport material is the compound (20-E1), (20-E2), (21-E3), (22-E4), (23-E5), or (24-E6).

Alternatively, the hole transport material is the compound (1-1), the binder resin is the polyarylate resin including the repeating units (10-3), (11-X1), and (11-X3), and the electron transport material is the compound (20-E1), (20-E2), (21-E3), (22-E4), (23-E5), or (24-E6).

Alternatively, the hole transport material is the compound (1-2), the binder resin is the polyarylate resin including the repeating units (10-3), (11-X1), and (11-X3), and the electron transport material is the compound (20-E1), (20-E2), (21-E3), (22-E4), (23-E5), or (24-E6).

Alternatively, the hole transport material is the compound (1-3), the binder resin is the polyarylate resin including the repeating units (10-3), (11-X1), and (11-X3), and the electron transport material is the compound (20-E1), (20-E2), (21-E3), (22-E4), (23-E5), or (24-E6).

Alternatively, the hole transport material is the compound (1-1), the binder resin is the polycarbonate resin including the repeating unit (R-5), and the electron transport material is the compound (20-E1), (20-E2), (21-E3), (22-E4), (23-E5), or (24-E6).

Alternatively, the hole transport material is the compound (1-2), the binder resin is the polycarbonate resin including the repeating unit (R-5), and the electron transport material is the compound (20-E1), (20-E2), (21-E3), (22-E4), (23-E5), or (24-E6).

Alternatively, the hole transport material is the compound (1-3), the binder resin is the polycarbonate resin including the repeating unit (R-5), and the electron transport material is the compound (20-E1), (20-E2), (21-E3), (22-E4), (23-E5), or (24-E6).

Alternatively, the hole transport material is the compound (1-1), the binder resin is the polycarbonate resin including the repeating unit (R-6), and the electron transport material is the compound (20-E1), (20-E2), (21-E3), (22-E4), (23-E5), or (24-E6).

Alternatively, the hole transport material is the compound (1-2), the binder resin is the polycarbonate resin including the repeating unit (R-6), and the electron transport material is the compound (20-E1), (20-E2), (21-E3), (22-E4), (23-E5), or (24-E6).

Alternatively, the hole transport material is the compound (1-3), the binder resin is the polycarbonate resin including the repeating unit (R-6), and the electron transport material is the compound (20-E1), (20-E2), (21-E3), (22-E4), (23-E5), or (24-E6).

Alternatively, the hole transport material is the compound (1-1), the binder resin is the polycarbonate resin including the repeating unit (R-7), and the electron transport material is the compound (20-E1), (20-E2), (21-E3), (22-E4), (23-E5), or (24-E6).

Alternatively, the hole transport material is the compound (1-2), the binder resin is the polycarbonate resin including the repeating unit (R-7), and the electron transport material is the compound (20-E1), (20-E2), (21-E3), (22-E4), (23-E5), or (24-E6).

Alternatively, the hole transport material is the compound (1-3), the binder resin is the polycarbonate resin including the repeating unit (R-7), and the electron transport material is the compound (20-E1), (20-E2), (21-E3), (22-E4), (23-E5), or (24-E6).

<Conductive Substrate>

No particular limitations are placed on the conductive substrate other than being a conductive substrate that can be used in the photosensitive member. The conductive substrate can be a conductive substrate of which at least a surface portion is made from a conductive material. An example of the conductive substrate is a conductive substrate made from a conductive material. Another example of the conductive substrate is a conductive substrate having a conductive material coating. Examples of conductive materials include aluminum, iron, copper, tin, platinum, silver, vanadium, molybdenum, chromium, cadmium, titanium, nickel, palladium, indium, stainless steel, and brass. Any one of the conductive materials listed above may be used independently, or any two or more of the conductive materials listed above may be used in combination (for example, as an alloy). Out of the conductive materials listed above, aluminum or an aluminum alloy is preferable in terms of favorable charge transfer from the photosensitive layer to the conductive substrate.

The shape of the conductive substrate may be selected as appropriate to match the structure of an image forming apparatus. The conductive substrate is for example a sheet-shaped conductive substrate or a drum-shaped conductive substrate. The thickness of the conductive substrate can be selected as appropriate in accordance with the shape of the conductive substrate.

<Intermediate Layer>

The intermediate layer (undercoat layer) for example contains inorganic particles and a resin that is used for the intermediate layer (intermediate layer resin). Provision of the intermediate layer is expected to facilitate flow of current generated when the photosensitive member is irradiated with light and inhibit increasing resistance, while also maintaining insulation to a sufficient degree so as to inhibit occurrence of leakage current.

Examples of inorganic particles include particles of metals (specific examples include aluminum, iron, and copper), particles of metal oxides (specific examples include titanium oxide, alumina, zirconium oxide, tin oxide, and zinc oxide), and particles of non-metal oxides (specific examples include silica). Any one type of the inorganic particles listed above may be used independently, or any two or more types of the inorganic particles listed above may be used in combination.

Examples of intermediate layer resins are the same as the examples of binder resins listed above. In order to favorably form the intermediate layer and the photosensitive layer, preferably, the intermediate layer resin is different from the binder resin contained in the photosensitive layer. The intermediate layer may contain an additive. Examples of additives that can be contained in the intermediate layer are the same as the examples of additives that can be contained in the photosensitive layer.

<Production Method of Photosensitive Member>

The following describes an example of a production method of a multi-layer photosensitive member and an example of a production method of a single-layer photosensitive member as production methods of the photosensitive layer.

(Production Method of Multi-Layer Photosensitive Member)

The production method of the multi-layer photosensitive member includes a photosensitive layer formation process including a charge generating layer formation step and a charge transport layer formation step. In the charge generating layer formation step, first, an application liquid for formation of a charge generating layer (also referred to below as an application liquid for charge generating layer formation) is prepared. The application liquid for charge generating layer formation is applied onto a conductive substrate. Next, at least a portion of a solvent in the applied application liquid for charge generating layer formation is removed to form a charge generating layer. The application liquid for charge generating layer formation for example contains a charge generating material, a base resin, and a solvent. Such an application liquid for charge generating layer formation can be prepared by dissolving or dispersing the charge generating material and the base resin in the solvent. An additive may be added to the application liquid for charge generating layer formation as necessary.

In the charge transport layer formation step, first, an application liquid for formation of a charge transport layer (also referred to below as an application liquid for charge transport layer formation) is prepared. The application liquid for charge transport layer formation is applied onto the charge generating layer. Next, at least a portion of a solvent in the applied application liquid for charge transport layer formation is removed to form a charge transport layer. The application liquid for charge transport layer formation contains the compound (1), a binder resin, and a solvent. The application liquid for charge transport layer formation can be prepared by dissolving or dispersing the compound (1) and the binder resin in the solvent. An electron acceptor compound may be added to the application liquid for charge transport layer formation. An additive may be added to the application liquid for charge transport layer formation as necessary.

(Production Method of Single-Layer Photosensitive Member)

The production method of the single-layer photosensitive member includes a photosensitive layer formation process in which an application liquid for formation of a single-layer photosensitive layer (also referred to below as an application liquid for single-layer photosensitive layer formation) is prepared. The application liquid for single-layer photosensitive layer formation is applied onto a conductive substrate. Next, at least a portion of a solvent in the applied application liquid for photosensitive layer formation is removed to form a single-layer photosensitive layer. The application liquid for single-layer photosensitive layer formation for example contains a charge generating material, the compound (1), a binder resin, and a solvent. Such an application liquid for single-layer photosensitive layer formation can be prepared by dissolving or dispersing the charge generating material, the compound (1), and the binder resin in the solvent. An electron transport material may be added to the application liquid for single-layer photosensitive layer formation. An additive may be added to the application liquid for single-layer photosensitive layer formation as necessary.

No particular limitations are placed on the solvents respectively contained in the application liquid for charge generating layer formation, the application liquid for charge transport layer formation, and the application liquid for single-layer photosensitive layer formation (also referred to below generically as application liquids) other than that the components of each of the application liquids should be soluble or dispersible in the solvent. Examples of solvents include alcohols (specific examples include methanol, ethanol, isopropanol, and butanol), aliphatic hydrocarbons (specific examples include n-hexane, octane, and cyclohexane), aromatic hydrocarbons (specific examples include benzene, toluene, and xylene), halogenated hydrocarbons (specific examples include dichloromethane, dichloroethane, carbon tetrachloride, and chlorobenzene), ethers (specific examples include dimethyl ether, diethyl ether, tetrahydrofuran, ethylene glycol dimethyl ether, and diethylene glycol dimethyl ether), ketones (specific examples include acetone, methyl ethyl ketone, and cyclohexanone), esters (specific examples include ethyl acetate and methyl acetate), dimethyl formaldehyde, dimethyl formamide, and dimethyl sulfoxide. Any one of the solvents listed above may be used independently, or any two or more of the solvents listed above may be used in combination. Out of the solvents listed above, a non-halogenated solvent (a solvent other than a halogenated hydrocarbon) is preferably used.

Preferably, the solvent contained in the application liquid for charge transport layer formation is different from the solvent contained in the application liquid for charge generating layer formation. This is because it is preferable that the charge generating layer does not dissolve in the solvent of the application liquid for charge transport layer formation when the application liquid for charge transport layer formation is applied onto the charge generating layer.

Each application liquid is prepared by dispersing the components in the solvent by mixing. Mixing or dispersion can for example be performed using a bead mill, a roll mill, a ball mill, an attritor, a paint shaker, or an ultrasonic disperser.

Each application liquid may for example contain a surfactant or a leveling agent in order to improve dispersibility of the components or improve surface flatness of the resulting layer.

No particular limitations are placed on the method by which each application liquid is applied other than being a method that enables uniform application of the application liquid. Examples of application methods include dip coating, spray coating, spin coating, and bar coating.

No particular limitations are placed on the method by which at least a portion of the solvent in each application liquid is removed other than being a method that enables evaporation of the solvent in the application liquid. Examples of removal methods include heating, pressure reduction, and a combination of heating and pressure reduction. Specific examples thereof include heat treatment (hot-air drying) using a high-temperature dryer or a reduced-pressure dryer. The heat treatment is for example performed at a temperature of at least 40° C. and no greater than 150° C. The heat treatment is for example performed for at least 3 minutes and no greater than 120 minutes.

The production methods of the photosensitive member may further include an intermediate layer formation step as necessary. The intermediate layer formation step may be performed by a method appropriately selected from known methods.

EXAMPLES

The following provides more specific description of the present invention through use of Examples. However, the present invention is not in any way limited by the scope of the Examples.

A charge generating material described below was prepared as a material for forming charge generating layers of multi-layer photosensitive members. Hole transport materials, binder resins, and electron acceptor compounds described below were prepared as materials for forming charge transport layers of the multi-layer photosensitive members. A charge generating material, hole transport materials, binder resins, and electron transport materials described below were prepared as materials for forming single-layer photosensitive layers of single-layer photosensitive members.

(Charge Generating Material)

Y-form titanyl phthalocyanine represented by chemical formula (CGM-2) described in association with the embodiment was prepared as the charge generating material.

(Electron Acceptor Compound and Electron Transport Material)

The compounds (20-E1), (20-E2), (21-E3), (22-E4), (23-E5), and (24-E6) described in association with the embodiment were prepared as the electron acceptor compounds. The compounds (20-E1), (21-E3), (22-E4), (23-E5), and (24-E6) described in association with the embodiment were prepared as the electron transport materials.

(Hole Transport Material)

The compounds (1-1) to (1-3) described in association with the embodiment were prepared as the hole transport materials. Each of the compounds (1-1) to (1-3) was synthesized according to a method described below.

(Synthesis of Compound (1-1))

A three-necked flask having a capacity of 500 mL was charged with 4,4"-dibromo-p-terphenyl (11.98 g, 30.9 mmol), palladium(II) acetate (0.069 g, 0.307 mmol), (4-dimethylaminophenyl)di-tert-butylphosphine (0.205 g, 0.772 mmol), and sodium tert-butoxide (7.702 g, 80.15 mmol). Degassing and nitrogen gas substitution were performed on the inside of the flask twice to purge the flask with nitrogen gas. Next, the flask was charged with 2,4,4'-trimethyldiphenylamine (13.85 g, 63.3 mmol) and xylene (100 mL). The flask contents were stirred at 120° C. for 3 hours under reflux. Next, the temperature of the flask contents was reduced to 50° C. The flask contents were filtered to remove ash. Thus, a filtrate was obtained. Activated clay ("SA-1", product of Nippon Activated Clay Co., Ltd., 24 g) was added to the filtrate and stirred at 80° C. for 10 hours to give a mixture. Next, the mixture was filtered to collect a filtrate. The filtrate was evaporated under reduced pressure to give a residue. Toluene in an amount of 20 g was added to the residue and heated up to 100'C. Thus, the residue was dissolved in the toluene to give a solution. N-hexane was added to the solution until the solution became slightly milky. Next, the solution was cooled to 5° C., and then filtered to collect precipitated crystals. The thus collected crystals were dried to give the compound (1-1). The mass yield of the compound (1-1) was 18.2 g. The percentage yield of the compound (1-1) from 4,4"-dibromo-p-terphenyl was 90.8% by mole.

(Synthesis of Compound (1-2))

The compound (1-2) was obtained according to the same method as in the synthesis of the compound (1-1) in all aspects other than that 63.3 mmol of (2,4-dimethylphenyl)(4'-methylphenyl)amine was changed to 63.3 mmol of (2-ethylphenyl)(4'-methylphenyl)amine.

(Synthesis of Compound (1-3))

The compound (1-3) was obtained according to the same method as in the synthesis of the compound (1-1) in all aspects other than that 63.3 mmol of (2,4-dimethylphenyl)(4'-methylphenyl)amine was changed to 63.3 mmol of (4-ethylphenyl)(4'-methylphenyl)amine.

Furthermore, compounds represented by chemical formulae (HTM-4) to (HTM-11) (also referred to below as compounds (HTM-4) to (HTM-11), respectively) were prepared as hole transport materials for use in Comparative Examples. Note that the compound (HTM-9) corresponds to terphenyl diamine represented by chemical formula (II) disclosed in Patent Literature 1.

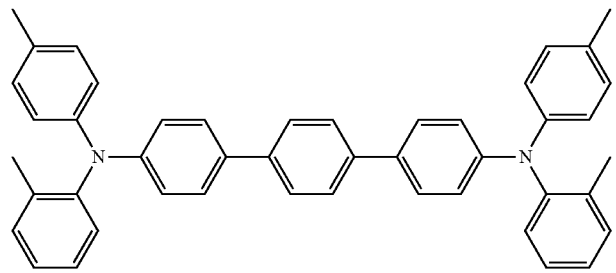

(HTM-4)

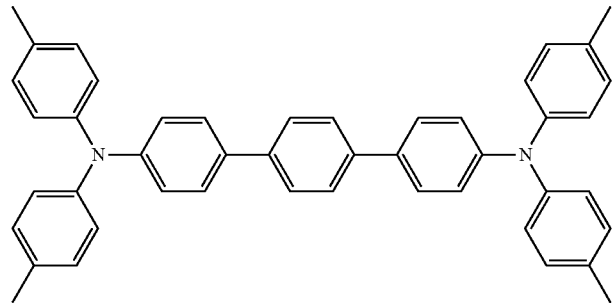

(HTM-5)

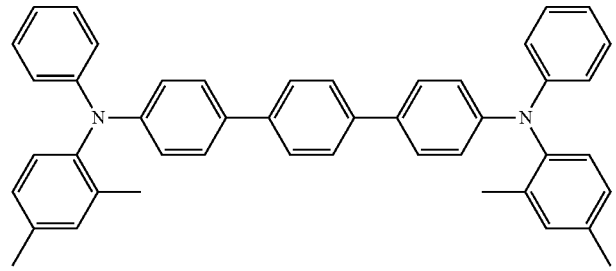

(HTM-6)

-continued
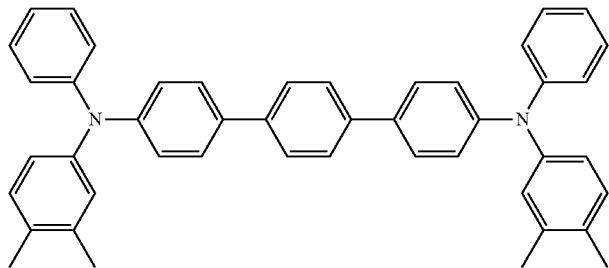
(HTM-7)
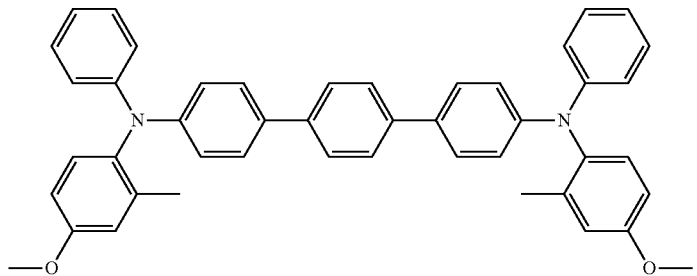
(HTM-8)
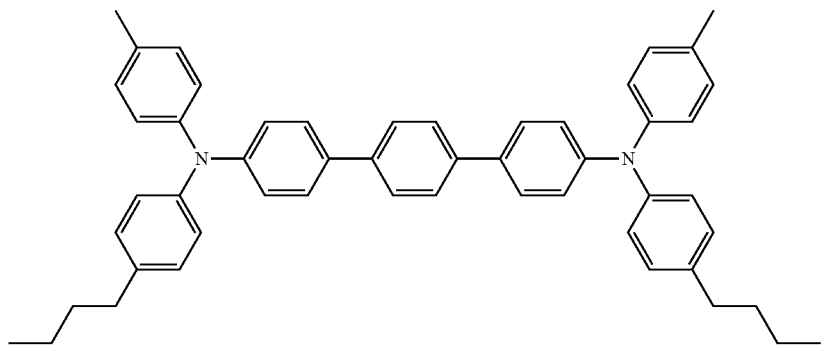
(HTM-9)
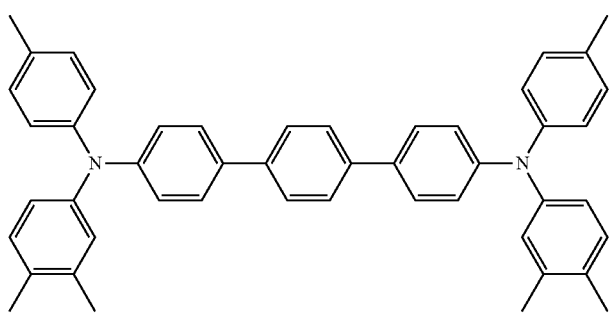
(HTM-10)
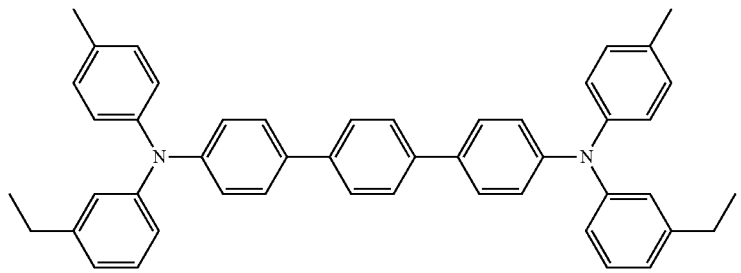
(HTM-11)

(Binder Resin)

The resins (R-1) to (R-8) described in association with the embodiment were prepared as the binder resins.

(Resin (R-1))

The resin (R-1) was a polyarylate resin including, as repeating units thereof, only the repeating units (10-1), (11-X1), and (11-X3). The resin (R-1) included, as the repeating unit (11), two different repeating units (11-X1) and (11-X3), and the ratio p thereof was 0.50. The resin (R-1) had a viscosity average molecular weight of 50,500.

(R-1)

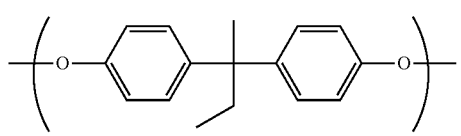
(10-1)

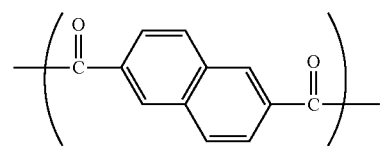
(11-X1)
p = 0.50

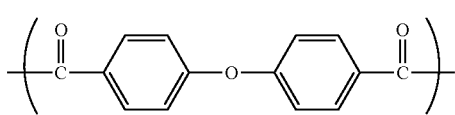
(11-X3)

The resin (R-1) was synthesized according to a method described below. Specifically, a three-necked flask having a capacity of 1 L and equipped with a thermometer, a three-way cock, and a dripping funnel having a capacity of 200 mL was used as a reaction vessel. Into the reaction vessel, 10 g (41.28 mmol) of the compound (BP-10-1), 0.062 g (0.413 mmol) of tert-butylphenol, 3.92 g (98 mmol) of sodium hydroxide, and 0.120 g (0.384 mmol) of benzyltributylammonium chloride were added. The reaction vessel was purged with argon gas. To the reaction vessel contents, 300 mL of water was added. The reaction vessel contents were stirred at 50° C. for 1 hour. Next, the reaction vessel contents were cooled to 10° C. to give an alkaline aqueous solution A.

Separately from the alkaline aqueous solution A, 4.10 g (16.2 mmol) of 2,6-naphthalenedicarboxylic acid dichloride (a dichloride of the compound (DC-11-X1)) and 4.78 g (16.2 mmol) of 4,4'-oxybisbenzoic acid dichloride (a dichloride of the compound (DC-11-X3)) were dissolved in 150 mL of chloroform. Thus, a chloroform solution B was obtained.

The chloroform solution B was gradually dripped to the alkaline aqueous solution A through the dripping funnel over 110 minutes. A polymerization reaction was caused to proceed by stirring the reaction vessel contents for 4 hours while the temperature (liquid temperature) of the reaction vessel contents was kept at 15±5° C. Next, decantation was performed to remove an upper layer (a water layer) of the reaction vessel contents to collect an organic layer. Next, 400 mL of ion exchanged water was added into a three-necked flask having a capacity of 1 L. The collected organic layer was added to the flask content. Furthermore, 400 mL of chloroform and 2 mL of acetic acid were added to the flask contents. Next, the flask contents were stirred at room temperature (25° C.) for 30 minutes. Thereafter, decantation was performed to remove an upper layer (a water layer) of the flask contents to collect an organic layer. The collected organic layer was washed with 1 L of ion exchanged water using a separatory funnel. Washing with ion exchanged water was repeated five times, and thus the water-washed organic layer was obtained.

Next, the water-washed organic layer was filtered to collect a filtrate. Into a beaker having a capacity of 1 L, 1 L of methanol was added. The collected filtrate was gradually dripped to the methanol in the beaker to give a precipitate. The precipitate was filtered off. The thus collected precipitate was vacuum dried at 70° C. for 12 hours. As a result, the resin (R-1) was obtained.

(Resin (R-2))

The resin (R-2) was a polyarylate resin including, as repeating units thereof, only the repeating units (10-2), (11-X1), and (11-X3). The resin (R-2) included, as the repeating unit (11), two different repeating units (11-X1) and (11-X3), and the ratio p thereof was 0.50. The resin (R-2) had a viscosity average molecular weight of 47.500.

(R-2)

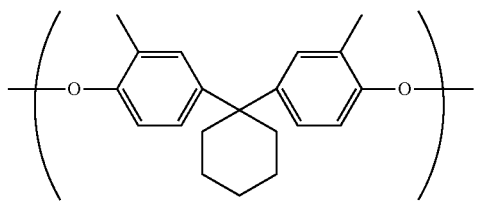
(10-2)

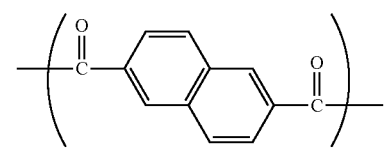
(11-X1)
p = 0.50

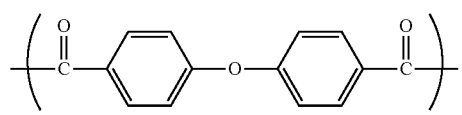
(11-X3)

The resin (R-2) was synthesized according to a method described below. Specifically, the resin (R-2) was obtained according to the same method as the synthesis method of the resin (R-1) in all aspects other than that 41.28 mmol of the compound (BP-10-1) was changed to 41.28 mmol of the compound (BP-10-2).

(Resin (R-3))

The resin (R-3) was a polyarylate resin including, as repeating units thereof, only the repeating units (10-2), (11-X1), and (11-X2). The resin (R-3) included, as the repeating unit (11), two different repeating units (11-X1) and (11-X3), and the ratio p thereof was 0.50. The resin (R-3) had a viscosity average molecular weight of 50.500.

(R-3)

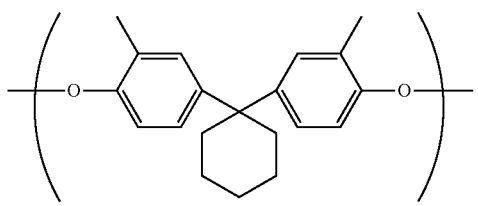
(10-2)

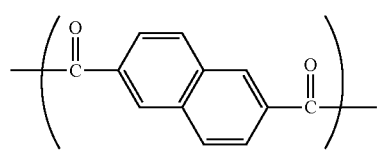
(11-X1)

p = 0.50

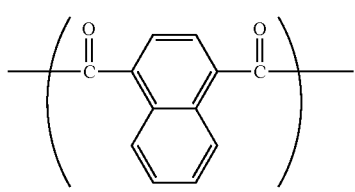
(11-X2)

The resin (R-3) was synthesized according to a method described below. Specifically, the resin (R-3) was obtained according to the same method as the synthesis method of the resin (R-1) in all aspects other than that 41.28 mmol of the compound (BP-10-1) was changed to 41.28 mmol of the compound (BP-10-2), and 16.2 mmol of the dichloride of the compound (DC-11-X3) was changed to 16.2 mmol of a dichloride of the compound (DC-11-X2).

(Resin (R-8))

The resin (R-8) was a polyarylate resin including, as repeating units thereof, only the repeating units (10-1), (12-1), and (11-X3). The ratio q of the resin (R-8) was 0.80. The resin (R-8) had a viscosity average molecular weight of 50,500.

(R-8)

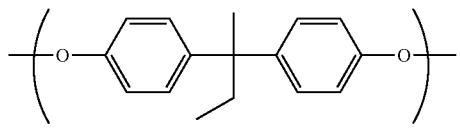
(10-1)

q = 0.80

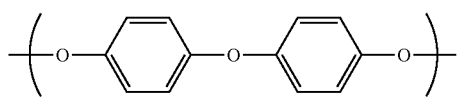
(12-1)

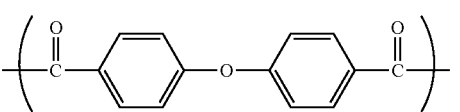
(11-X3)

The resin (R-8) was synthesized according to a method described below. Specifically, the resin (R-8) was obtained according to the same method as the synthesis method of the resin (R-1) in all aspects other than that 41.28 mmol of the compound (BP-10-1) was changed to 33.02 mmol of the compound (BP-10-1) and 8.26 mmol of the compound (BP-12-1), and 16.2 mmol of the dichloride of the compound (DC-11-X1) and 16.2 mmol of the dichloride of the compound (DC-11-X3) were changed to 32.4 mmol of the dichloride of the compound (DC-11-X3).

(Resin (R-4))

The resin (R-4) was a polyarylate resin including, as repeating units thereof, only the repeating units (10-3), (11-X1), and (11-X3). The resin (R-4) included, as the repeating unit (11), two different repeating units (11-X1) and (11-X3), and the ratio p thereof was 0.50. The resin (R-4) had a viscosity average molecular weight of 55,000.

(R-4)

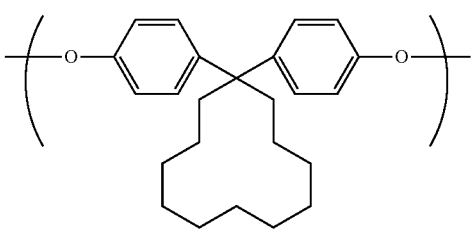
(10-3)

(11-X1)

p = 0.50

(11-X3)

The resin (R-4) was synthesized according to a method described below: Specifically, a three-necked flask having a capacity of 2 L and equipped with a thermometer, a three-way cock, and a dripping funnel having a capacity of 400 mL was used as a reaction vessel. Into the reaction vessel, 29.10 g (82.56 mmol) of the compound (BP-10-3), 0.124 g (0.826 mmol) of tert-butylphenol, 7.84 g (196 mmol) of sodium hydroxide, and 0.240 g (0.768 mmol) of benzyltributylammonium chloride were added. The reaction vessel was purged with argon gas. To the reaction vessel contents, 600 mL of water was added. The reaction vessel contents were stirred at 20° C. for 1 hour. Next, the reaction vessel contents were cooled to 10° C. to give an alkaline aqueous solution C.

Separately from the alkaline aqueous solution C, 9.84 g (38.9 mmol) of 2,6-naphthalenedicarboxylic acid dichloride (a dichloride of the compound (DC-11-X1)) and 11.47 g (38.9 mmol) of 4,4'-oxybisbenzoic acid dichloride (a dichloride of the compound (DC-11-X3)) were dissolved in 300 mL of chloroform. Thus, a chloroform solution D was obtained.

The chloroform solution D was gradually dripped to the alkaline aqueous solution C through the dripping funnel over 110 minutes. A polymerization reaction was caused to proceed by stirring the reaction vessel contents for 3 hours while the temperature (liquid temperature) of the reaction vessel contents was kept at 13±3° C. Next, decantation was performed to remove an upper layer (a water layer) of the reaction vessel contents to collect an organic layer. Next, 500 mL of ion exchanged water was added into a three-necked flask having a capacity of 2 L. The collected organic layer was added to the flask content. Furthermore, 300 g of chloroform and 6 mL of acetic acid were added to the flask contents. Next, the flask contents were stirred at room temperature (25° C.) for 30 minutes. Thereafter, decantation was performed to remove an upper layer (a water layer) of the flask contents to collect an organic layer. The collected organic layer was washed with 500 mL of ion exchanged water using a separatory funnel. Washing with ion exchanged water was repeated five times, and thus the water-washed organic layer was obtained.

Next, the water-washed organic layer was filtered to collect a filtrate. Into a beaker having a capacity of 3 L, 1.5 L of methanol was added. The collected filtrate was gradually dripped to the methanol in the beaker to give a precipitate. The precipitate was filtered off. The thus collected precipitate was vacuum dried at 70° C. for 12 hours. As a result, the resin (R-4) was obtained.

(Resin (R-5))

The resin (R-5) was a polycarbonate resin including, as a repeating unit thereof, only the repeating unit (R-5). The resin (R-5) had a viscosity average molecular weight of 50,600.

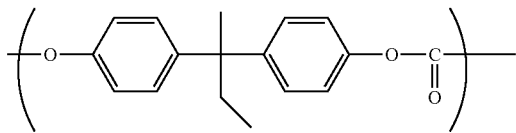
(R-5)

(Resin (R-6))

The resin (R-6) was a polycarbonate resin including, as a repeating unit thereof, only the repeating unit (R-6). The resin (R-6) had a viscosity average molecular weight of 49,400.

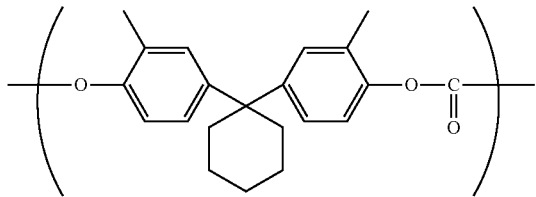
(R-6)

(Resin (R-7))

The resin (R-7) was a polycarbonate resin including, as a repeating unit thereof, only the repeating unit (R-7). The resin (R-7) had a viscosity average molecular weight of 50,900.

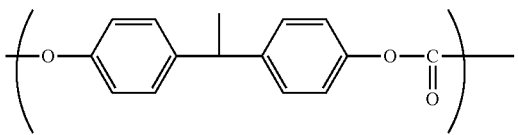
(R-7)

Next, $^1$H-NMR spectra of the compounds (1-1) to (1-3) and the resins (R-1) to (R-4) synthesized as described above were measured using a proton nuclear magnetic resonance spectrometer (product of JASCO Corporation, 300 MHz). CDCl$_3$ was used as a solvent. Tetramethylsilane (TMS) was used as an internal standard sample. Chemical shifts of the compound (1-1), which herein is a representative example of the compounds (1-1) to (1-3), are shown below. The chemical shifts confirmed that the compound (1-1) had been obtained. Chemical shifts of the resins (R-1) and (R-4), which herein are representative examples of the resins (R-1) to (R-4), are shown below. The chemical shifts confirmed that the resins (R-1) and (R-4) had been obtained. The same method was employed for the compounds (1-2) and (1-3), and the resins (R-2) and (R-3) to confirm that the compounds (1-2) and (1-3), and the resins (R-2) and (R-3) had been obtained.

Compound (1-1): $^1$H-NMR (300 MHz, CDCl$_3$) δ=7.57 (s, 4H), 7.42-7.45 (m, 4H), 7.01-7.07 (m, 18H), 2.34 (s, 6H), 2.29 (s, 6H), 2.03 (s, 6H).
Resin (R-1): $^1$H-NMR (300 MHz, CDCl$_3$) δ=8.85 (s, 2H), 8.29 (d, 2H), 8.23 (dd, 4H), 8.12 (d, 2H), 7.04-7.24 (m, 16H), 2.16 (q, 4H), 1.65 (s, 6H), 0.78 (t, 6H).
Resin (R-4): $^1$H-NMR (300 MHz, CDCl$_3$) δ=8.84 (s, 2H), 8.28 (d, 2H), 8.22 (d, 4H), 8.11 (d, 2H), 7.10-7.31 (m, 20H), 2.12 (brs, 8H), 1.38 (brs, 28H), 1.00 (brs, 8H).

<Production of Multi-Layer Photosensitive Members (A-1) to (A-23) and (B-1) to (B-8)>

Multi-layer photosensitive members (A-1) to (A-23) and (B-1) to (B-8) were produced using the charge generating material, the hole transport materials, the binder resins, and the electron acceptor compounds described above.

(Production of Multi-Layer Photosensitive Member (A-1))

First, an intermediate layer was formed. Surface-treated titanium oxide ("test sample SMT-A", product of Tayca Corporation, number average primary particle diameter: 10 nm) was prepared. The SMT-A was obtained by surface-treating titanium oxide using alumina and silica, and further surface-treating the surface-treated titanium oxide using methyl hydrogen polysiloxane while the surface-treated titanium oxide was subjected to wet dispersion. Next, the SMT-A (2 parts by mass) and a polyamide resin ("AMILAN (registered Japanese trademark) CM8000", product of Toray Industries, Inc., a four-component copolymer polyamide resin of polyamide 6, polyamide 12, polyamide 66, and polyamide 610) (1 part by mass) were added to a solvent containing methanol (10 parts by mass), butanol (1 part by mass), and toluene (1 part by mass). These materials and the solvent were mixed for 5 hours using a bead mill to disperse the materials in the solvent. Thus, an application liquid for intermediate layer formation was prepared. The thus prepared application liquid for intermediate layer formation was filtered using a filter having a pore size of 5 μm. Thereafter, the application liquid for intermediate layer formation was applied onto a surface of a conductive substrate by dip coating. As the conductive substrate, an aluminum drum-shaped support (diameter: 30 mm, total length: 246 mm) was used. Subsequently, the applied application liquid for intermediate layer formation was dried at 130° C. for 30 minutes. Through the above, an intermediate layer (film thickness: 2 μm) was formed on the conductive substrate.

Next, a charge generating layer was formed. Specifically, Y-form titanyl phthalocyanine (1.5 parts by mass) and a polyvinyl acetal resin ("S-LEC BX-5", product of Sekisui Chemical Co., Ltd.) (1 part by mass) as a base resin were added to a solvent containing propylene glycol monomethyl ether (40 parts by mass) and tetrahydrofuran (40 parts by mass). These materials and the solvent were mixed for 2 hours using a bead mill to disperse the materials in the solvent. Thus, an application liquid for charge generating layer formation was prepared. The thus prepared application liquid for charge generating layer formation was filtered using a filter having a pore size of 3 μm. Next, the resultant filtrate was applied onto the intermediate layer by dip coating and dried at 50° C. for 5 minutes. Through the above, a charge generating layer (film thickness: 0.3 μm) was formed on the intermediate layer.

Next, a charge transport layer was formed. Specifically, 60.0 parts by mass of the compound (1-1) as a hole transport material, 100.0 parts by mass of the resin (R-1) as a binder resin, 10.0 parts by mass of the compound (20-E1) as an electron acceptor compound, 0.5 parts by mass of a hindered phenol antioxidant ("IRGANOX (registered Japanese trademark) 1010", product of BASF), and 0.05 parts by mass of a leveling agent (dimethyl silicone oil, "KF96-50CS", product of Shin-Etsu Chemical Co., Ltd.) were added to a solvent containing 350.0 parts by mass of tetrahydrofuran and 350.0 parts by mass of toluene. The materials were dispersed in the solvent through mixing to prepare an application liquid for charge transport layer formation. The thus prepared application liquid for charge transport layer formation was applied onto the charge generating layer by dip coating and dried at 120° C. for 40 minutes. Through the above, a charge transport layer (film thickness: 20 μm) was formed on the charge generating layer. As a result, the multi-layer photosensitive member (A-1) was obtained. In the multi-layer photosensitive member (A-1), the intermediate layer was disposed on the conductive substrate, the charge generating layer was disposed on the intermediate layer, and the charge transport layer was disposed on the charge generating layer.

(Production of Multi-Layer Photosensitive Members (A-2) to (A-23) and (B-1) to (B-8))

Each of the multi-layer photosensitive members (A-2) to (A-23) and (B-1) to (B-8) was produced according to the same method as in the production of the multi-layer photosensitive member (A-1) in all aspects other than the following changes. While 60.0 parts by mass of the compound (1-1) was used as a hole transport material in the production of the multi-layer photosensitive member (A-1), the hole transport materials each of type and in an amount shown in Tables 1 to 3 were used in the production of the multi-layer photosensitive members (A-2) to (A-23) and (B-1) to (B-8). While the resin (R-1) was used as a binder resin in the production of the multi-layer photosensitive member (A-1), the binder resins each of type shown in Tables 1 to 3 were used in the production of the multi-layer photosensitive members (A-2) to (A-23) and (B-1) to (B-8). While 10.0 parts by mass of the compound (20-E1) was used as an electron acceptor compound in the production of the multi-layer photosensitive member (A-1), the electron acceptor compounds each of type and in an amount shown in Tables 1 to 3 were used in the production of the multi-layer photosensitive members (A-2) to (A-23) and (B-1) to (B-8).

<Evaluation of Chargeability of Multi-Layer Photosensitive Members (A-1) to (A-23) and (B-1) to (B-8)>

With respect to each of the multi-layer photosensitive members (A-1) to (A-23) and (B-1) to (B-8), chargeability of the multi-layer photosensitive member was evaluated under environmental conditions of a temperature of 10° C. and a relative humidity of 20%. Specifically, the multi-layer photosensitive member was charged using a drum sensitivity test device (product of Gen-Tech, Inc.) under conditions of a rotational speed of the multi-layer photosensitive member of 31 rpm and a current flowing into the multi-layer photosensitive member of −10 μA. A surface potential of the charged multi-layer photosensitive member was measured. The measured surface potential was taken to be a charge potential ($V_0$, unit: −V) of the multi-layer photosensitive member. Tables 1 to 3 show the charge potential ($V_0$) of each of the multi-layer photosensitive members.

<Evaluation of Sensitivity of Multi-Layer Photosensitive Members (A-1) to (A-23) and (B-1) to (B-8)>

With respect to each of the multi-layer photosensitive members (A-1) to (A-23) and (B-1) to (B-8), sensitivity of the multi-layer photosensitive member was evaluated under environmental conditions of a temperature of 10° C. and a relative humidity of 20%. Specifically, a surface of the multi-layer photosensitive member was charged to −600 V using a drum sensitivity test device (product of Gen-Tech, Inc.). Next, the surface of the multi-layer photosensitive member was irradiated with monochromatic light (wavelength: 780 nm, exposure light intensity: 0.26 μJ/cm$^2$) that had been isolated from light emitted by a halogen lamp using a band pass filter. A surface potential of the multi-layer photosensitive member was measured 50 milliseconds after completion of the irradiation with the monochromatic light. The measured surface potential was taken to be a post-irradiation potential ($V_L$, unit: −V) of the multi-layer photosensitive member. Tables 1 to 3 show the post-irradiation potential ($V_L$) of each of the multi-layer photosensitive members. Note that a smaller absolute value of the post-irradiation potential ($V_L$) indicates higher sensitivity of the multi-layer photosensitive member. The multi-layer photosensitive member was evaluated as having poor sensitivity (NG) if the absolute value of the post-irradiation potential ($V_L$) of the multi-layer photosensitive member was greater than or equal to 130 V.

<Evaluation of Crystallization Inhibition by Multi-Layer Photosensitive Members (A-1) to (A-23) and (B-1) to (B-8)>

The entirety of the surface (photosensitive layer) of each of the multi-layer photosensitive members (A-1) to (A-23) and (B-1) to (B-8) was observed with unaided eyes. Through the above, presence or absence of a crystallized portion in the photosensitive layer was confirmed. Based on the confirmation result, whether or not crystallization had been inhibited was evaluated in accordance with the following evaluation standard. Tables 1 to 3 show the evaluation results. Note that Evaluation C indicates that the multi-layer photosensitive member failed to inhibit crystallization in the photosensitive layer.

(Evaluation Standard of Crystallization Inhibition)

Evaluation A: No crystallized portion observed

Evaluation B: Crystallized portion slightly observed

Evaluation C: Crystallized portion clearly observed

HTM, Resin, EA, Parts, $V_0$, and $V_L$ in Tables 1 to 3 respectively represent hole transport material, binder resin, electron acceptor compound, parts by mass, charge potential, and post-irradiation potential.

"HTM/Resin" in Tables 1 to 3 represents ratio $m_{HTM}/m_{Resin}$ of mass $m_{HTM}$ of hole transport material to mass $m_{Resin}$ of binder resin. The ratio $m_{HTM}/m_{Resin}$ was determined in accordance with the following expression: "Ratio $m_{HTM}/m_{Resin}$=amount of hole transport material (unit: parts by mass)/amount of binder resin (unit: parts by mass)".

"EA/HTM" in Tables 1 to 3 represents ratio $m_{EA}/m_{HTM}$ of mass $m_{EA}$ of electron acceptor compound to mass $m_{HTM}$ of hole transport material. The ratio $m_{EA}/m_{HTM}$ was determined in accordance with the following expression: "Ratio $m_{EA}/m_{HTM}$=amount of electron acceptor compound (unit: parts by mass)/amount of hole transport material (unit: parts by mass)".

TABLE 1

| | Multi-layer photo-sensitive member | Charge transport layer | | | | | | | | Electrical characteristics | | |
|---|---|---|---|---|---|---|---|---|---|---|---|---|
| | | HTM | | Resin | | EA | | | | Chargeability | Sensitivity | Crystal-lization inhibition |
| | Type | Type | Amount [parts] | Type | Amount [parts] | Type | Amount [parts] | HTM/Resin | EA/HTM | $V_0$ [-V] | $V_L$ [-V] | |
| Example 1 | A-1 | 1-1 | 60.0 | R-1 | 100.0 | 20-E1 | 10.0 | 060 | 0.17 | 666 | 94 | A |
| Example 2 | A-2 | 1-2 | 60.0 | R-1 | 100.0 | 20-E1 | 10.0 | 0.60 | 0.17 | 667 | 97 | A |
| Example 3 | A-3 | 1-3 | 60.0 | R-1 | 100.0 | 20-E1 | 10.0 | 0.60 | 0.17 | 683 | 97 | A |
| Example 4 | A-4 | 1-1 | 40.0 | R-1 | 100.0 | 20-E1 | 6.7 | 0.40 | 0.17 | 661 | 118 | A |
| Example 5 | A-5 | 1-1 | 50.0 | R-1 | 100.0 | 20-E1 | 8.3 | 0.50 | 0.17 | 677 | 96 | A |
| Example 6 | A-6 | 1-1 | 80.0 | R-1 | 100.0 | 20-E1 | 13.3 | 0.80 | 0.17 | 667 | 75 | A |
| Example 7 | A-7 | 1-1 | 100.0 | R-1 | 100.0 | 20-E1 | 16.7 | 1.00 | 0.17 | 704 | 75 | A |
| Example 8 | A-8 | 1-1 | 60.0 | R-2 | 100.0 | 20-E1 | 10.0 | 0.60 | 0.17 | 666 | 98 | A |
| Example 9 | A-9 | 1-1 | 60.0 | R-3 | 100.0 | 20-E1 | 10.0 | 0.60 | 0.17 | 661 | 83 | A |
| Example 10 | A-10 | 1-1 | 60.0 | R-4 | 100.0 | 20-E1 | 10.0 | 0.60 | 0.17 | 687 | 87 | A |

TABLE 2

| | Multi-layer photo-sensitive member | Charge transport layer | | | | | | | | Electrical characteristics | | |
|---|---|---|---|---|---|---|---|---|---|---|---|---|
| | | HTM | | Resin | | EA | | | | Chargeability | Sensitivity | Crystallization inhibition |
| | Type | Type | Amount [parts] | Type | Amount [parts] | Type | Amount [parts] | HTM/Resin | EA/HTM | $V_0$ [-V] | $V_L$ [-V] | |
| Example 11 | A-11 | 1-1 | 60.0 | R-5 | 100.0 | 20-E1 | 10.0 | 0.60 | 0.17 | 685 | 95 | A |
| Example 12 | A-12 | 1-1 | 60.0 | R-6 | 100.0 | 20-E1 | 10.0 | 0.60 | 0.17 | 695 | 98 | A |
| Example 13 | A-13 | 1-1 | 60.0 | R-7 | 100.0 | 20-E1 | 10.0 | 0.60 | 0.17 | 697 | 98 | B |
| Example 14 | A-14 | 1-1 | 60.0 | R-1 | 100.0 | 20-E2 | 5.0 | 0.60 | 0.08 | 656 | 91 | A |
| Example 15 | A-15 | 1-1 | 60.0 | R-1 | 100.0 | 21-E3 | 10.0 | 0.60 | 0.17 | 671 | 99 | A |
| Example 16 | A-16 | 1-1 | 60.0 | R-1 | 100.0 | 22-E4 | 10.0 | 0.60 | 0.17 | 622 | 87 | A |
| Example 17 | A-17 | 1-1 | 60.0 | R-1 | 100.0 | 23-E5 | 10.0 | 0.60 | 0.17 | 651 | 98 | A |
| Example 18 | A-18 | 1-1 | 60.0 | R-1 | 100.0 | 24-E6 | 10.0 | 0.60 | 0.17 | 654 | 95 | A |
| Example 19 | A-19 | 1-1 | 60.0 | R-1 | 100.0 | 20-E1 | 0.6 | 0.60 | 0.01 | 650 | 99 | A |
| Example 20 | A-20 | 1-1 | 60.0 | R-1 | 100.0 | 20-E2 | 0.6 | 0.60 | 0.01 | 647 | 97 | A |
| Example 21 | A-21 | 1-1 | 60.0 | R-1 | 100.0 | None | None | 0.60 | 0.00 | 714 | 123 | A |
| Example 22 | A-22 | 1-1 | 60.0 | R-1 | 100.0 | 20-E1 | 6.0 | 0.60 | 0.10 | 714 | 94 | A |
| Example 23 | A-23 | 1-1 | 60.0 | R-1 | 100.0 | 20-E1 | 30.0 | 0.60 | 0.50 | 652 | 100 | A |

TABLE 3

| | Multi-layer photo-sensitive member Type | Charge transport layer | | | | | | | | Electrical characteristics | | |
|---|---|---|---|---|---|---|---|---|---|---|---|---|
| | | HTM | | Resin | | EA | | | | Chargeability | Sensitivity | Crystallization inhibition |
| | | Type | Amount [parts] | Type | Amount [parts] | Type | Amount [parts] | HTM/Resin | EA/HTM | $V_0$ [-V] | $V_L$ [-V] | |
| Comparative Example 1 | B-1 | HTM-4 | 60.0 | R-1 | 100.0 | 20-E1 | 10.0 | 0.60 | 0.17 | 675 | 368 (NG) | C |
| Comparative Example 2 | B-2 | HTM-5 | 60.0 | R-1 | 100.0 | 20-E1 | 10.0 | 0.60 | 0.17 | 676 | 500 (NG) | C |
| Comparative Example 3 | B-3 | HTM-6 | 60.0 | R-1 | 100.0 | 20-E1 | 10.0 | 0.60 | 0.17 | 690 | 513 (NG) | C |

TABLE 3-continued

| Multi-layer photo-sensitive member | | Charge transport layer | | | | | | | Electrical characteristics | | Crystallization inhibition |
|---|---|---|---|---|---|---|---|---|---|---|---|
| | | HTM | | Resin | | EA | | | | Chargeability | Sensitivity | |
| | Type | Type | Amount [parts] | Type | Amount [parts] | Type | Amount [parts] | HTM/ Resin | EA/ HTM | $V_0$ [−V] | $V_L$ [−V] | |
| Comparative Example 4 | B-4 | HTM-7 | 60.0 | R-1 | 100.0 | 20-E1 | 10.0 | 0.60 | 0.17 | 692 | 482 (NG) | C |
| Comparative Example 5 | B-5 | HTM-8 | 60.0 | R-1 | 100.0 | 20-E1 | 10.0 | 0.60 | 0.17 | 684 | 132 (NG) | A |
| Comparative Example 6 | B-6 | HTM-9 | 60.0 | R-1 | 100.0 | 20-E1 | 10.0 | 0.60 | 0.17 | 683 | 130 (NG) | A |
| Comparative Example 7 | B-7 | HTM-10 | 60.0 | R-1 | 100.0 | 20-E1 | 10.0 | 0.60 | 0.17 | 680 | 456 (NG) | C |
| Comparative Example 8 | B-8 | HTM-11 | 60.0 | R-1 | 100.0 | 20-E1 | 10.0 | 0.60 | 0.17 | 684 | 136 (NG) | A |

<Production of Single-Layer Photosensitive Members>

Single-layer photosensitive members (C-1) to (C-20) and (D-1) to (D-8) were produced using the charge generating material, the hole transport materials, the binder resins, and the electron transport materials described above.

(Production of Single-Layer Photosensitive Member (C-1))

A vessel was charged with 2.0 parts by mass of Y-form titanyl phthalocyanine as a charge generating material, 60.0 parts by mass of the compound (1-1) as a hole transport material, 100.0 parts by mass of the resin (R-1) as a binder resin, 25.0 parts by mass of the compound (20-E1) as an electron transport material, and 800.0 parts by mass of tetrahydrofuran as a solvent. The vessel contents were mixed for 50 hours using a ball mill to disperse the materials in the solvent. Thus, an application liquid for photosensitive layer formation was obtained. The application liquid for photosensitive layer formation was applied onto a conductive substrate (an aluminum drum-shaped support, diameter: 30 mm, total length: 238.5 mm) by dip coating. The applied application liquid for photosensitive layer formation was hot-air dried at 120° C. for 60 minutes. Through the above, a single-layer photosensitive layer (film thickness: 28 μm) was formed on the conductive substrate. As a result, the single-layer photosensitive member (C-1) was obtained. The single-layer photosensitive member (C-1) included the single-layer photosensitive layer on the conductive substrate.

(Production of Single-Layer Photosensitive Members (C-2) to (C-20) and (D-1) to (D-8))

Each of the single-layer photosensitive members (C-2) to (C-20) and (D-1) to (D-8) was produced according to the same method as in the production of the single-layer photosensitive member (C-1) in all aspects other than the following changes. While 60.0 parts by mass of the compound (1-1) was used as a hole transport material in the production of the single-layer photosensitive member (C-1), the hole transport materials each of type and in an amount shown in Tables 4 to 6 were used in the production of the single-layer photosensitive members (C-2) to (C-20) and (D-1) to (D-8). While the resin (R-1) was used as a binder resin in the production of the single-layer photosensitive member (C-1), the binder resins each of type shown in Tables 4 to 6 were used in the production of the single-layer photosensitive members (C-2) to (C-20) and (D-1) to (D-8). While 25.0 parts by mass of the compound (20-E1) was used as an electron transport material in the production of the single-layer photosensitive member (C-1), the electron transport materials each of type and in an amount shown in Tables 4 to 6 were used in the production of the single-layer photosensitive members (C-2) to (C-20) and (D-1) to (D-8).

<Evaluation of Chargeability of Single-Layer Photosensitive Members>

With respect to each of the single-layer photosensitive members (C-1) to (C-20) and (D-1) to (D-8), chargeability of the single-layer photosensitive member was evaluated under environmental conditions of a temperature of 10° C., and a relative humidity of 20%. Specifically, the single-layer photosensitive member was charged using a drum sensitivity test device (product of Gen-Tech, Inc.) under conditions of a rotational speed of the single-layer photosensitive member of 31 rpm and a current flowing into the single-layer photosensitive member of +8 μA. A surface potential of the charged single-layer photosensitive member was measured. The measured surface potential was taken to be a charge potential ($V_0$, unit: +V) of the single-layer photosensitive member. Tables 1 to 3 show the charge potential ($V_0$) of each of the single-layer photosensitive members.

<Evaluation of Sensitivity of Single-Layer Photosensitive Members>

With respect to each of the single-layer photosensitive members (C-1) to (C-20) and (D-1) to (D-8), sensitivity of the single-layer photosensitive member was evaluated under environmental conditions of a temperature of 10° C. and a relative humidity of 20%. Specifically, a surface of the single-layer photosensitive member was charged to +620 V using a drum sensitivity test device (product of Gen-Tech, Inc.). Next, the surface of the single-layer photosensitive member was irradiated with monochromatic light (wavelength: 780 nm, exposure light intensity: 1.3 μJ/cm$^2$) that had been isolated from light emitted by a halogen lamp using a band pass filter. A surface potential of the single-layer photosensitive member was measured 80 milliseconds after completion of the irradiation with the monochromatic light. The measured surface potential was taken to be a post-irradiation potential ($V_L$, unit: +V) of the single-layer photosensitive member. Tables 4 to 6 show the post-irradiation potential ($V_L$) of each of the single-layer photosensitive members. Note that a smaller absolute value of the post-irradiation potential ($V_L$) indicates higher sensitivity of the single-layer photosensitive member. The single-layer photosensitive member was evaluated as having poor sensitivity (NG) if the absolute value of the post-irradiation potential ($V_L$) of the single-layer photosensitive member was greater than or equal to 150 V.

<Evaluation of Exposure Memory-Inhibiting Performance of Single-Layer Photosensitive Members>

With respect to each of the single-layer photosensitive members (C-1) to (C-20) and (D-1) to (D-8), exposure memory-inhibiting performance of the single-layer photosensitive member was evaluated using a modified version of "MONOCHROME PRINTER FS-1300D", product of KYOCERA Document Solutions Inc. The evaluation was performed under environmental conditions of a temperature of 23° C., and a relative humidity of 50%. "KYOCERA Document Solutions-brand paper VM-A4 (A4 size)" sold by KYOCERA Document Solutions Inc. was used as evaluation paper. The photosensitive member was mounted in the evaluation apparatus, and the evaluation apparatus was set to the following conditions.

(Conditions of Evaluation Apparatus)
Linear velocity: 168 mm/second
Charger: scorotron charger
Wire current (Icc): +200 µA
Grid voltage: +600 V
Transfer process: direct transfer process
Transfer current: −20 µA
Surface electrometer: "MODEL 244", product of Monroe Electronics
Electrometer probe: "MODEL 1017AE", product of Monroe Electronics The evaluation apparatus was used to print images on four successive sheets of paper. Specifically, a white image was printed on the first and second sheets of paper, and a solid image (image density: 100%) was printed on an entire surface of the third sheet of paper, and a white image was printed on the fourth sheet of paper. Starting from initiation of the printing on the second sheet of paper, measurement of the charge potential of the photosensitive member was repeated during one rotation of the photosensitive member. An average of measured values of the charge potential was taken to be $V_{OA}$ (unit: +V). Furthermore, starting from initiation of the printing on the fourth sheet of paper, measurement of the charge potential of the photosensitive member was repeated during one rotation of the photosensitive member. An average of measured values of the charge potential was taken to be $V_{OB}$ (unit: +V). Based on the thus measured $V_{OA}$ and $V_{OB}$, a value $V_{OA}-V_{OB}$ was calculated in accordance with the expression "$V_{OA}-V_{OB}$". Tables 4 to 6 show the thus calculated values $V_{OA}-V_{OB}$. Note that a smaller value $V_{OA}-V_{OB}$ represents a lower tendency of exposure memory to occur, indicating that the single-layer photosensitive member has higher exposure memory-inhibiting performance. The single-layer photosensitive member was evaluated as having poor exposure memory-inhibiting performance (NG) if the value $V_{OA}-V_{OB}$ thereof was greater than or equal to +60 V.

<Evaluation of Crystallization Inhibition by Single-Layer Photosensitive Members)

The entirety of the surface (photosensitive layer) of each of the single-layer photosensitive members (C-1) to (C-20) and (D-1) to (D-8) was observed with unaided eyes. Through the above, presence or absence of a crystallized portion in the photosensitive layer was confirmed. Based on the confirmation result, whether or not crystallization had been inhibited was evaluated in accordance with the following evaluation standard. Tables 4 to 6 show the evaluation results. Note that Evaluation C indicates that the single-layer photosensitive member failed to inhibit crystallization in the photosensitive layer.

(Evaluation Standard of Crystallization Inhibition)
Evaluation A: No crystallized portion observed
Evaluation B: Crystallized portion slightly observed
Evaluation C: Crystallized portion clearly observed HTM, Resin, ETM, Parts, $V_0$, and $V_L$ in Tables 4 to 6 respectively represent hole transport material, binder resin, electron transport material, parts by mass, charge potential, and post-irradiation potential. "-" in Tables 4 to 6 indicates that the result of the crystallization inhibition evaluation was C, and therefore the exposure memory-inhibiting performance evaluation was not performed.

"HTM/Resin" in Tables 4 to 6 represents ratio $m_{HTM}/m_{Resin}$ of mass $m_{HTM}$ of hole transport material to mass $m_{Resin}$ of binder resin. The ratio $m_{HTM}/m_{Resin}$ was determined in accordance with the following expression: "Ratio $m_{HTM}/m_{Resin}$=amount of hole transport material (unit: parts by mass)/amount of binder resin (unit: parts by mass)".

"ETM/HTM" in Tables 4 to 6 represents ratio $m_{ETM}/m_{HTM}$ of mass $m_{ETM}$ of electron transport material to mass $m_{HTM}$ of hole transport material. The ratio $m_{ETM}/m_{HTM}$ was determined in accordance with the following expression: "Ratio $m_{ETM}/m_{HTM}$=amount of electron transport material (unit: parts by mass)/amount of hole transport material (unit: parts by mass)".

TABLE 4

| | Single-layer photosensitive member | Single-layer photosensitive layer | | | | | | | Electrical characteristics | | | |
|---|---|---|---|---|---|---|---|---|---|---|---|---|
| | | HTM | | Resin | | ETM | | HTM/Resin | ETM/HTM | Chargeability $V_0$ [+V] | Sensitivity $V_L$ [+V] | Exposure memory-inhibiting performance $V_{OA} - V_{OB}$ [V] | Crystallization inhibition |
| | | Type | Amount [parts] | Type | Amount [parts] | Type | Amount [parts] | | | | | | |
| Example 24 | C-1 | 1-1 | 60.0 | R-1 | 100.0 | 20-E1 | 25.0 | 0.60 | 0.42 | 655 | 101 | +24 | A |
| Example 25 | C-2 | 1-2 | 60.0 | R-1 | 100.0 | 20-E1 | 25.0 | 0.60 | 0.42 | 642 | 103 | +24 | A |
| Example 26 | C-3 | 1-3 | 60.0 | R-1 | 100.0 | 20-E1 | 25.0 | 0.60 | 0.42 | 653 | 100 | +25 | A |
| Example 27 | C-4 | 1-1 | 60.0 | R-1 | 100.0 | None | None | 0.60 | 0.00 | 664 | 145 | +43 | A |
| Example 28 | C-5 | 1-1 | 60.0 | R-1 | 100.0 | 20-E1 | 0.6 | 0.60 | 0.01 | 653 | 105 | +32 | A |
| Example 29 | C-6 | 1-1 | 60.0 | R-1 | 100.0 | 20-E1 | 40.0 | 0.60 | 0.67 | 644 | 96 | +23 | A |
| Example 30 | C-7 | 1-1 | 60.0 | R-1 | 100.0 | 20-E1 | 60.0 | 0.60 | 1.00 | 654 | 94 | +32 | A |
| Example 31 | C-8 | 1-1 | 60.0 | R-1 | 100.0 | 20-E1 | 90.0 | 0.60 | 1.50 | 656 | 93 | +35 | A |
| Example 32 | C-9 | 1-1 | 60.0 | R-1 | 100.0 | 20-E1 | 100.0 | 0.60 | 1.67 | 650 | 123 | +50 | B |
| Example 33 | C-10 | 1-1 | 60.0 | R-2 | 100.0 | 20-E1 | 25.0 | 0.60 | 0.42 | 648 | 100 | +23 | A |

TABLE 5

| | Single-layer photosensitive member | Single-layer photosensitive layer | | | | | | | | Electrical characteristics | | | |
|---|---|---|---|---|---|---|---|---|---|---|---|---|---|
| | | HTM | | Resin | | ETM | | | | | | Exposure memory-inhibiting performance | |
| | | | | | | | | | | Chargeability | Sensitivity | | |
| | sensitive member | Type | Amount [parts] | Type | Amount [parts] | Type | Amount [parts] | HTM/Resin | ETM/HTM | $V_0$ [+V] | $V_L$ [+V] | $V_{0A} - V_{OB}$ [V] | Crystallization inhibition |
| Example 34 | C-11 | 1-1 | 60.0 | R-3 | 100.0 | 20-E1 | 25.0 | 0.60 | 0.42 | 646 | 103 | +24 | A |
| Example 35 | C-12 | 1-1 | 60.0 | R-4 | 100.0 | 20-E1 | 25.0 | 0.60 | 0.42 | 647 | 102 | +23 | A |
| Example 36 | C-13 | 1-1 | 60.0 | R-5 | 100.0 | 20-E1 | 25.0 | 0.60 | 0.42 | 650 | 103 | +20 | A |
| Example 37 | C-14 | 1-1 | 60.0 | R-6 | 100.0 | 20-E1 | 25.0 | 0.60 | 0.42 | 651 | 101 | +24 | A |
| Example 38 | C-15 | 1-1 | 60.0 | R-1 | 100.0 | 21-E3 | 25.0 | 0.60 | 0.42 | 652 | 104 | +23 | A |
| Example 39 | C-16 | 1-1 | 60.0 | R-1 | 100.0 | 22-E4 | 25.0 | 0.60 | 0.42 | 657 | 102 | +24 | A |
| Example 40 | C-17 | 1-1 | 60.0 | R-1 | 100.0 | 23-E5 | 25.0 | 0.60 | 0.42 | 665 | 93 | +20 | A |
| Example 41 | C-18 | 1-1 | 60.0 | R-1 | 100.0 | 24-E6 | 25.0 | 0.60 | 0.42 | 664 | 101 | +19 | A |
| Example 42 | C-19 | 1-1 | 50.0 | R-1 | 100.0 | 20-E1 | 25.0 | 0.50 | 0.50 | 654 | 113 | +34 | A |
| Example 43 | C-20 | 1-1 | 40.0 | R-1 | 100.0 | 20-E1 | 25.0 | 0.40 | 0.63 | 654 | 134 | +50 | A |

TABLE 6

| | Single-layer photosensitive member | Single-layer photosensitive layer | | | | | | | | Electrical characteristics | | | |
|---|---|---|---|---|---|---|---|---|---|---|---|---|---|
| | | HTM | | Resin | | ETM | | | | | | Exposure memory-inhibiting performance | |
| | | | | | | | | | | Chargeability | Sensitivity | | |
| | | Type | Amount [parts] | Type | Amount [parts] | Type | Amount [parts] | HTM/Resin | ETM/HTM | $V_0$ [+V] | $V_L$ [+V] | V0A – VOB [V] | Crystallization inhibition |
| Comparative Example 9 | D-1 | HTM-4 | 60.0 | R-1 | 100 | 20-E1 | 25.0 | 0.60 | 0.42 | 580 | 267 (NG) | — | C |
| Comparative Example 10 | D-2 | HTM-5 | 60.0 | R-1 | 100 | 20-E1 | 25.0 | 0.60 | 0.42 | 579 | 305 (NG) | — | C |
| Comparative Example 11 | D-3 | HTM-6 | 60.0 | R-1 | 100 | 20-E1 | 25.0 | 0.60 | 0.42 | 590 | 259 (NG) | — | C |
| Comparative Example 12 | D-4 | HTM-7 | 60.0 | R-1 | 100 | 20-E1 | 25.0 | 0.60 | 0.42 | 620 | 221 (NG) | — | C |
| Comparative Example 13 | D-5 | HTM-8 | 60.0 | R-1 | 100 | 20-E1 | 25.0 | 0.60 | 0.42 | 667 | 143 | +63 (NG) | A |
| Comparative Example 14 | D-6 | HTM-9 | 60.0 | R-1 | 100 | 20-E1 | 25.0 | 0.60 | 0.42 | 671 | 162 (NG) | +67 (NG) | A |
| Comparative Example 15 | D-7 | HTM-10 | 60.0 | R-1 | 100 | 20-E1 | 25.0 | 0.60 | 0.42 | 656 | 324 (NG) | — | C |
| Comparative Example 16 | D-8 | HTM-11 | 60.0 | R-1 | 100 | 20-E1 | 25.0 | 0.60 | 0.42 | 654 | 142 | +73 (NG) | A |

Each of the multi-layer photosensitive members (A-1) to (A-23) contained the compound (1). Specifically, each of the multi-layer photosensitive members (A-1) to (A-23) contained any of the compounds (1-1), (1-2), and (1-3), which are encompassed by general formula (1). Therefore, as evident from Tables 1 and 2, the absolute value of the post-irradiation potential ($V_L$) of each of the multi-layer photosensitive members (A-1) to (A-23) was less than 130 V. That is, the multi-layer photosensitive members (A-1) to (A-23) had excellent sensitivity. Furthermore, the multi-layer photosensitive members (A-1) to (A-23) were evaluated as A or B in the crystallization inhibition evaluation. That is, the multi-layer photosensitive members (A-1) to (A-23) each inhibited crystallization in the photosensitive layer.

By contrast, each of the multi-layer photosensitive members (B-1) to (B-8) contained any of the compounds (HTM-4) to (HTM-11) as a hole transport material. However, none of the compounds (HTM-4) to (HTM-11) was a compound encompassed by general formula (1). Therefore, as evident from Table 3, the absolute value of the post-irradiation potential ($V_L$) of each of the multi-layer photosensitive members (B-1) to (B-8) was greater than or equal to 130 V. That is, the multi-layer photosensitive members (B-1) to (B-8) had poor sensitivity. Furthermore, the multi-layer photosensitive members (B-1) to (B-4) and (B-7) were evaluated as C in the crystallization inhibition evaluation. That is, the multi-layer photosensitive members (B-1) to (B-4) and (B-7) each failed to inhibit crystallization in the photosensitive layer.

Each of the single-layer photosensitive members (C-1) to (C-20) contained the compound (1). Specifically, each of the single-layer photosensitive members (C-1) to (C-20) contained any of the compounds (1-1), (1-2), and (1-3), which are encompassed by general formula (1). Therefore, as evident from Tables 4 and 5, the absolute value of the post-irradiation potential ($V_L$) of each of the single-layer photosensitive members (C-1) to (C-20) was less than 150 V That is, the single-layer photosensitive members (C-1) to (C-20) had excellent sensitivity. Furthermore, the value $V_{OA}-V_{OB}$ of each of the single-layer photosensitive members (C-1) to (C-20) was less than +60 V. That is, the single-layer photosensitive members (C-1) to (C-20) had excellent exposure memory-inhibiting performance. Furthermore, the single-layer photosensitive members (C-1) to (C-20) were evaluated as A or B in the crystallization inhibition evaluation. That is, the single-layer photosensitive members (C-1) to (C-20) each inhibited crystallization in the photosensitive layer.

By contrast, each of the single-layer photosensitive members (D-1) to (D-8) contained any of the compounds (HTM-4) to (HTM-1) as a hole transport material. However, none of the compounds (HTM-4) to (HTM-11) was a compound encompassed by general formula (1). Therefore, as evident from Table 6, the absolute value of the post-irradiation potential ($V_L$) of each of the single-layer photosensitive members (D-1) to (D-4), (D-6), and (D-7) was greater than 150 V. That is, the single-layer photosensitive members (D-1) to (D-4), (D-6), and (D-7) had poor sensitivity. Furthermore, the value $V_{OA}-V_{OB}$ of each of the single-layer photosensitive members (D-5), (D-6), and (D-8) was greater than +60 V. That is, the single-layer photosensitive members (D-5), (D-6), and (D-8) had poor exposure memory-inhibiting performance. Furthermore, the single-layer photosensitive members (D-1) to (D-4) and (D-7) were evaluated as C in the crystallization inhibition evaluation. That is, the single-layer photosensitive members (D-1) to (D-4) and (D-7) each failed to inhibit crystallization in the photosensitive layer.

These results have proved that the compound according to the present invention is capable of improving, when contained in a photosensitive layer of a photosensitive member, electrical characteristics of the photosensitive member and inhibiting crystallization in the photosensitive layer. The results have also proven that the photosensitive member according to the present invention has improved electrical characteristics and is able to inhibit crystallization in a photosensitive layer thereof.

<Consideration of Production Method of Compound (1)>

The ligands (L-1) and (L-3) to (L-6), and the coordination catalyst (L-2) described in association with the embodiment were prepared. Compounds (1) were synthesized using any of these ligands or the coordination catalyst according to a synthesis method described below.

(Synthesis of Compound (1-2) for Multi-Layer Photosensitive Member (E-1))

The reaction (r1) was carried out. Specifically, a three-necked flask having a capacity of 500) mL was charged with 4,4"-dibromo-p-terphenyl (referred to below as a compound (a-1), 11.98 g, 30.9 mmol), palladium(II) acetate being a catalyst (0.069 g, 0.307 mmol), (4-dimethylaminophenyl) di-tert-butylphosphine (ligand (L-1), 0.205 g, 0.772 mmol), and sodium tert-butoxide (7.702 g, 80.15 mmol). Degassing and nitrogen gas substitution were performed on the inside of the flask twice to purge the flask with nitrogen gas. Next, 2-ethyl-4'-methyldiphenylamine (referred to below as a compound (bc-2), 13.85 g, 63.3 mmol) and xylene (100 mL) were added to the liquid in the flask. The liquid in the flask was heated to reflux. The liquid was stirred at 130° C. for 5 hours under reflux. Next, the liquid in the flask was filtered to remove ash from the liquid without cooling the liquid. Thus, a filtrate was obtained. Next, a treatment with activated clay was performed. Specifically, 100 g of xylene and activated clay ("SA-1", product of Nippon Activated Clay Co., Ltd., 6 g) were added to the filtrate. The resultant mixture was stirred at 80° C. for 10 minutes, and then filtered to collect a filtrate. The above-described treatment with activated clay was performed three times in total. After the treatment with activated clay, the filtrate was concentrated under reduced pressure to give a liquid concentrate. Isohexane (approximately 20 g) was added to the liquid concentrate until the liquid concentrate became slightly milky. Next, 50 g of methanol was further added to the liquid concentrate. The liquid concentrate was cooled to 5° C., and then filtered to collect precipitated crystals. The thus collected crystals were dried to give the compound (1-2) for a multi-layer photosensitive member (E-1). The mass yield of the compound (1-2) for the multi-layer photosensitive member (E-1) was 20.1 g. The percentage yield of the compound (1-2) for the multi-layer photosensitive member (E-1) in the reaction (r1) was 92% by mole.

(Synthesis of Compound (I-1) for Multi-Layer Photosensitive Member (E-2))

The compound (1-1) for a multi-layer photosensitive member (E-2) was synthesized according to the same method as in the synthesis of the compound (1-2) for the multi-layer photosensitive member (E-1) in all aspects other than that 2-ethyl-4'-methyldiphenylamine (compound (bc-2), 63.3 mmol) was changed to 2,4,4'-trimethyldiphenylamine (referred to below as a compound (bc-1), 63.3 mmol). Table 7 shows the percentage yield of the compound (1-1) for the multi-layer photosensitive member (E-2) in the reaction (r1).

(Synthesis of Compound (1-2) for Multi-Layer Photosensitive Member (E-3))

The compound (1-2) for a multi-layer photosensitive member (E-3) was synthesized according to the same method as in the synthesis of the compound (1-2) for the multi-layer photosensitive member (E-1) in all aspects other than that the palladium(II) acetate (0.069 g, 0.307 mmol) was not added and the ligand (L-1) (0.772 mmol) was changed to the coordination catalyst (L-2) (0.772 mmol). Table 7 shows the percentage yield of the compound (1-2) for the multi-layer photosensitive member (E-3) in the reaction (r1).

(Synthesis of Compound (1-2) for Multi-Layer Photosensitive Member (F-1))

The compound (1-2) for a multi-layer photosensitive member (F-1) was synthesized according to the same method as in the synthesis of the compound (1-2) for the multi-layer photosensitive member (E-1) in all aspects other than that the ligand (L-1) (0.772 mmol) was changed to the ligand (L-3) (0.772 mmol). Table 7 shows the percentage yield of the compound (1-2) for the multi-layer photosensitive member (F-1) in the reaction (r1).

(Synthesis of Compound (1-2) for Multi-Layer Photosensitive Member (F-2))

The compound (1-2) for a multi-layer photosensitive member (F-2) was synthesized according to the same method as in the synthesis of the compound (1-2) for the multi-layer photosensitive member (E-1) in all aspects other than that the ligand (L-1) (0.772 mmol) was changed to the ligand (L-4) (0.772 mmol). Table 7 shows the percentage yield of the compound (1-2) for the multi-layer photosensitive member (F-2) in the reaction (r1).

(Synthesis of Compound (1-2) for Multi-Layer Photosensitive Member (F-3))

The compound (1-2) for a multi-layer photosensitive member (F-3) was synthesized according to the same method as in the synthesis of the compound (1-2) for the multi-layer photosensitive member (E-1) in all aspects other than that the ligand (L-1) (0.772 mmol) was changed to the ligand (L-5) (0.772 mmol). Table 7 shows the percentage yield of the compound (1-2) for the multi-layer photosensitive member (F-3) in the reaction (r1).

(Synthesis of Compound (1-2) for Multi-Layer Photosensitive Member (F-4))

The compound (1-2) for a multi-layer photosensitive member (F-4) was synthesized according to the same method as in the synthesis of the compound (1-2) for the multi-layer photosensitive member (E-1) in all aspects other than that the ligand (L-1) (0.772 mmol) was changed to the ligand (L-6) (tricyclohexylphosphine, 0.772 mmol). Table 7 shows the percentage yield of the compound (1-2) for the multi-layer photosensitive member (F-4) in the reaction (r1).

(Synthesis of Compound (1-2) for Multi-Layer Photosensitive Member (G-1))

First, the reaction (r0) was carried out. Specifically, a three-necked flask having a capacity of 500 mL was charged with tris(dibenzylideneacetone)dipalladium(0) (0.366 g, 0.400 mmol), (4-dimethylaminophenyl)di-tert-butylphosphine (ligand (L-1), 0.212 g, 0.800 mmol), and sodium tert-butoxide (17.686 g, 184.15 mmol). Degassing and nitrogen gas substitution were performed on the inside of the flask twice to purge the flask with nitrogen gas. Next, 2-ethylaniline (referred to below as a compound (df-2), 8.72 g, 72.0 mmol), 4-bromotoluene (referred to below as a compound (eg-1), 13.68 g, 80.0 mmol), and xylene (100 mL) were added to the liquid in the flask. The liquid in the flask was heated to reflux. The liquid was stirred at 120° C. for 3 hours under reflux, and subsequently the liquid was cooled to 50° C.

Next, the reaction (r1) was carried out without performing purification. Specifically, 4,4"-dibromo-p-terphenyl (compound (a-1), 11.98 g, 30.9 mmol), palladium(II) acetate being a catalyst (0.069 g, 0.307 mmol), and (4-dimethylaminophenyl)di-tert-butylphosphine (ligand (L-1), 0.205 g, 0.772 mmol) were added to the liquid in the flask after the reaction (r0) had been carried out. The liquid in the flask was heated up to 140° C. Through the heating, tert-butanol generated as a by-product was removed. The liquid in the flask was stirred at 140° C. for 5 hours under reflux. The liquid in the flask was filtered to remove ash from the liquid without cooling the liquid. Thus, a filtrate was obtained. Next, a treatment with activated clay was performed. Specifically, 100 g of xylene and activated clay ("SA-1", product of Nippon Activated Clay Co., Ltd., 8 g) were added to the filtrate. The resultant mixture was stirred at 80° C. for 10 minutes, and then filtered to collect a filtrate. The above-described treatment with activated clay was performed six times in total. After the treatment with activated clay, the filtrate was concentrated under reduced pressure to give a liquid concentrate. Isohexane (approximately 20 g) was added to the liquid concentrate until the liquid concentrate became slightly milky. Next, 50 g of methanol was further added to the liquid concentrate. The liquid concentrate was cooled to 5° C., and then filtered to collect precipitated crystals. The thus collected crystals were dried to give the compound (1-2) for a multi-layer photosensitive member (G-1). The mass yield of the compound (1-2) for the multi-layer photosensitive member (G-1) was 19.0 g. The percentage yield of the compound (1-2) for the multi-layer photosensitive member (G-1) for two steps through the reactions (r0) and (r1) was 89% by mole.

(Synthesis of Compound (1-2) for Multi-Layer Photosensitive Member (G-2))

The compound (1-2) for a multi-layer photosensitive member (G-2) was synthesized according to the same method as in the synthesis of the compound (1-2) for the multi-layer photosensitive member (G-1) in all aspects other than that the tris(dibenzylideneacetone)dipalladium(0) was not added in the reaction (r0), the ligand (L-1) (0.800 mmol) was changed to the coordination catalyst (L-2) (0.800 mmol) in the reaction (r0), the palladium acetate was not added in the reaction (r1), and the ligand (L-1) (0.772 mmol) was changed to the coordination catalyst (L-2) (0.772 mmol) in the reaction (r1). Table 9 shows the percentage yield of the compound (1-2) for the multi-layer photosensitive member (G-2) for two steps through the reactions (r0) and (r1).

(Synthesis of Compound (1-1) for Multi-Layer Photosensitive Member (G-3))

The compound (1-1) for a multi-layer photosensitive member (G-3) was synthesized according to the same method as in the synthesis of the compound (1-2) for the multi-layer photosensitive member (G-1) in all aspects other than that the 2-ethylaniline (compound (df-2), 72.0 mmol) was changed to 2,4-dimethylaniline (referred to below as a compound (df-1), 72.0 mmol) in the reaction (r0). Table 9 shows the percentage yield of the compound (1-1) for the multi-layer photosensitive member (G-3) for two steps through the reactions (r0) and (r1).

(Synthesis of Compound (1-2) for Multi-Layer Photosensitive Members (G-4) to (G-6))

The compound (1-2) synthesized for the multi-layer photosensitive member (G-1) was used as the compound (1-2) for multi-layer photosensitive members (G-4) to (G-6).

(Synthesis of Compound (1-2) for Multi-Layer Photosensitive Member (H-1))

The compound (1-2) for a multi-layer photosensitive member (H-1) was synthesized according to the same method as in the synthesis of the compound (1-2) for the multi-layer photosensitive member (G-1) in all aspects other than that the ligand (L-1) (0.800 mmol) was changed to the ligand (L-3) (0.800 mmol) in the reaction (r0), and the ligand (L-1) (0.772 mmol) was changed to the ligand (L-3) (0.772 mmol) in the reaction (r1). Table 9 shows the percentage yield of the compound (1-2) for the multi-layer photosensitive member (H-1) for two steps through the reactions (r0) and (r1).

(Synthesis of Compound (1-2) for Multi-Layer Photosensitive Member (H-2))

The compound (1-2) for a multi-layer photosensitive member (H-2) was synthesized according to the same method as in the synthesis of the compound (1-2) for the multi-layer photosensitive member (G-1) in all aspects other than that the ligand (L-1) (0.800 mmol) was changed to the ligand (L-4) (0.800 mmol) in the reaction (r0), and the ligand (L-1) (0.772 mmol) was changed to the ligand (L-4) (0.772 mmol) in the reaction (r1). Table 9 shows the percentage yield of the compound (1-2) for the multi-layer photosensitive member (H-2) for two steps through the reactions (r0) and (r1).

(Synthesis of Compound (1-2) for Multi-Layer Photosensitive Member (H-3))

The compound (1-2) for a multi-layer photosensitive member (H-3) was synthesized according to the same method as in the synthesis of the compound (1-2) for the multi-layer photosensitive member (G-1) in all aspects other than that the ligand (L-1) (0.800 mmol) was changed to the ligand (L-5) (0.800 mmol) in the reaction (r0), and the ligand (L-1) (0.772 mmol) was changed to the ligand (L-5) (0.772 mmol) in the reaction (r1). Table 9 shows the percentage yield of the compound (1-2) for the multi-layer photosensitive member (H-3) for two steps through the reactions (r0) and (r1).

(Synthesis of Compound (1-2) for Multi-Layer Photosensitive Member (H-4))

The compound (1-2) for a multi-layer photosensitive member (H-4) was synthesized according to the same method as in the synthesis of the compound (1-2) for the multi-layer photosensitive member (G-1) in all aspects other than that the 4-bromotoluene (compound (eg-1), 80.0 mmol) was changed to 4-chlorotoluene (referred to below as a compound (eg-2), 80.0 mmol) in the reaction (r0), the ligand (L-1) (0.800 mmol) was changed to the ligand (L-5) (0.800 mmol) in the reaction (r0), and the ligand (L-1) (0.772 mmol) was changed to the ligand (L-5) (0.772 mmol) in the reaction (r1). Table 9 shows the percentage yield of the compound (1-2) for the multi-layer photosensitive member (H-4) for two steps through the reactions (r0) and (r1).

<Production of Multi-Layer Photosensitive Members (E-1) to (E-3), (F-1) to (F-4), (G-1) to (G-6), and (H-1) to (H-4)>

(Production of Multi-Layer Photosensitive Member (E-1))

First, an intermediate layer was formed. Surface-treated titanium oxide ("test sample SMT-A", product of Tayca Corporation, number average primary particle diameter: 10 nm) was prepared. The SMT-A was obtained by surface-treating titanium oxide using alumina and silica, and further surface-treating the surface-treated titanium oxide using methyl hydrogen polysiloxane while the surface-treated titanium oxide was subjected to wet dispersion. Next, the SMT-A (2 parts by mass) and a polyamide resin ("AMILAN (registered Japanese trademark) CM8000", product of Toray Industries, Inc., a four-component copolymer polyamide resin of polyamide 6, polyamide 12, polyamide 66, and polyamide 610) (1 part by mass) were added to a solvent containing methanol (10 parts by mass), butanol (I part by mass), and toluene (I part by mass). These materials and the solvent were mixed for 5 hours using a bead mill to disperse the materials in the solvent. Thus, an application liquid for intermediate layer formation was prepared. The thus prepared application liquid for intermediate layer formation was filtered using a filter having a pore size of 5 µm. Thereafter, the application liquid for intermediate layer formation was applied onto a surface of a conductive substrate by dip coating. As the conductive substrate, an aluminum drum-shaped support (diameter: 30 mm, total length: 246 mm) was used. Subsequently, the applied application liquid for intermediate layer formation was dried at 130° C. for 30 minutes, thereby forming an intermediate layer (film thickness: 2 µm) on the conductive substrate.

Next, a charge generating layer was formed. Specifically, Y-form titanyl phthalocyanine (1.5 parts by mass) and a polyvinyl acetal resin ("S-LEC BX-5", product of Sekisui Chemical Co., Ltd.) (1 part by mass) as a base resin were added to a solvent containing propylene glycol monomethyl ether (40 parts by mass) and tetrahydrofuran (40 parts by mass). These materials and the solvent were mixed for 2 hours using a bead mill to disperse the materials in the solvent. Thus, an application liquid for charge generating layer formation was prepared. The thus prepared application liquid for charge generating layer formation was filtered using a filter having a pore size of 3 µm. Next, the resultant filtrate was applied onto the intermediate layer by dip coating and dried at 50° C. for 5 minutes. Through the above, a charge generating layer (film thickness: 0.3 µm) was formed on the intermediate layer.

Next, a charge transport layer was formed. Specifically, 100.0 parts by mass of the compound (1-2) for the multi-layer photosensitive member (E-1) as a hole transport material, 100.0 parts by mass of the resin (R-1) as a binder resin, 2.0 parts by mass of the compound (20-E2) as an electron acceptor compound, 0.5 parts by mass of a hindered phenol antioxidant ("IRGANOX (registered Japanese trademark) 1010", product of BASF), and 0.05 parts by mass of a leveling agent (dimethyl silicone oil, "KF96-50CS", product of Shin-Etsu Chemical Co., Ltd.) were added to a solvent containing 350.0 parts by mass of tetrahydrofuran and 350.0 parts by mass of toluene. The materials were dispersed in the solvent through mixing to prepare an application liquid for charge transport layer formation. The thus prepared application liquid for charge transport layer formation was applied onto the charge generating layer by dip coating and dried at 120° C. for 40 minutes. Through the above, a charge transport layer (film thickness: 20 µm) was formed on the charge generating layer. As a result, the multi-layer photosensitive member (E-1) was obtained. In the multi-layer photosensitive member (E-1), the intermediate layer was disposed on the conductive substrate, the charge generating layer was disposed on the intermediate layer, and the charge transport layer was disposed on the charge generating layer.

(Production of Multi-Layer Photosensitive Members (E-2) to (E-3), (F-1) to (F-4), (G-1) to (G-3), and (H-1) to (H-4))

The multi-layer photosensitive members (E-2) to (E-3), (F-1) to (F-4), (G-1) to (G-3), and (H-1) to (H-4) were produced according to the same method as in the production of the multi-layer photosensitive member (E-1) in all aspects other than that the hole transport materials shown in Tables 8 and 10 were used. Note that compounds shown in the column titled "HTM" for the photosensitive members shown in the column titled "Photosensitive member" in Tables 8 and 10 were used as hole transport materials. For example, with respect to the production of the multi-layer photosensitive member (E-2), Table 8 shows (E-2) in the column titled "Photosensitive member" and shows (1-1) in the column titled "HTM", thereby indicating that the compound (1-1) for the photosensitive member (E-2) was used as a hole transport material.

(Production of Multi-Layer Photosensitive Members (G-4) to (G-6))

The multi-layer photosensitive members (G-4) to (G-6) were produced according to the same method as in the production of the multi-layer photosensitive member (G-1) in all aspects other than that the binder resins shown in Table 10 were used.

Note that the ratio $m_{HTM}/m_{Resin}$ of the mass $m_{HTM}$ of the hole transport material to the mass $m_{Resin}$ of the binder resin in each of the multi-layer photosensitive members (E-1) to (E-3), (F-1) to (F-4), (G-1) to (G-6), and (H-1) to (H-4) was 1.00. The ratio $m_{EA}/m_{HTM}$ of the mass $m_{EA}$ of the electron acceptor compound to the mass $m_{HTM}$ of the hole transport material in each of the multi-layer photosensitive members (E-1) to (E-3), (F-1) to (F-4), (G-1) to (G-6), and (H-1) to (H-4) was 0.02.

<Evaluation of Chargeability of Multi-Layer Photosensitive Members (E-1) to (E-3), (F-1) to (F-4), (G-1) to (G-6), and (H-1) to (H-4)>

With respect to each of the multi-layer photosensitive members (E-1) to (E-3), (F-1) to (F-4), (G-1) to (G-6), and (H-1) to (H-4), chargeability of the multi-layer photosensitive member was evaluated under environmental conditions of a temperature of 10° C. and a relative humidity of 20%. Specifically, the multi-layer photosensitive member was charged using a drum sensitivity test device (product of Gen-Tech, Inc.) under conditions of a rotational speed of the multi-layer photosensitive member of 31 rpm and a current flowing into the multi-layer photosensitive member of −10 µA. A surface potential of the charged multi-layer photosensitive member was measured. The measured surface potential was taken to be a charge potential ($V_0$, unit: −V) of the multi-layer photosensitive member. Tables 8 and 10 show the charge potential ($V_0$) of each of the multi-layer photosensitive members.

<Evaluation of Sensitivity of Multi-Layer Photosensitive Members (E-1) to (E-3), (F-1) to (F-4), (G-1) to (G-6), and (H-1) to (H-4)>

With respect to each of the multi-layer photosensitive members (E-1) to (E-3), (F-1) to (F-4), (G-1) to (G-6), and (H-1) to (H-4), sensitivity of the multi-layer photosensitive member was evaluated under environmental conditions of a temperature of 10° C., and a relative humidity of 20%. Specifically, a surface of the multi-layer photosensitive member was charged to −600 V using a drum sensitivity test device (product of Gen-Tech, Inc.). Next, the surface of the multi-layer photosensitive member was irradiated with monochromatic light (wavelength: 780 nm, exposure light intensity: 0.80 µJ/cm$^2$) that had been isolated from light emitted by a halogen lamp using a band pass filter. A surface potential of the multi-layer photosensitive member was measured 120 milliseconds after completion of the irradiation with the monochromatic light. The measured surface potential was taken to be a post-irradiation potential ($V_L$, unit: −V) of the multi-layer photosensitive member. Tables 8 and 10 show the post-irradiation potential ($V_L$) of each of the multi-layer photosensitive members.

Pd acetate, Pd$_2$(dba)$_3$, HTM, Resin, EA, $V_0$, and $V_L$ in Tables 7 to 10 respectively represent palladium(II) acetate, tris(dibenzylideneacetone)dipalladium(0), hole transport material, binder resin, electron acceptor compound, charge potential, and post-irradiation potential.

TABLE 7

| | | | | Reaction (r1) | | | Compound (1) | |
|---|---|---|---|---|---|---|---|---|
| | Photo-sensitive member | Compound (b), (c) | Compound (a) | Catalyst | Ligand | Type | Yield [mol %] |
| Example 44 | E-1 | bc-2 | a-1 | Pd acetate | L-1 | 1-2 | 92 |
| Example 45 | E-2 | bc-1 | a-1 | Pd acetate | L-1 | 1-1 | 90 |
| Example 46 | E-3 | bc-2 | a-1 | | L-2 | 1-2 | 93 |
| Example 47 | F-1 | bc-2 | a-1 | Pd acetate | L-3 | 1-2 | 74 |
| Example 48 | F-2 | bc-2 | a-1 | Pd acetate | L-4 | 1-2 | 56 |
| Example 49 | F-3 | bc-2 | a-1 | Pd acetate | L-5 | 1-2 | 79 |
| Example 50 | F-4 | bc-2 | a-1 | Pd acetate | L-6 | 1-2 | 67 |

TABLE 8

| | Photo-sensitive member | Charge transport layer | | | Electrical characteristics | |
|---|---|---|---|---|---|---|
| | | HTM | Resin | EA | Chargeability $V_0$ [−V] | Sensitivity $V_L$ [−V] |
| Example 44 | E-1 | 1-2 | R-1 | 20-E2 | 666 | 34 |
| Example 45 | E-2 | 1-1 | R-1 | 20-E2 | 667 | 36 |
| Example 46 | E-3 | 1-2 | R-1 | 20-E2 | 687 | 32 |
| Example 47 | F-1 | 1-2 | R-1 | 20-E2 | 684 | 40 |
| Example 48 | F-2 | 1-2 | R-1 | 20-E2 | 675 | 40 |
| Example 49 | F-3 | 1-2 | R-1 | 20-E2 | 670 | 42 |
| Example 50 | F-4 | 1-2 | R-1 | 20-E2 | 670 | 42 |

TABLE 9

| | | Reaction (r0) | | | Product Reaction (r1) Material | Reaction (r1) | | | | Compound (1) | Yield for two steps [mol %] |
|---|---|---|---|---|---|---|---|---|---|---|---|
| | Photo-sensitive member | Compound (d), (f) | Compound (e), (g) | Catalyst | Ligand | Compound (b), (c) | Compound (a) | Catayst | Ligand | type | |
| Example 51 | G-1 | df-2 | eg-1 | Pd$_2$(dba)$_3$ | L-1 | bc-2 | a-1 | Pd acetate | L-1 | 1-2 | 89 |
| Example 52 | G-2 | df-2 | eg-1 | | L-2 | bc-2 | a-1 | | L-2 | 1-2 | 93 |
| Example 53 | G-3 | df-1 | eg-1 | Pd$_2$(dba)$_3$ | L-1 | bc-1 | a-1 | Pd acetate | L-1 | 1-1 | 91 |
| Example 54 | G-4 | df-2 | eg-1 | Pd$_2$(dba)$_3$ | L-1 | bc-2 | a-1 | Pd acetate | L-1 | 1-2 | 89 |
| Example 55 | G-5 | df-2 | eg-1 | Pd$_2$(dba)$_3$ | L-1 | bc-2 | a-1 | Pd acetate | L-1 | 1-2 | 89 |
| Example 56 | G-6 | df-2 | eg-1 | Pd$_2$(dba)$_3$ | L-1 | bc-2 | a-1 | Pd acetate | L-1 | 1-2 | 89 |
| Example 57 | H-1 | df-2 | eg-1 | Pd$_2$(dba)$_3$ | L-3 | bc-2 | a-1 | Pd acetate | L-3 | 1-2 | 75 |
| Example 58 | H-2 | df-2 | eg-1 | Pd$_2$(dba)$_3$ | L-4 | bc-2 | a-1 | Pd acetate | L-4 | 1-2 | 43 |
| Example 59 | H-3 | df-2 | eg-1 | Pd$_2$(dba)$_3$ | L-5 | bc-2 | a-1 | Pd acetate | L-5 | 1-2 | 77 |
| Example 60 | H-4 | df-2 | eg-2 | Pd$_2$(dba)$_3$ | L-5 | bc-2 | a-1 | Pd acetate | L-5 | 1-2 | 34 |

TABLE 10

| | Photosensitive member | Charge transport layer | | | Electrical characteristics | |
| --- | --- | --- | --- | --- | --- | --- |
| | | HTM | Resin | EA | Chargeability $V_0$ [−V] | Sensitivity $V_L$ [−V] |
| Example 51 | G-1 | 1-2 | R-1 | 20-E2 | 687 | 34 |
| Example 52 | G-2 | 1-2 | R-1 | 20-E2 | 685 | 37 |
| Example 53 | G-3 | 1-1 | R-1 | 20-E2 | 674 | 30 |
| Example 54 | G-4 | 1-2 | R-2 | 20-E2 | 674 | 36 |
| Example 55 | G-5 | 1-2 | R-3 | 20-E2 | 679 | 37 |
| Example 56 | G-6 | 1-2 | R-8 | 20-E2 | 687 | 30 |
| Example 57 | H-1 | 1-2 | R-1 | 20-E2 | 666 | 53 |
| Example 58 | H-2 | 1-2 | R-1 | 20-E2 | 675 | 53 |
| Example 59 | H-3 | 1-2 | R-1 | 20-E2 | 670 | 55 |
| Example 60 | H-4 | 1-2 | R-1 | 20-E2 | 690 | 52 |

As shown in Tables 7 and 9, the production of the compounds (1) for the multi-layer photosensitive members (E-1) to (E-3) and (G-1) to (G-6) involved causing a specific reaction between the compound (a) (specifically, compound (a-1)), the compound (b) (specifically, compound (bc-1) or (bc-2)), and the compound (c) (specifically, compound (bc-1) or (bc-2)). The specific reaction was carried out using the ligand (30) (specifically, ligand (L-1)) and a transition metal-containing catalyst (specifically, palladium(II) acetate). Alternatively, the specific reaction was carried out using palladium(II) chloride (specifically, coordination catalyst (L-2)) coordinated with the ligand (L-1). Accordingly, as shown in Tables 7 and 9, the compounds (1) for the multi-layer photosensitive members (E-1) to (E-3) and (G-1) to (G-6) were produced in higher yield than the compounds (1) for the multi-layer photosensitive members (F-1) to (F-4) and (H-1) to (H-4). Furthermore, as shown in Tables 8 and 10, the multi-layer photosensitive members (E-1) to (E-3) and (G-1) to (G-6) each containing the compound (1) produced through the specific reaction were particularly superior in sensitivity to the multi-layer photosensitive members (F-1) to (F-4) and (H-1) to (H-4).

These results have proven that the production method of the compound according to the present invention can produce the compound (1) in high yield. The results have also proven that the compound (1) produced by the production method according to the present invention is capable of particularly improving, when contained in a photosensitive layer of a photosensitive member, sensitivity of the photosensitive member.

INDUSTRIAL APPLICABILITY

The compound according to the present invention and the compound produced by the production method according to the present invention are applicable to photosensitive members. The photosensitive member according to the present invention is applicable to image forming apparatuses.

The invention claimed is:

1. An electrophotographic photosensitive member comprising a conductive substrate and a photosensitive layer, wherein
the photosensitive layer contains at least a charge generating material, a hole transport material, and a binder resin,
the hole transport material includes a compound represented by general formula (1) shown below,
the binder resin includes a polyarylate resin,
the polyarylate resin is
a polyarylate resin including repeating units represented by chemical formula (10-2), chemical formula (11-X1), and chemical formula (11-X2), or
a polyarylate resin including repeating units represented by chemical formula (10-1), chemical formula (12-1), and chemical formula (11-X3), and
the photosensitive layer includes a charge generating layer containing the charge generating material and a charge transport layer containing the hole transport material and the binder resin, or the photosensitive layer is a single-layer photosensitive layer containing the charge generating material, the hole transport material, and the binder resin,

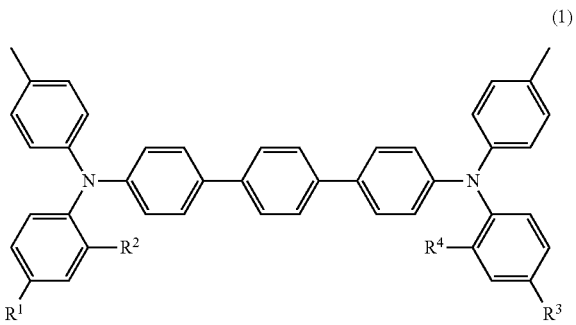
(1)

wherein in the general formula (1),
$R^1$ and $R^2$ each represent, independently of one another, a hydrogen atom, a methyl group, or an ethyl group, and a sum of the number of carbon atoms of the chemical group represented by $R^1$ and the number of carbon atoms of the chemical group represented by $R^2$ is 2, and
$R^3$ and $R^4$ each represent, independently of one another, a hydrogen atom, a methyl group, or an ethyl group, and a sum of the number of carbon atoms of the chemical group represented by $R^3$ and the number of carbon atoms of the chemical group represented by $R^4$ is 2

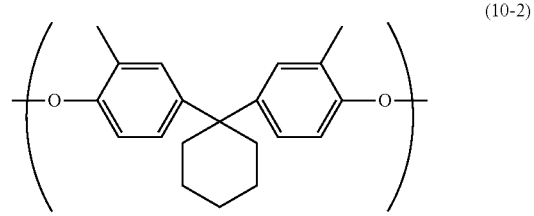
(10-2)

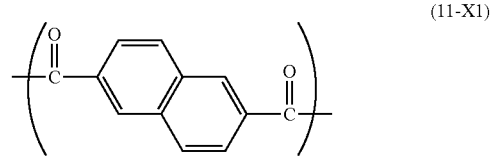
(11-X1)

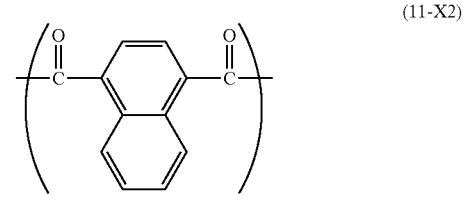
(11-X2)

-continued

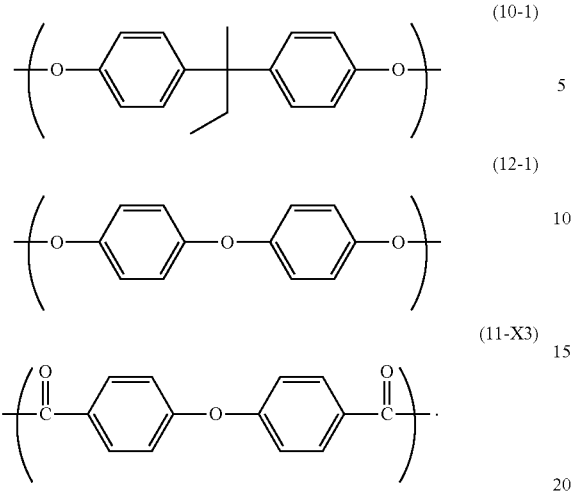

(10-1)

(12-1)

(11-X3)

2. The electrophotographic photosensitive member according to claim 1, wherein
a ratio of mass of the hole transport material to mass of the binder resin is at least 0.50.

3. The electrophotographic photosensitive member according to claim 1, wherein
the polyarylate resin is
the polyarylate resin including repeating units represented by chemical formula (10-2), the chemical formula (11-X1), and the chemical formula (11-X2).

4. The electrophotographic photosensitive member according to claim 1, wherein
the polyarylate resin is the polyarylate resin including repeating units represented by the chemical formula (10-1), the chemical formula (12-1), and the chemical formula (11-X3).

5. The electrophotographic photosensitive member according to claim 1, wherein
the photosensitive layer includes the charge generating layer and the charge transport layer,
the charge transport layer further contains an electron acceptor compound, and
a ratio of mass of the electron acceptor compound to mass of the hole transport material is at least 0.01 and no greater than 0.50.

6. The electrophotographic photosensitive member according to claim 5, wherein
the electron acceptor compound includes a compound represented by general formula (20), (21), (22), (23), or (24),

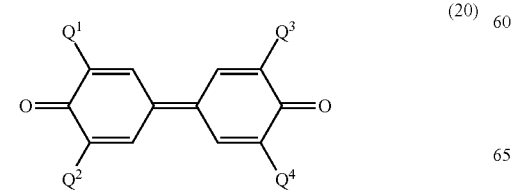

(20)

-continued

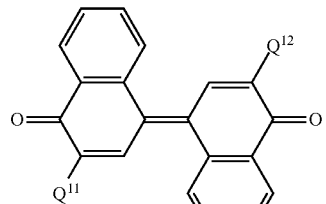

(21)

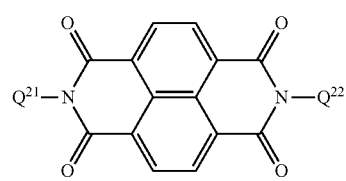

(22)

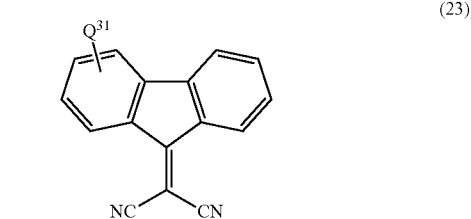

(23)

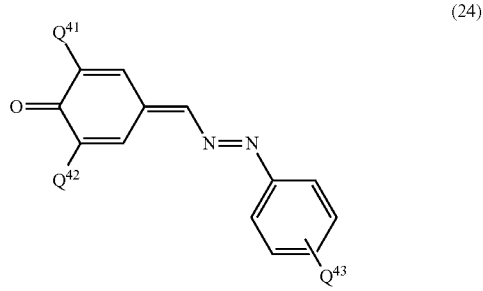

(24)

where in the general formula (20), $Q^1$, $Q^2$, $Q^3$, and $Q^4$ each represent, independently of one another, an alkyl group having a carbon number of at least 1 and no greater than 6, an alkoxy group having a carbon number of at least 1 and no greater than 6, a cycloalkyl group having a carbon number of at least 5 and no greater than 7, or an aryl group having a carbon number of at least 6 and no greater than 14, in the general formula (21), $Q^{11}$ and $Q^{12}$ each represent, independently of one another, an alkyl group having a carbon number of at least 1 and no greater than 6, an alkoxy group having a carbon number of at least 1 and no greater than 6, a cycloalkyl group having a carbon number of at least 5 and no greater than 7, or an aryl group having a carbon number of at least 6 and no greater than 14, in the general formula (22), $Q^{21}$ and $Q^{22}$ each represent, independently of one another, an aryl group having a carbon number of at least 6 and no greater than 14 and optionally having an alkyl group having a carbon number of at least 1 and no greater than 6 or an alkoxy group having a carbon number of at least 1 and no greater than 6, in the general formula (23), $Q^{31}$ represents an alkoxycarbonyl group having a carbon number of at least 2 and no greater than 7, and in the general formula (24), $Q^{41}$ and $Q^{42}$ each represent, independently of one another, an alkyl group having a carbon number of at least 1 and no greater than 6, and $Q^{43}$ represents a halogen atom.

7. The electrophotographic photosensitive member according to claim 5, wherein
the electron acceptor compound includes a compound represented by chemical formula (20-E1), (20-E2), (21-E3), (22-E4), (23-E5), or (24-E6)

(20-E1)
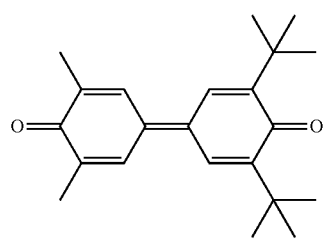

(20-E2)
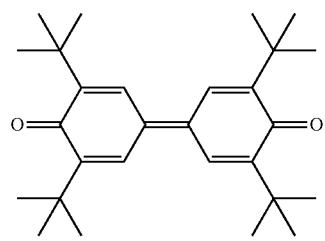

(21-E3)
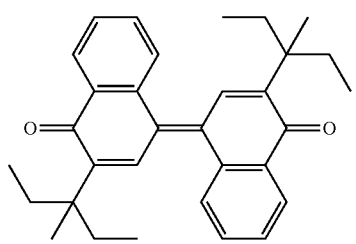

(22-E4)
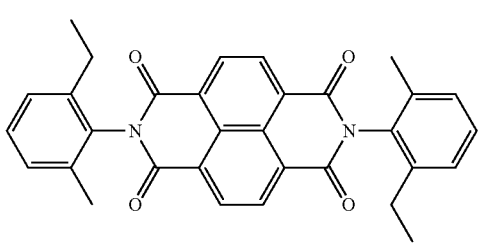

(23-E5)
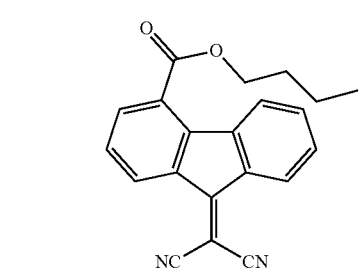

(24-E6)
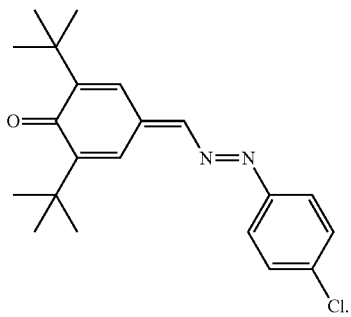

8. The electrophotographic photosensitive member according to claim 1, wherein
the photosensitive layer is the single-layer photosensitive layer,
the photosensitive layer further contains an electron transport material, and
a ratio of mass of the electron transport material to mass of the hole transport material is at least 0.01 and no greater than 1.50.

9. The electrophotographic photosensitive member according to claim 1, wherein the general formula (1) is represented by chemical formula (1-1), (1-2), or (1-3)

(1-1)
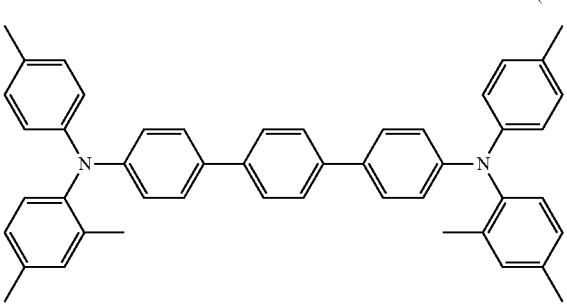

(1-2)
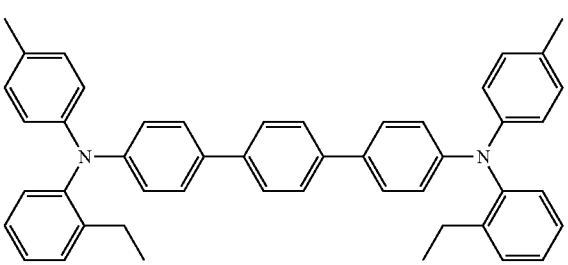

(1-3)
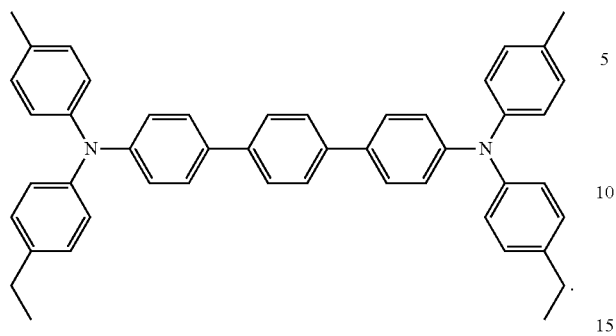
* * * * *